United States Patent [19]

Desai et al.

[11] Patent Number: 5,332,817

[45] Date of Patent: Jul. 26, 1994

[54] 3-AMINOPIPERIDINE DERIVATIVES AND RELATED NITROGEN CONTAINING HETEROCYCLES

[75] Inventors: Manoj C. Desai, Mystic; Terry J. Rosen, East Lyme, both of Conn.

[73] Assignee: Pfizer Inc., New York, N.Y.

[21] Appl. No.: 14,970

[22] Filed: Feb. 8, 1993

Related U.S. Application Data

[60] Division of Ser. No. 724,268, Jul. 1, 1991, Pat. No. 5,232,925, which is a continuation-in-part of Ser. No. 619,361, filed as PCT/US90/00116, Jan. 4. 1990, abandoned.

[51] Int. Cl.$^5$ ............................................. C07D 211/76
[52] U.S. Cl. .................................... 546/16; 546/176; 546/193; 546/199; 546/208; 546/209; 546/210; 546/212; 546/213; 546/214; 546/216; 546/218; 546/223; 546/224
[58] Field of Search ................. 546/16, 176, 193, 194, 546/208, 209, 210, 217, 213, 214, 216, 218, 223, 224

[56] References Cited

U.S. PATENT DOCUMENTS

| | | | |
|---|---|---|---|
| 3,560,510 | 2/1971 | Warawa | 260/293 |
| 3,992,389 | 11/1976 | Cavalla et al. | 260/293.76 |
| 4,785,119 | 11/1988 | Hojo et al. | 548/557 |

FOREIGN PATENT DOCUMENTS

WO/9005729 5/1990 PCT Int'l Appl.
WO/9109844 7/1991 PCT Int'l Appl.
WO/9118878 12/1991 PCT Int'l Appl.

OTHER PUBLICATIONS

Muehlstaedt et al., Chemical Abstracts, vol. 84 (1976) 89768m.
Journal Fur Praktische Chemie, 317(6), 919–925 (1975).
Desai et al., J. Med. Chem., 35, 4911–4913 (1992).

Primary Examiner—Richard L. Raymond
Attorney, Agent, or Firm—Peter C. Richardson; Paul H. Ginsburg; Karen DeBenedictis

[57] ABSTRACT

The present invention relates to novel 3-amino-piperidine derivatives and related nitrogen containing heterocyclic compounds, and specifically, to compounds of the formula

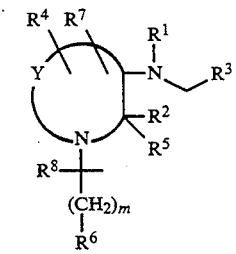

I wherein $R^1$, $R^2$, $R^3$, $R^4$, $R^5$, $R^6$, $R^7$, $R^8$, Y and m are as defined below. These novel compounds are useful in the treatment of inflammatory and central nervous system disorders, as well as other disorders. The invention also relates to novel intermediates used in the synthesis of compounds of the formula I.

2 Claims, No Drawings

3-AMINOPIPERIDINE DERIVATIVES AND RELATED NITROGEN CONTAINING HETEROCYCLES

This application is division of U.S. Ser. No. 07/724,268, which was filed in Jul. 1, 1991, now U.S. Pat. No. 5,232,925, and which is a continuation-in-part of U.S. Ser. No. 07/619,361, which was filed as PCT/US90/00116, Jan. 4, 1990, now abandoned.

BACKGROUND OF THE INVENTION

The present invention relates to novel 3-aminopiperidine derivatives and related compounds, pharmaceutical compositions comprising such compounds and the use of such compounds in the treatment and prevention of inflammatory and central nervous system disorders, as well as several other disorders. The pharmaceutically active compounds of this invention are substance P antagonists. This invention also relates to novel intermediates used in the synthesis of such substance P antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B.E.B. Sandberg et al., *Journal of Medicinal Chemistry*, 25, 1009 (1982)), as well as in central neverous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

In the recent past, some attempts have been made to provide antagonists for substance P and other tachykinin peptides in order to more effectively treat the various disorders and diseases listed above. The few such antagonists thus far described are generally peptide-like in nature and are therefore too labile from a metabolic point of view to serve as practical therapeutic agents in the treatment of disease. The non-peptidic antagonists of the present invention, on the other hand, do not possess this drawback, being far more stable from a metabolic point of view than the agents referred to above.

SUMMARY OF THE INVENTION

The present invention relates to compounds of the formula

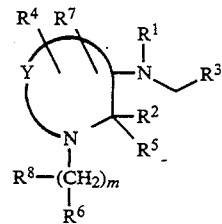

wherein

Y is $(CH_2)_n$ wherein n is an integer from 1 to 6, and wherein any one of the carbon-carbon single bonds in said $(CH_2)_n$ may optionally be replaced by a carbon-carbon double bond, and wherein any one of the carbon atoms of said $(CH_2)_n$ may optionally be substituted with $R^4$, and wherein any one of the carbon atoms of said $(CH_2)_n$ may optionally be substituted with $R^7$;

m is an integer from 0 to 8, and any one of the carbon-carbon single bonds of $(CH_2)_m$ may optionally be replaced by a carbon-carbon double bond or a carbon-carbon triple bond, and any one of the carbon atoms of said $(CH_3)_m$ may optionally be substituted with $R^8$;

$R^1$ is hydrogen or $(C_1-C_8)$ alkyl optionally substituted with hydroxy, alkoxy or fluoro;

$R^2$ is a radical selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_6)$ alkyl, $(C_1-C_6)$ alkoxy, trifluoromethyl, amino, $(C_1-C_6)$-alkylamino,

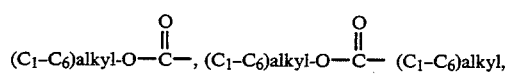

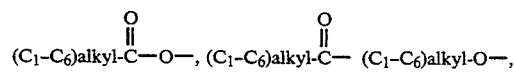

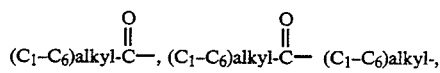

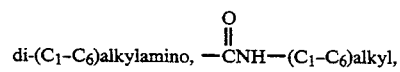

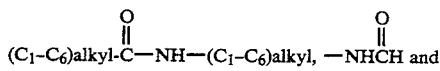

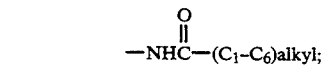

and wherein one of the phenyl moieties of said benzhydryl may optionally be replaced by naphthyl, thienyl, furyl or pyridyl;

$R^5$ is hydrogen, phenyl or $(C_1-C_6)$alkyl; or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl, $(C_1-C_6)$ alkoxy, trifluoromethyl, phenyl, amino, $(C_1-C_6)$ alkylamino,

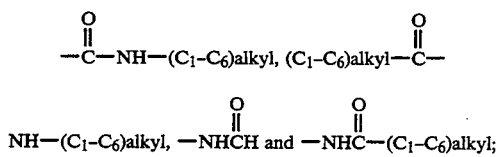

and $R^4$ and $R^7$ are each independently selected from hydrogen, hydroxy, halo, amino, oxo (=O), nitrile, $(C_1-C_6)$alkylamino, di-$(C_1-C_6)$alkylamino, $(C_1-C_6)$alkoxy,

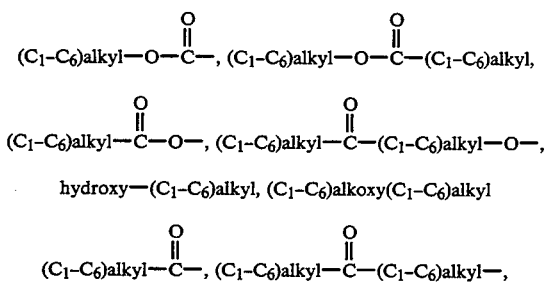

and the radicals set forth n the definition of $R^2$, $R^6$ is

$NHCH_2R^9$, $SO_2R^9$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $(C_1-C_6)$ alkyl, hydrogen, phenyl or phenyl $(C_1-C_6)$ alkyl;

with the proviso that (a) when m is O, $R^8$ is absent, (b) neither $R^4$, $R^6$, $R^7$ nor $R^8$ can form, together with the carbon to which it is attached, a ring with $R^5$, (c) when $R^4$ and $R^7$ are attached to the same carbon atom, then either each of $R^4$ and $R^7$ is independently selected from hydrogen, fluoro and $(C_1-C_6)$ alkyl, or $R^4$ and $R^7$, together with the carbon to which they are attached, form a $(C_3-C_6)$ saturated carbocyclic ring that forms a spiro compound with the nitrogen-containing ring to which they are attached, (d) when n is 2 and either $R^4$ or $R^7$ is 5-hydroxy$(C_1-C_6)$alkyl or 5-$(C_1-C_6)$alkoxy-$(C_1-C_6)$alkyl, when the other of $R^4$ and $R^7$ is hydrogen, and (e) when n is 2, neither $R^4$ nor $R^7$ is 4-hydroxy$(C_1-C_6)$alkyl or 4-$(C_1-C_6)$alkoxy-$(C_1-C_6)$alkyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The present invention also relates to compounds of the formula

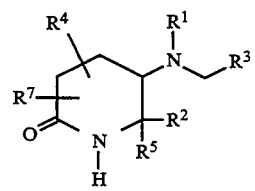

VII wherein $R^1$, $R^2$, $R^3$, $R^4$, $R^5$ and $R^7$ are as defined for compounds of the formula I. The compounds of the formula VII are novel intermediates used in the synthesis of compounds of the formula I.

The present invention also relates to the compound 3-amino-2-phenylpiperidine.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "one or more substituents," as used herein, includes from one to the maximum number of substituents possible based on the number of available bonding sites.

Preferred compounds of the formula I are those wherein $R^1$, $R^4$, $R^5$ $R^6$ and $R^7$ are hydrogen, $R^2$ is phenyl, $R^3$ is 2-methoxyphenyl wherein the phenyl moiety may optionally be substituted with chlorine, fluorine, methyl, $(C_1-C_6)$alkoxy or trifluoromethane, m is O and n is 3 or 4.

Specific preferred compounds of the formula I are:
cis-3-(2-chlorobenzylamino)-2-phenylpiperidine;
cis-3-(2-trifluoromethylbenzylamino)-2-phenylpiperidine:
cis-3-(2-methoxybenzylamino)-2-(2-fluorophenyl)-piperidine;
cis-3-(2-methoxybenzylamino)-2-(2-chlorophenyl)-piperidine;
cis-3-(2-methoxybenzylamino)-2-(2-methylphenyl)-piperidine;
cis-3-(2-methoxybenzylamino)-2-(3-methoxyphenyl)-piperidine;
cis-3-(2-methoxybenzylamino)-2-(3-fluorophenyl)-piperidine;
cis-3-(2-methoxybenzylamino)-2-(3-chlorophenyl)-piperidine;
cis-3-(2-methoxybenzylamino)-2-phenylpiperidine;

cis-3-(2-methoxybenzylamino)-2-(3-methylphenyl)-piperidine;
cis-3-(2-methoxybenzylamino)-2-(4-fluorophenyl)-piperidine;
cis-3-(2-methoxybenzylamino)-2-(3-thienyl)-piperidine;
cis-3-(2-methoxybenzylamino)-2-phenylazacyclo-heptane;
3-(2-methoxybenzylamino)-4-methyl-2-phenyl-piperidine;
3-(2-methoxybenzylamino)-5-methyl-2-phenyl-piperidine;
3-(2-methoxybenzylamino)-6-methyl-2-phenyl-piperidine;
(2S,3S)-3-(2-methoxybenzylamino)-2-phenylpiperidine;
(2S,3S)-1-(5-carboethoxypent-1-yl)-3-(2-methoxybenzylamino)-2-phenylpiperidine;
(2S,3S)-1-(6-hydroxy-hex-1-yl)-3-(2-methoxybenzylamino)-2-phenylpiperidine;
(2S,3S)-1-(4-hydroxy-4-phenylbut-1-yl)-3-(2-methoxybenzylamino)-2-phenylpiperidine;
(2S,3S)-1-(4-oxo-4-phenylbut-1-yl)-3-(2-methoxybenzylamino)-2-phenylpiperidine;
(2S,3S)-1-(5,6-dihydroxyhex-1-yl)-3-(2-methoxybenzylamino)-2-phenylpiperidine;
cis-3-(5-fluoro-2-methoxybenzylamino)-2-phenylpiperidine;
(2S,3S)-1-[4-(4-fluorophenyl)-4-oxobut-1-yl]-3-(2-methoxybenzylamino)-2-phenylpiperidine;
(2S,3S)-1-[4-[4-fluorophenyl)-4-hydroxybut-1-yl]-3-(2-methoxybenzylamino)-2-phenylpiperidine;
cis-3-(2-methoxy-5-methylbenzylamino)-2-phenylpiperidine;
(2S,3S)-1-(4-benzamidobut-1-yl)-3-(2-methoxybenzylamino)-2-phenylpiperidine;
cis-3-(2-methoxynaphth-1-ylmethylamino)-2-phenylpiperidine;
(2S,3S)-3-(2-methoxybenzylamino)-1-(5-N-methylcarboxamidopent-1-yl)-2-phenylpiperidine;
(2S,3S)-1-(4-cyanobut-1-yl)-3-(2-methoxybenzylamino)-2-phenylpiperidine;
(2S,3S)-1-[4-(2-naphthamido)but-1-yl]-3-(2-methoxybenzylamino)-2-phenylpiperidine;
(2S,3S)-1-(5-benzamidopent-1-yl)-3-(2-methoxybenzylamino)-2-phenylpiperidine;
(2S,3S)-1-(5-aminopent-1-yl)-3-(2-methoxybenzylamino)-2-phenylpiperidine;
(2S,3S)-3-(5-chloro-2-methoxybenzylamino)-2-phenyl-pipieridine;
(2S,3S)-3-(2,5-dimethoxybenzylamino)-2-phenylpiperidine;
cis-3-(3,5-difluoro-2-methoxybenzylamino)-2-phenylpiperidine;
cis-3-(4,5-difluoro-2-methoxybenzylamino)-2-phenylpiperidine;
cis-3-(2,5-dimethoxybenzylamino)-1-[4-(4-fluorophenyl)-4-oxobut-1-yl]-2-phenylpiperidine;
cis-3-(5-chloro-2-methoxybenzylamino)-1-(5,6-dihydroxyhex-1-yl)-2-phenylpiperidine;
cis-1-(5,6-dihydroxyhex-1-yl)-3-(2,5-dimethoxybenzylamino)-2-phenylpiperidine;
cis-2-phenyl-3-[-2(prop-2-yloxy)benzylamino]piperidine;
cis-3-(2,5-dimethoxybenzyl)amino-2-(3-methoxyphenyl)piperidine hydrochloride;
cis-3-(5-chloro-2-methoxybenzyl)amino-2-(3-methoxyphenyl)piperidine dihydrochloride;
cis-3-(5-chloro-2-methoxybenzyl)amino-2-(3-chlorophenyl)piperidine dihydrochloride;

3-(2-methoxybenzylamino)-2,4-diphenylpiperidine;
cis-3-(2-methoxybenzylamino)-2-phenylpyrrolidine;
(2S,3S)-3-(5-ethyl-2-methoxybenzyl)amino-2-phenylpiperidine;
(2S,3S)-3-(5-n-butyl-2-methoxybenzyl)amino-2-phenylpiperidine;
(2S,3S)-3-(2-methoxy-5-n-propylbenzyl)amino-2-phenylpiperidine;
(2S,3S)-3-(5-isopropyl-2-methoxybenzyl)amino-2-phenylpiperidine;
(2S,3S)-3-(5-s-butyl-2-methoxybenzyl)amino-2-phenylpiperidine;
(2S,3S)-3-(5-t-butyl-2-methoxybenzyl)amino-2-phenylpiperidine; and
(2S,3S)-3-(2-methoxy-5-phenylbenzyl)amino-2-phenylpiperidine.

Other compounds of the formula I are:
3-(2-methoxybenzylamino)-5-methylene-2-phenylpiperidine;
5-hydroxy-3-(2-methoxybenzylamino)-2-phenylpiperidine;
4-fluoro-3-(2-methoxybenzylamino)-2-phenyl-piperidine;
5-hydroxymethyl-3-(2-methoxybenzylamino)-2-phenylpiperidine;
5-fluoromethyl-3-(2-methoxybenzylamino)-2-phenylpiperidine;
3-(2-methoxybenzylamino)-2-phenyl-1,2,3,5-tetrahydropyridine;
6-aza-4-(2-methoxybenzylamino)-5-phenyl-spiro-[2,5-octane;
3β-(2-methoxybenzylamino)-5α-methyl-2β-phenylpiperidine;
5,5-dimethyl-3-(2-methoxybenzylamino)-2-phenylpiperidine;
5,6-dimethyl-3-(2-methoxybenzylamino)-2-phenylpiperidine;
3-(2-methoxybenzylamino)-2,2,5-triphenylpiperidine;
4-hydroxy-3-(2-methoxybenzylamino)-4-methyl-2-phenylpiperidine;
2,6-diphenyl-3-(2-methoxybenzylamino)piperidine;
1-(5-cyclohexylpent-1-yl)-3-(2-methoxybenzylamino)-2-phenylpiperidine;
2-benzhydryl-3-(2-methoxybenzylamino)piperidine;
cis-3-(5-fluoro-2-methoxybenzyl)amino-2-(3-fluorophenyl)piperidine;
cis-3-(2,5-dimethoxybenzyl)amino-2-(3-fluorophenyl)-piperidine;
cis-3-(2,4-dimethoxylbenzyl)amino-2-(3-fluorophenyl)-piperidine;
cis-3-(2-methoxy-5-methylbenzyl)amino-2-(3-fluorophenyl)piperidine;
cis-3-(5-chloro-2-methoxybenzyl)amino-2-(2-fluorophenyl)piperidine;
cis-3-(2,5-dimethoxybenzyl)amino-2-(2-fluorophenyl)-piperidine;
cis-3-(5-fluoro-2-methoxybenzyl)amino-2-(2-fluorophenyl)piperidine;
cis-2-(2-fluorophenyl)-3-(2-methoxy-5-methylbenzyl)aminopiperidine;
cis-3-(5-chloro-2-methoxybenzyl)amino-2-(3-methoxyphenyl)piperidine;
cis-3-(5-fluoro-2-methoxybenzyl)amino-2-(3-methoxyphenyl)piperidine;
cis-3-(2,5-dimethoxybenzyl)amino-2-(3-methoxyphenyl)piperidine;
cis-2-(3-methoxyphenyl)-3-(2-methoxy-5-methylphenyl)piperidine;

2-benzhydryl-3-(2-methoxybenzylamino)pyrrolidine;
cis-3-(5-chloro-2-methoxybenzyl)amino-2-(3-chlorophenyl)piperidine;
cis-3-(5-fluoro-2-methoxybenzyl)amino-2-(3-chlorophenyl)piperidine;
cis-2-(3-chlorophenyl)-3-(2,5-dimethoxybenzyl)aminopiperidine;
cis-2-(3-chlorophenyl)-3-(2-methoxy-5-methylbenzyl)aminopiperidine;
cis-3-(2,6-dichloro-4-methoxybenzylamino)-2-phenylpiperidine;
cis-3-(2,4-dichloro-6-methoxybenzylamino)-2-phenylpiperidine;
cis-3-(2,4-dimethoxybenzylamino)-2-phenylpiperidine;
cis-3-(2,3-dimethoxybenzylamino)-2-phenylpiperidine;
cis-3-(2-methoxy-3-methylbenzylamino)-2-phenylpiperidine;
cis-3-[2-(tert-butoxy)benzylamino]-2-phenylpiperidine;
cis-3-(2-cyclopentyloxybenzylamino)-2-phenylpiperidine;
cis-3-[3-(tert-butyl)-2-methoxybenzylamino)-2-phenylpiperidine;
cis-1-(2-cyanoeth-1-yl)-3-(2-methoxybenzylamino)-2-phenylpiperidine;
cis-1-(2-aminoeth-1-yl)-3-(2-methoxybenzylamino)-2-phenylpiperidine;
cis-1-(2-benzamidoeth-1-yl)-3-(2-methoxybenzylamino)-2-phenylpiperidine;
cis-1-[4-(tert-butyramido)but-1-yl]-3(2-methoxybenzylamino)-2-phenylpiperidine;
cis-1-(4-N-methylcarboxamidobut-1-yl)-3-(2-methoxybenzylamino)-2-phenylpiperidine;
cis-1-(3,5-dihydroxypent-1-yl)-3-(2-methoxybenzylamino)-2-phenylpiperidine;
2,2-diphenyl-3-(2-methoxybenzylamino)piperidine;
3-(2-methoxybenzylamino)-2-methyl-2-phenylpiperidine;
cis-3-(2,5-dimethoxybenzylamino)-2-diphenlmethylpiperidine;
cis-3-(5-chloro-2-methoxybenzylamino)-2-diphenylmethylpiperidine;
cis-3-(2-methoxybenzylamino)-2-(pyrid-3-yl)piperidine;
3-(2-methoxybenzylamino)-4-phenylpiperidine;
cis-3-(5-t-butyl-2-methoxybenzyl)amino-2-phenylpyrrolidine;
cis-2-benzhydryl-3-(5-t-Butyl-2-methoxybenzyl)aminopyrrolidine;
cis-3-(5-isopropyl-2-methoxybenzyl)amino-2-phenylpyrrolidine;
cis-2-benzhydryl-3-(5-isopropyl-2-methoxybenzyl)aminopyrrolidine;
cis-3-(5-ethyl-2-methoxybenzyl)amino-2phenylpyrrolidine;
cis-2-benzhydryl-3-(5-ethyl-2-methoxybenzyl)aminopyrrolidine;
cis-1-aza-3-(5-t-butyl-2-methoxybenzyl)amino-2-phenylcycloheptane;
cis-1-aza-2-benzhydryl-3-(5-t-butyl-2-methoxybenzyl)aminocycloheptane;
cis-1-aza-3-(5-isopropyl-2-methoxybenzyl)amino-2-phenylazacycloheptane;
cis-1-aza-2-benzhydryl-3-(5-isopropyl-2-methoxybenzyl)aminocycloheptane;
cis-1-aza-3-(5-ethyl-2-methoxybenzyl)amino-2-phenylcycloheptane;
cis-1-aza-2-benzhydryl-3-(5-ethyl-2-methoxybenzyl)aminocycloheptane;
(2S,3S)-3-(2-isopropoxy-5-isopropylbenzyl)amino-2-phenylpiperidine;
(2S,3S)-3-(5-t-butyl-2-isopropoxybenzyl)amino-2-phenylpiperidine;
cis-2-benzhydryl-3-(5-t-butyl-2-methoxyphenyl)aminopiperidine;
cis-2-benzhydryl-3-(5-isopropyl-2-methoxybenzyl)aminopiperidine;
cis-2-benzhydryl-3-(5-ethyl-2-methoxybenzyl)aminopiperidine;
cis-3-(5-t-butyl-2-methoxybenzyl)amino-2-methyl-2-phenylpiperidine;
cis-3-(5-isopropyl-2-methoxybenzyl)amino-2-methyl-2-phenylpiperidine; and
cis-3-(5-ethyl-2-methoxybenzyl)amino-2-methyl-2-phenylpiperidine.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystropy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formula I have chiral centers and therefore exist in different enantiomeric forms. This invention relates to all optical isomers and all stereoisomers of compounds of the formula I, and mixtures thereof.

Formulae I and VII above include compounds identical to those depicted but for the fact that one or more hydrogen or carbon atoms are replaced by radioactive isotopes thereof. Such radiolabelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like. Included among the radiolabelled forms of compounds of the formulae I and VII are the tritium and $C^{14}$ isotopes thereof.

DETAILED DESCRIPTION OF THE INVENTION

The compounds of the formula I may be prepared as described in the following reaction schemes and discussion. Each of the formulae designated IA, IB, IC, and ID represents a different group of compounds having the general formula I. Unless otherwise indicated, $R^1$, $R^2$, $R^3$, $R^4$, $R^5$, $R^6$, $R^7$, $R^8$, Y, n and m in the reaction schemes and discussion that follow are defined as above.

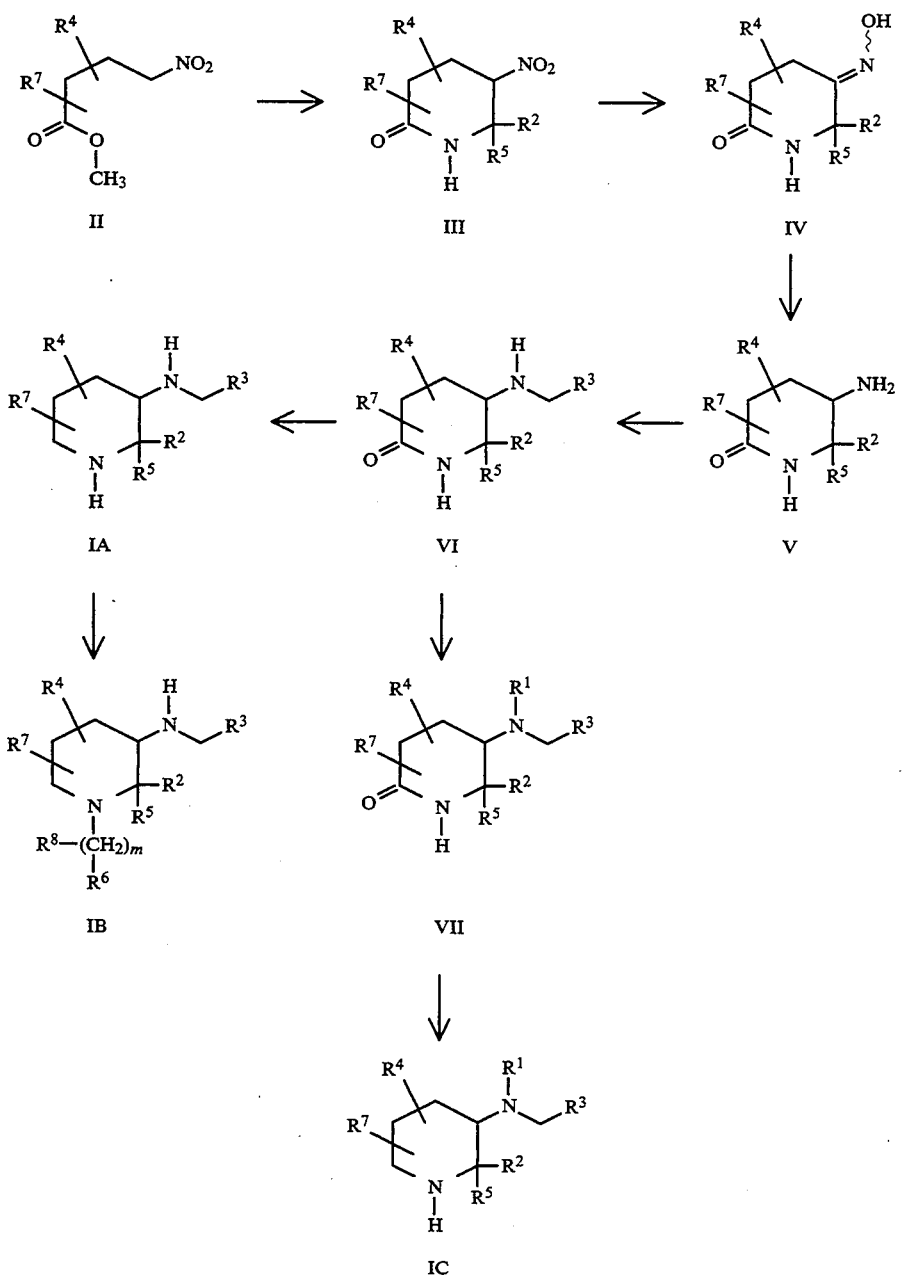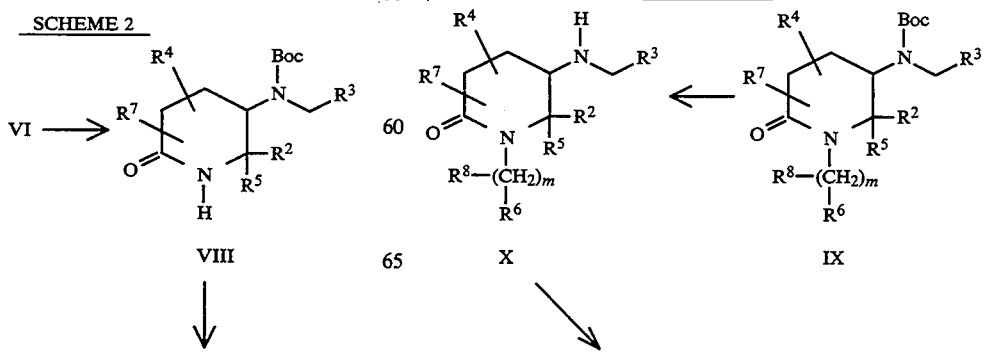

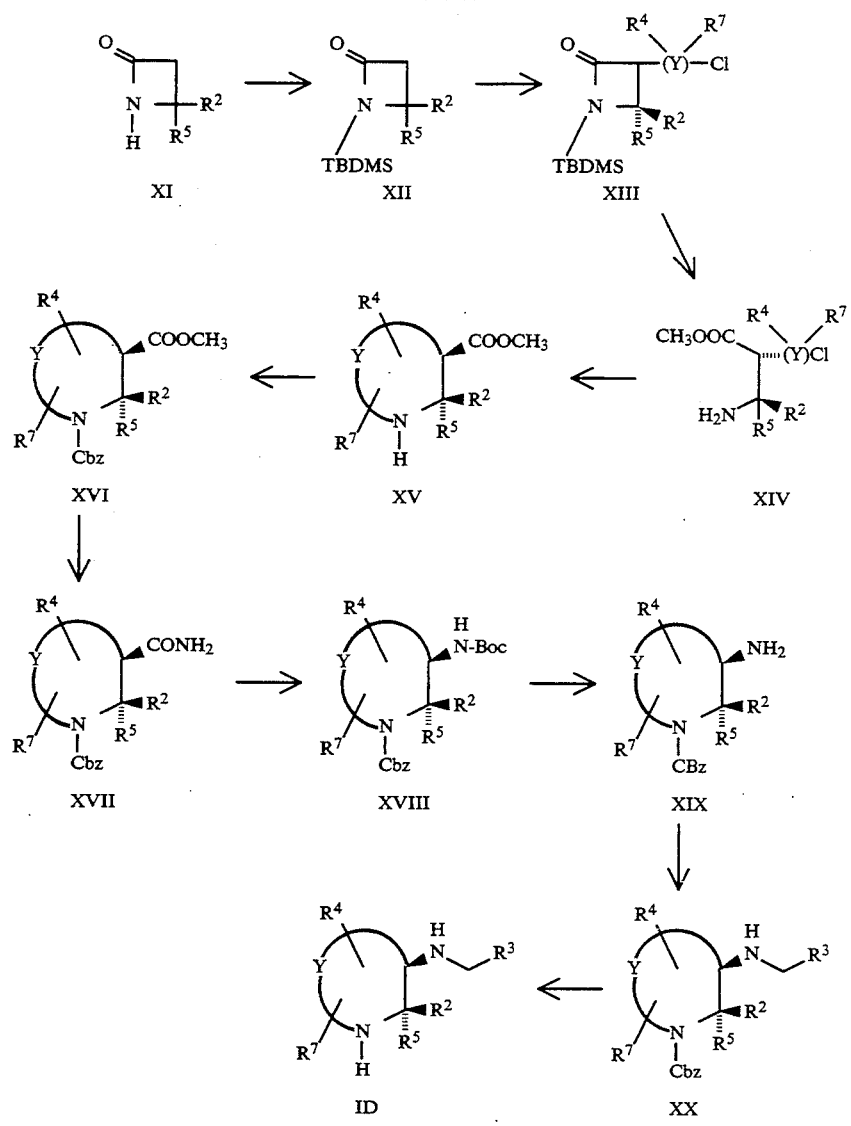

-continued
SCHEME 4
SCHEME 3

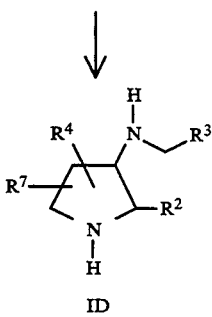

ID

Scheme 1 illustrates the preparation of compounds of the formulae IA, IB and IC. Formula IA represents compounds of the formula I wherein each of $R^1$ and $R^6$ is hydrogen, m is 0 and n is 3, with the proviso that $R^2$ is not benzhydryl and neither $R^4$ nor $R^7$ is attached to the "6" position of the piperidine ring. Formula IB represents compounds of the formula I wherein $R^1$ is hydrogen and n is 3, with the proviso that $R^2$ is not benzhydryl and neither $R^4$ nor $R^7$ is attached to the "6" position of the piperidine ring. Formula IC represents compounds of the formula I wherein $R^6$ is hydrogen, m is 0 and n is 3, with the proviso that $R^2$ is not benzhydryl and neither $R^4$ nor $R^7$ is attached to the "6" position of the piperidine ring.

Referring to scheme 1, a compound of the formula II is reacted with a compound of the formula

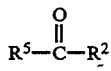

in the presence of ammonium acetate, in a polar solvent such as ethanol, acetic acid or dimethyl sulfoxide. Ethanol is the preferred solvent. Temperatures from about room temperature to about 150° C. are suitable, with the reflux temperature of the solvent being preferred. This reaction yields, by intramolecular condensation, a compound of the formula III (Von M. Muhlstadt and B. Schulze, *J. Prak. Chem*, 317, 919 (1975)).

The condensation product of formula III is then converted, via a Nef reaction, to an oxime of the formula IV. This reaction may be carried out using reagents such as aqueous Ti(III) chloride, potassium permanganate, pyridine/hexamethylphosphoramide complex of molybdenum pentoxide, tributylphosphinediphenyl disulphide or ozone in the presence of a base. Suitable temperatures range from about −100° C. to about 0° C. Preferably, the reaction is performed by bubbling ozone through the reaction mixture in the presence of potassium t-butoxide at about −78° C., and then quenching the reaction mixture with hydroxylamine hydrochloride at ambient temperature.

The oxime of formula IV is then reduced to yield both the cis and trans isomers of a compound of the formula V. Suitable reducing agents include Raney nickel/hydrogen, 10% palladium on charcoal/hydrogen, and aluminum amalgam. Preferably, the reduction is carried out using Raney nickel in ethanol under a hydrogen gas pressure of about 3 atm and at a temperature of about 25° C. Temperatures from about 10° C. to about 60° C. and pressures from about 1 to about 10 atmospheres are also suitable.

Reductive amination of the mixture of cis and trans isomers of the compound of the formula V from the above step with sodium cyanoborohydride or sodium triacetoxyborohydride and a compound of the formula $R^3CHO$ yields a mixture of the cis and trans isomers of a compound of the formula VI. This reaction is typically carried out in a polar solvent such as acetic acid or a lower alkanol, at a temperature from about 0° C. to about 50° C. Methanol is the preferred solvent and about 25° C. is the preferred temperature. It is also preferable that the pH of the reaction mixture be about 4 to about 5. The cis and trans isomers of the compound of the formula VI so formed can be easily separated by using silica-gel flash chromatography, eluting with 3% methanol in methylene chloride.

Reduction of either the cis or trans isomer of the compound of formula VI, or a mixture thereof, yields a compound of the formula IA having the same stereochemistry. Suitable reducing agents include borane dimethylsulfide in tetrahydrofuran ("THF"), lithium aluminum hydride, borane in THF and sodium borohydride-titanium (IV) chloride. Best results are obtained by using borane dimethylsulfide in THF. The reaction may be carried out at temperatures from about room temperature to about 150° C., and is preferably carried out at the reflux temperature of the solvent.

The compound of formula IA so formed may be converted to a compound of the formula IB having the same stereochemistry, as illustrated in scheme 1, by reacting it with a compound of the formula $R^6$—$(CH_2)_m$—X, wherein X is halo, wherein one of the carbon-carbon single bonds of said $(CH_2)_m$ may optionally be replaced by a carbon-carbon double bond, and wherein one of the carbons of said $(CH_2)_m$ may optionally be substituted with $R^8$. This reaction is typically carried out in the presence of a base such as triethylamine or potassium t-butoxide, in a polar solvent such as methylene chloride or dichloroethane, and at a temperature from about room temperature to about 150° C. Preferably, the reaction is carried out at the reflux temperature in methylene chloride in the presence of triethylamine.

Compounds of the formula IC may be prepared as illustrated in scheme 1 and described below. A compound of the formula VI is reacted with a compound of the formula $R^1X$, wherein X is halo, to yield a compound of the formula VII having the same stereochemistry (e.g. cis, trans or a mixture thereof). This reaction is typically carried out in the presence of a base such as triethylamine or potassium t-butoxide in a polar solvent such as methylene chloride or dichloroethane, at a temperature from about room temperature to about 150° C. Preferably, the reaction is carried out at about the reflux temperature in methylene choride in the presence of triethylamine.

Reduction of the compound of formula VII so formed yields a compound of the formula IC having the same stereochemistry. Examples of suitable reducing agents are lithium aluminum-hydride, borane dimethylsulfide in THF, borane in THF and sodium borohydride-titanium (IV) chloride. Best results are obtained using borane dimethylsulfide in THF. The reaction may be carried out at temperatures from about room temperature to about 150° C., and is preferably carried out at the reflux temperature of the solvent.

Scheme 2 illustrates an alternate method of preparing compounds of the formula IB. The starting material for this method is a compound of the formula VI, which is illustrated in scheme 1. In the first step of this method, the basic nitrogen of the starting material is protected with a group such as t-butoxycarbonyl (Boc), trifluoroacetyl, carbobenzyloxy or carboethoxy, by reacting it, respectively, with di-t-butyl dicarbonate, trifluoroacetic anhydride, benzyl chloroformate or ethylchloroformate. The preferred protecting group, t-butoxycarbonyl, is illustrated in scheme 2. The reaction of the starting material with di-t-butyl dicarbonate is typically carried out in a polar solvent such as THF, dichloromethane or chloroform, at a temperature from about 0° C. to about 100° C. The preferred solvent is dichloromethane and the preferred temperature is room temperature. The reaction is generally carried out for about 0.5 to 72 hours. This reaction yields a compound of the formula VIII having the same stereo- chemistry as the starting material.

The compound of formula VIII so formed is then reacted with a compound of the formula $X-(CH_2)_m-R^6$ wherein X is halo, or $CH_3SO_2O-(CH_2)_m-R^6$, to form a compound of the formula IX having the same stereochemistry. In each of $X-(CH_2)_m-R^6$ and $CH_3SO_2O-(CH_2)_m-R^6$, one of the carbons of said $(CH_2)_m$ may optionally be substituted with $R^8$ and one of the carbon-carbon single bonds of said $(CH_2)_m$ may optionally be replaced with a carbon-carbon double bond or a carbon-carbon triple bond. This reaction is generally carried out in the presence of a base such as potassium hydroxide, potassium t-butoxide, lithium diisopropylamine or sodium methoxide, in a polar solvent such as t-butanol or DMF, for about 0.5 to about 24 hours. The preferred base is potassium t-butoxide and the preferred solvent is t-butanol. Reaction temperatures will generally range from about −25° C. to about 150° C. The preferred temperature is generally the reflux temperature of the solvent.

The protecting group is then removed from the compound of formula IX by reacting it with an acid such as hydrochloric acid, trifluoroacetic acid or perchloric acid, to yield a compound of the formula X having the same stereochemistry. Appropriate solvents for this reaction include polar solvents such as methylene chloride, dioxane, ether or THF, preferably dioxane. The reaction is typically run at a temperature from about −10° C. to about 50° C., preferably about 25° C., for about 0.5 to about 24 hours.

Reduction of the compound of formula X so formed yields a compound of the formula IB having the same stereochemistry. This reaction is carried out in the same manner as described above in the discussion of scheme 1 for preparing compounds of the formula IA from compounds of the formula VI, and for preparing compounds of the formula IC from compounds of the formula VII. p Scheme 3 illustrates a method of preparing compounds of the formula ID. Formula ID represents compounds of the formula I wherein each of $R^1$ and $R^6$ are hydrogen, m is 0 and n is 2, 3 or 4. This group of compounds includes those of the formula IA. The method of scheme 3 can be used to prepare the pure 2S,3S enantiomer, the pure 2R,3R enantiomer, or a racemic mixture of a compound of the formula ID, depending on whether the starting material is, respectively, the R-enantiomer, the S-enantiomer, or a racemic mixture of the starting material of formula XI. Also, because formula ID includes compounds of the formula IA, the method of scheme 3can be used to prepare compounds of the formula IA wherein $R^4$ is attached to the "6" position of the nitrogen containing ring. The method of scheme 3 can also be used to prepare compounds of the formula ID wherein $R^2$ is benzhydryl.

Referring to scheme 3, compounds of the formula ID may be prepared as follows. The pure R-enantiomer, S-enantiomer or a racemic mixture of a compound of the formula XI is reacted with a nitrogen-protecting reagent such as t-butyldimethylsilyl chloride (TBDMS-Cl), t-butyldimethylsilyl triflate (TBDMS-OTf) or benzyl bromide/t-butoxide, preferably TBDMS-Cl, to form a compound of the formula XII. This reaction is typically carried out in a polar solvent such as DMF or triethylamine, preferably triethylamine, at a temperature of from about 0° to about 140° C. Room temperature is preferred.

The above reaction is followed by a stereospecific alkylation of the compound of formula XII to form the trans stereoisomer of a compound of the formula XIII. First, the compound of formula XII is reacted with lithium diethylamide in a polar solvent such as ether or THF, preferably THF, at a temperature from about −100° C. to about room temperature, preferably about −78° C. Then, a compound of the formula

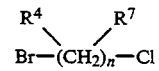

is added to the reaction mixture to produce the trans isomer of a compound of the formula XIII. Simultaneous removal of the TBDMS group and cleavage of the β-lactam using concentrated sulfuric or perchloric acid, preferably sulfuric acid, in a polar solent such as methanol or ethanol, preferably methanol, yields a compound of the formula XIV. This reaction is typically carried out at a temperature from about room temperature to about 150° C., preferably at about the reflux temperature of the solvent, for about 0.5 to about 16 hours.

The cyclization of the compound of formula XIV to produce a compound of the formula XV is accomplished by heating the crude product of formula XIV from the foregoing reaction at a temperature from about 80° C. to about 140° C., preferably at about 100° C., for about 5 minutes to about 2 days, preferably for about 15 minutes, in a high boiling solvent such as DMF or toluene, preferably in DMF. Generally, this reaction is conducted in the presence of sodium iodide and sodium bicarbonate. In the compound of formula XV produced by this reaction, $R^2$ and $-COOCH_3$ are cis to each other.

The compound of formula XV is then treated with benzylchloroformate in a polar solvent such as water, water/acetone, chloroform, dichloroethane or ethyl acetate, in the presence of a base such as triethylamine or sodium bicarbonate, to yield the N-carbobenzyloxy piperidine (N-Cbz piperidine) of formula XVI having the same stereochemistry (i.e., wherein $R^2$ and $-COOCH_3$ are in the cis configuration). This reaction may be carried out at temperatures from about 0° C. to about 100° C., preferably about 25° C., for about 5 minutes to 18 hours. Treatment of the compound of formula XVI so formed with about 5 equivalents each of trimethyl aluminum and ammonium chloride in a nonpolar solvent such as benzene or toluene for about 0.5 to about 16 hours yields a compound of the formula XVII having the same stereochemistry. Reaction temperatures may range from about room temperature to about 100° C., with about 50° C. being preferred.

The conversion of the carboxamide group of the compound of formula XVII to form a compound of the formula XVIII having the same stereochemistry may be accomplished by a Hoffmann degradation using reagents such as bromine/sodium methoxide in methanol, lead tetraacetate in t-butyl alcohol, tin (IV) chloride, iodobenzene bis(trifluoroacetate) in aqueous acetonitrile, sodium bromide or benzyltrimethyl ammonium tribromide. Preferably, the compound of formula XVII is treated with lead tetraacetate in t-butanol. This reaction is typically carried out at a temperature from about room temperature to the reflux temperature of the solvent, preferably at the reflux temperature, for about 15 minutes to about 10 hours, preferably for about 3 to about 5 hours. Reaction of the compound of formula XVIII with an acid such as hydrochloric acid, trifluroacetic acid or perchloric acid yields a compound of the formula XIX having the same stereochemistry. The solvent is typically a polar solvent such as methylene chloride, dioxane, ether or THF, preferably dioxane. This reaction is typically carried out at a temperature from about $-10°$ to about 50° C., preferably at about 25° C., for about 0.5 to 24 hours.

Reductive amination of the compound of the formula XIX from the above step with sodium cyanoborohydride or sodium triacetoxyborohydride and a compound of the formula $R^3CHO$ yields a compound of the formula XX having the same stereochemistry. This reaction is generally carried out in a polar solvent such as acetic acid or a lower alkanol, at a temperature from about 0° to about 50° C. Methanol is the preferred solvent and about 25° C. is the preferred temperature. It is also preferred that the pH of the reaction mixture be about 4 to about 5.

The compound of formula XX is converted into a compound of the formula ID wherein $R^2$ and the amino group are cis to each other by reacting it with ammonium formate in the presence of palladium on charcoal (e.g. 10% palladium on charcoal). Typically, a polar solvent such as ethyl acetate or a lower alkanol is used, and the reaction is run at a temperature from about room temperature to about 150° C. for about 0.5 to about 24 hours. Preferably, the reaction is conducted in ethanol at room temperature for about 3 to about 24 hours.

The trans isomer of a compound of the formula ID (i.e., one wherein the amino group and $R^2$ are trans to each other) may be prepared by the same procedure described above for obtaining the cis isomer, with the following modification. To prepare the trans isomer, either the compound of formula XV or the compound of formula XVI, after its formation as described above, is treated with potassium t-butoxide or a lithium dialkylamide. The solvent for this reaction is generally a polar solvent such as THF or ether, and the reaction is generally conducted at a temperature from about $-78°$ C. to room temperature, preferably at about 0° C., for about 5 minutes to about 10 hours.

An alternate method of preparing compounds of the formula ID wherein $R^2$ is benzhydryl is described in Examples 21–26.

Scheme 4 illustrates a preferred method of preparing compounds of the formula ID wherein n is 2. According to this method, a compound of the formula XXI is treated with hydrogen gas in the presence of a metal catalyst such a palladium on charcoal, platinum on charcoal or platinum dioxide, preferably palladium on charcoal, and in the presence of an acid such as trifluroacetic acid or hydrochloric acid, to produce a compound of the formula XXII. A polar inert solvent is generally used. The preferred solvent is ethanol. This reaction is typically carried out at a pressure of about 1.5 atm to about 5 atm, preferably at about 3.0 atm, at a temperature from about 0° C.–60° C., preferably at about 25° C. The compound of formula XXII so formed is then converted to a compound of the formula ID by the procedure illustrated in scheme 3 and described above.

Enantiomerically pure compounds of the formula IC (i.e., compounds of the formula ID herein $R^1$ is $(C_1-C_6)$ alkyl rather than hydrogen) may be prepared as follows. A compound of the formula XX, prepared as described above, is alkylated by reacting it with a compound of the formula $R^1X$, wherein X is halo. This reaction is usually conducted in the presence of a base such as triethylamine or potassium t-butoxide, in a polar solvent such as methylene chloride or dichloroethane, and at a temperature from about room temperature to about 200° C. Preferably, the reaction is conducted at the reflux temperature in methylene chloride in the presence of triethylamine. The alkylated product, which has the same stereochemistry as the starting material of formula XX, is then converted to a compound of the formula IC having the same stereochemistry, by reacting it with ammonium formate in the presence of palladium on charcoal (e.g. 10% palladium on charcoal). Typically, a polar solvent such as ethyl acetate or a lower alkanol is used, and the reaction is run at a temperature from about room temperature to about 80° C. for about 3 to about 24 hours. The reaction is preferably conducted in ethanol at room temperature for about 0.5 to about 24 hours.

Enantiomerically pure compounds of the formula IB may be prepared by reacting the analogous compound of the formula ID, having the same stereochemistry, with a compound of the formula $R^6-(CH_2)_m-X$, wherein X is halo or mesylate. In each of $X-(CH_2)_m-R^6$ and $CH_3SO_2O-(CH_2)_m-R^6$, one of the carbons of said $(CH_2)_m$ may optionally be substituted with $R^8$ and one of the carbon-carbon single bonds of said $(CH_2)_m$ may optionally be replaced with a carbon-carbon double bond. The reaction is performed in the same manner as described above for converting compounds of the formula IA into compounds of the formula IB.

Compounds having the formula IA wherein $R^4$, $R^5$ and $R^7$ are each hydrogen and $R^2$ is phenyl may be prepared, alternatively, by reductive amination of 3-amino-2-phenylpiperidine, using the appropriate aldehyde of the formula $R^3CHO$, as described above for converting compounds of the formula V to the corresponding compounds of the formula VI. The starting material for this reaction, 3-amino-2-phenylpiperidine, may be prepared by hydrogenolysis of 3-(2-methoxybenzylamino)-2-phenylpiperidine. The hydrogenolysis reaction is usually carried out using a catalyst such as palladium on carbon or palladium hydroxide, in an inert solvent such as acetic acid or an alcoholic solvent, at a temperature from about 0° C. to about 50° C. It is preferably carrier out at about room temperature in a methanol/ethanol solvent. It is also preferable to conduct this reaction in the presence of a mineral acid such as hydrochloric or sulfuric acid.

The above two step process for preparing compounds of the formula IA wherein $R^4$, $R^5$ and $R^7$ are each hydrogen and $R^2$ is phenyl from 3-(2-methoxybenzylamino)-2-phenylpiperidine preserves the stereochemistry at the "2" and "3" positions of the piperidine ring. It therefore may be used to produce either pure enantiomer or a racemic mixture of the product of formula IA from a sample of 3-(2-methoxybenzylamino)-2-phenylpiperidine having the same stereochemistry. Similarly, the first step of the above process may be used to produce either pure enantiomer or a racemic mixture of 3-amino-2-phenylpiperidine.

An alterative method of preparing racemic 3-amino-2-phenylpiperidine is by reducing 3-amino-2-phenylpyridine. This reduction is generally accomplished using either sodium in alcohol, lithium aluminum hydride/aluminum trichloride, electrolytic reduction or hydrogen in the presence of a metal catalyst. The reduction with sodium is generally conducted in a boiling alcohol, preferably butanol, at a temperature from about 20° C. to about the reflux temperature of the solvent, preferably at about 120° C. The reduction with lithium aluminum hydride/aluminum trichloride is usually carried out in ether, THF or dimethoxyethane, preferably ether, at a temperature from about 25° C. to about 100° C., preferably at about room temperature. The electrolytic reduction is conducted, preferably, at room temperature, but temperatures from about 10° C. to about 60° C. are also suitable.

Hydrogenation in the presence of a metal catalyst is the preferred method of reduction. Suitable hydrogenation catalyst include palladium, platinum, nickel and rhodium. The preferred catalyst for hydrogenation is platinum oxide. The reaction temperature may range from about 10° C. to about 50° C., with about 25° C. being preferred. The hydrogenation is generally carried out at a pressure from about 1.5 to about 4 atmospheres, preferably at about 3.0 atmospheres.

Compounds of the formula IA wherein $R^4$, $R^5$ and $R^7$ are each hydrogen and $R^2$ phenyl may also be prepared by the following method. According to this method, 3-amino-2-phenylpyridine is first converted into the pyridine analog of the desired piperidine of the formula IA by reacting it with the appropriate compound of the formula $R^3CHO$ or $R^3CH_2X$ wherein X is a leaving group (e.g. chloro, bromo, iodo, mesylate or tosylate).

The reaction of 3-amino-2-phenylpyridine with a compound of the formula $R^3CHO$ to produce the pyridine analog of the piperidine of formula IA is typically carried out in the presence of a reducing agent such as sodium cyanoborohydride, sodium triacetoxyborohydride, sodium borohydride, hydrogen and a metal catalyst, zinc and hydrochloric acid, or formic acid at a temperature from about −60° C. to about 50° C. Suitable reaction inert solvents for this reaction include lower alcohols (e.g., methanol, ethanol and isopropanol), acetic acid and THF. Preferably, the solvent is methanol, the temperature is about 25° C., and the reducing agent is sodium cyanoborohydride.

Alternatively, the reaction of 3-amino-2-phenylpyridine with a compound of the formula $R^3CHO$ may be carried out in the presence of a drying agent or using an apparatus designed to remove azeotropically the water generated, to produce an imine of the formula

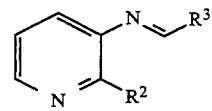

which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane and molecular sieves/THF. Titanium tetrachloride/dichloromethane is preferred.

The reaction of 3-amino-2-phenylpyridine with a compound of the formula $R^3CH_2X$ is typically carried out in a reaction inert solvent such as dichloromethane or THF, preferably dichloromethane, at a temperature from about 0° C. to about 60° C., preferably at about 25° C.

The pyridine so formed is then reduced to form the desired piperidine of formula IA by the procedure described above for reducing 3-amino-2-phenylpyridine.

Compounds of the formula IB may be prepared, in addition to the method illustrated in scheme 1 and described above, from other compounds of the formula IB by modifying the $R^6$ and $R^8$ containing side chain. The appropriate modifications may be accomplished using methods well known to those skilled in the art. Some of these modifications are described in Examples 93–104.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of Formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists is determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at $30,000 \times G$ for a period of 20 minutes. The pellet is resuspended in 50 volumes of Tris buffer, rehomogenized and then recentrifuged at $30,000 \times G$ for another twenty- minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 μg/ml of leupeptin, 2 μg of chymostatin and 200 g/ml of bovine serum albumin. This step completes the production of the tissue preparation.

The radioligand binding procedure is then carried out in the following manner, viz., by initiating the reaction via the addition of 100 μl of the test compound made up to a concentration of 1 μM, followed by the addition of 100 μl of radioactive ligand made up to a final concentration 0.5 mM and then finally by the addition of 800 μl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

Cis-3-(2-methoxybenzylamino)-2-phenylpiperidine

A. 2-Oxo-5-oximino-6-phenylpiperidine

To a stirred solution of trans-5-nitro-2-oxo-6-phenylpiperidine (27.0 gms, 122.6 mmole) in 1:1 methylene chloride:methanol was added potassium tert. butoxide (135 mmole, 15.1 gms) at 25° C. This reaction mixture was cooled to −78° C. and ozone gas was bubbled until (3 hrs) TLC (10% methanol in methylene chloride) indicated no starting material. The reaction mixture was then purged with nitrogen to remove excess ozone, and was then treated with dimethyl sulfide (60 ml) at −78° C. After warming to room temperature in 30 min., it was treated with an aqueous solution of hydroxylamine (85.2 gms, 1.22 mole) and sodium acetate (50.3 gms, 613 mmole) in water (220 ml). After stirring for 16 hrs, the volatile material was removed using a rotary evaporator. The residue was poured into 1.2 liters of cold water and stirred for 30 min. The precipitated solid was filtered to give 2-oxo-3-oxamino-6-phenylpiperidine (14.0 gms, 56.0%). M.p. 178° C.

$^1$H NMR (DMSO-$d_6$, 300 MHz, δ): 2.04–2.22 (2H, m); 2.4–2.42 (1H, m), 2.71 (1H, dt, J=8, 16 Hz); 5.02 (1H, d, J=4 Hz), 7.28–7.41 (5H, m); 8.35 (1H, d, J=4 Hz); 10.99 (1H, s).

TLC: (90:10—methylene chloride:methanol) $R_f$=0.54.

B. Cis-5-(2-methoxybenzylamino)-2-oxo-6-phenylpiperidine

2-Oxo-5-oximino-6-phenylpiperidine (28.2 gms, 138 mmole) was dissolved (heating on steam bath is necessary to achieve a clear solution) in ethanol (500 ml) containing methanol (50 ml). Neutral Raney Ni (80 gms) was added and the mixture was shaken on a Parr shaker under hydrogen (40 psi). After 18 hrs, the reaction mixture was filtered through diatomaceous earth (Celite (Trademark)) which was thoroughly washed with methanol. The organic solvents were removed using a rotary evaporator to afford an oil which solidified on standing (26.2 gms, 100%). $^1$H-NMR indicated it to be a 3:1 mixture of cis-5-amino-2-oxo-6-phenylpiperidine and trans-5-amino-2-oxo-6-phenylpiperidine, respectively. This mixture was dissolved in methanol (345 ml) and the pH was adjusted to 5 with saturated methanolic hydrochloric acid. Four Å sieves (55 gms), sodium cyanoborohydride (138 mmole) and o-methoxybenzaldehyde (22.5 gms, 165 mmole) were added to the system. Stirring was continued (4 hours) until the reaction was complete as indicated by TLC. The reaction mixture was filtered through diatomaceous earth (Celite (trademark)) and the filtrate was concentrated using a rotary evaporator. The residue was suspended in water and the pH made basic. The aqueous phase was extracted with methylene chloride (4×200 ml) washed with water, brine, and then dried (anhyd. magnesium sulfate) and concentrated to give an oil (47.0 gms) which was flash chromatographed. Elution with 3% methanol in methylene chloride afforded a white solid (19.6 gms, m.p. 122° C.).

$^1$H NMR (CDCl$_3$) δ 1.81–1.96 (1H, m); 2.0–2.18 (1H, m); 2.4 (1H, dt, J=4.5, 16 Hz); 2.75 (1H, ddd, J=6.5, 10.5 16 Hz); 3.48 (3H, s); 3.54 (1H, dd, J=13.8 Hz); 3.76 (1H, dd, J=13.8 Hz); 4.72 (1H, d, J=4 Hz); 5.72 (1H, bs); 6.71 (1H, d, J=8 Hz); 6.8 (1H, t, J=6.8 Hz); 7.04 (1H, dd, J=1.8, 7.2 Hz); 7.17 (1H, dt, J=1.6, 8.2 Hz); 7.2–7.44 (5H, m).

HRMS: Calculated for $C_{19}H_{22}N_2O_2$: 310.1682. Found: 310.1649.

TLC: (90:10 - methylene chloride:methanol) $R_f$=0.47.

C. Cis-3-(2-methoxybenzylamino)-2-phenylpiperidine

Borane dimethylsulfide in tetrahydrofuran (2M, 158 ml, 315 mmole) was added to a solution of cis-5-(2-methoxybenzylamino)-2-oxo-6-phenylpiperidine (19.6 g, 63.0 mmole) in tetrahydrofuran (500 ml) under nitrogen and the reaction mixture was heated at reflux for 18 hours. At the end of this period, the reaction mixture was cooled and the excess borane dimethylsulfide was cautiously decomposed by dropwise addition of methanol. The contents of the reaction mixture were then concentrated under vacuum. Ethanol (500 ml) and powdered potassium carbonate (17.5 g, 126 mmole) were added to the residue and the reaction mixture was heated at reflux (18 hours). Then the reaction mixture was concentrated under vacuum and the residue was extracted with methylene chloride (4×250 ml) and dried (anhydrous magnesium sulfate). The organic solvents were removed under vacuum to afford a residue which was dissolved in a minimum amount of methylene chloride. To this solution was added excess hydrochloric acid/ether, thus precipitating the dihydrochloride salt of cis-3-(2-methoxybenzylamino)-2-phenylpiperidine, which was isolated by filtration. This was heated at reflux in chloroform (400 ml) for 3 hours and filtered to give the essentially pure hydrochloride salt of the title compound (22.4 gms, m.p. 245° C., 96%), which was crystallized from a mixture of hot methanol-ethanol to afford a white crystalline solid (19.2 gms, 83%).

M.p. 255° C. (HCl salt). $^1$H NMR (CDCl$_3$, free base) δ 7.1–7.3 (6H, m); 6.97 (1H, dd, J=1.7, 7.4 Hz); 6.79 (1H, bt, J=7.4 Hz); 6.66 (1H, d, J=8.2 Hz); 3.87 (1H, d, J =2.3 Hz); 3.67 (1H, d, J=11.4 Hz): 3.44 (3H, s); 3.4 (1H, d, J=14 Hz); 3.22–3.3 (1H, bd, J=12.2 Hz); 2.72–2.86 (2H, m); 2.09–2.19 (1H, bd, J=13.7 Hz); 1.84–2.01 (1H, dt, J=4.0, 13.0 Hz); 1.53–1.7 (1H, dt, J =3.5, 13.4 Hz); 1.33–1.45 (1H, bd, J=12.5 Hz). $^{13}$C-NMR (CDCl$_3$, free base) δ 157.6, 142.5, 129.6, 128.3, 128.2, 127.8, 126.5, 126.3, 120.0, 109.8, 64.0, 54.8, 54.7, 47.8, 46.7, 28.2, 20.4. HRMS Calcd, for C$_{19}$H$_{24}$N$_2$O: 296.1886. Found: 296.1904.

TLC: (90:10 - methylene chloride:methanol) R$_f$=0.39.

EXAMPLE 2

Cis-1-allyl-3-(2-methoxybenzylamino)-2-phenylpiperidine

Under a nitrogen atmosphere, in a round-bottom flask, were placed 60 mg (0.2 mmol) of the title compound of Example 1 and 0.2 ml of methylene chloride. To this system were added 28 μl (0.2 mmol) of triethylamine and 17.5 μl (0.2 mmol) of allyl bromide, and the reaction mixture was stirred at room temperature overnight. The mixture was partitioned between methylene chloride and saturated aqueous sodium bicarbonate, the layers were separated, and the aqueous phase was extracted with three portions of methylene chloride. The combined organic fractions were dried (sodium sulfate) and concentrated with a rotary evaporator. The crude material was purified by flash column chromatography to obtain 26 mg of the title compound.

$^1$H NMR (CDCl$_3$) δ 7.20 (m, 5H), 7.03 (t, 1H, J=6 Hz), 6.79 (d, 1H, J=6Hz), 6.88 (t, 1H, J=6 Hz), 6.57 (d, 1H, J=6 Hz), 5.78 (m, 1H), 4.94 (m, 2H), 3.62 (d, 1H, J =12 Hz), 3.40 (s, 3H), 3.32 (d, 1H, J=12 Hz), 3.26 (d, 1H, J=2 Hz), 3.18 (m, 1H), 2.56 (m, 1H), 2.36 (m, 1H), 1.98 (m, 3H), 1.68 (m, 1H), 1.38 (m, 2H).

HRMS: Calcd for C$_{22}$H$_{28}$N$_2$O: 336.2202. Found: 336.2216.

EXAMPLE 3

Cis-1-ethyl-3(2-methoxybenzylamino)-2-phenylpiperidine

A.
Cis-5-(N-tert-butoxycarbonyl-2-methoxybenzylamino)-2-oxo-6-phenylpiperidine

Under a nitrogen atmosphere in a round-bottom flask were placed 2.0 g (6.4 mmol) of cis-5-(2-methoxybenzylamino)-2-oxo-6-phenylpiperidine, 7 mL of methylene chloride and 14.1 g (64.5 mmol) of di-tert-butyldicarbonate. The reaction mixture was stirred at room temperature for 4 days, poured into saturated aqueous sodium bicarbonate and extracted with two portions of methylene chloride. The combined organic fractions were washed with H$_2$O, dried (sodium sulfate) and concentrated with a rotary evaporator to obtain 16 g of oil. The crude material was purified by flash column chromatography to obtain 2.4 g (91% yield) of cis-5-(N-tert-butoxycarbonyl-2-methoxybenzylamino)-2-oxo-6-phenylpiperidine as a white solid.

$^1$H NMR (CDCl$_3$) δ 7.34 (m, 3H), 7.14 (m, 2H), 7.04 (m, 1H), 6.92 (d, 1H, J=7Hz), 6.79 (t, 1H, J=7 Hz), 6.62 (d, 1H, J=7 Hz), 5.00, 4.86 (2m, 1H), 4.68, 4.46 (2m, 1H), 4.00, 3.78 (2d, 1H, J=18 Hz), 3.58 (s, 3H), 2.82 (d, 1H, J=18 Hz), 2.20 (m, 2H), 1.80 (m, 1H), 1.44 (m, 1H), 1.53, 1.36 (2s, 3H).

B.
Cis-N-ethyl-5-(2-methoxybenzylamino)-2-oxo-6-phenylpiperidine

Under a nitrogen atmosphere in a round-bottom flask were placed 50 ml (0.12 mmol) of cis-5-(N-tert-butoxycarbonyl-2-methoxybenzylamino)-2-oxo-6-phenylpiperidine and 0.2 mL of THF. To the system were added 13.5 mg (0.12 mmol) of potassium tert-butoxide and 20 μL (0.24 mmol) of ethyl iodide. The reaction mixture was stirred at room temperature for 3 hours (during this period, additional potassium tert-butoxide (13.5 mg) and ethyl iodide (20 μL) were added to the system). The mixture was partitioned between methylene chloride and aqueous sodium bicarbonate, the layers were separated and the aqueous phase was extracted with three portions of methylene chloride. The combined organic fractions were dried (sodium sulfate) and concentrated with a rotary evaporator. The crude material was purified by flash column chromatography using 3:97 methanol/chloroform as the eluant to obtain 42 mg of cis-N-ethyl-5-(2-methoxybenzylamino)-2-oxo-6-phenylpiperidine.

$^1$H NMR (CDCl$_3$) δ 7.36 (m, 3H), 7.10 (m, 3H), 6.92 (d, 1H, J=6 Hz), 6.80 (t, 1H, J=6 Hz), 6.63 (d, 1H, J=Hz), 4.97, 4.82 (2m, 1H), 4.60, 4.40 (2m, 1H), 4.00 (m, 1H), 3.80 (m, 1H, J=18 Hz), 3.58 (s, 3H), 2.80 (d, 1H, J=18 Hz), 2.50 (m, 3H), 1.80 (m, 1H), 1.56, 1.38 (2s, 9H), 1.06 (t, 3H, J=7 Hz). Mass spectrum m/e 438 (parent).

C.
Cis-1-ethyl-3-(2-methoxybenzylamino)-2-oxo-6-phenylpiperidine.

In a round bottom flask were placed 173 mg (0.39 mmol) of cis-N-ethyl-5-(N-tert-butoxycarbonyl-2-methoxybenzylamino)-2-oxo-6-phenylpiperidine and 0.5 mL of dioxane. To this system were added 5 mL of dioxane saturated with hydrogen chloride. The reaction mixture was stirred at room temperature for 2.5 hours and concentrated with a rotary evaporator. The residue was partitioned between saturated aqueous sodium bicarbonate and chloroform and extracted with three portions of chloroform.

The combined organic fractions were dried (sodium sulfate) and concentrated to obtain 84 mg of cis-1-ethyl-3-(2-methoxybenzylamino)-2-oxo-6-phenylpiperidine, which was used immediately without further purifiction;

$^1$H NMR (CDCl$_3$) δ 7.28 (m, 7H), 6.90 (t, 1H, J=6 Hz), 6.81 (d, 1H, J=6 Hz), 4.68 (d, 1H, J=2 Hz), 3.88 (m, 3H), 3.74 (s, 3H), 3.14 (m, 1H), 2.56 (m, 3H), 1.76 (m, 1H), 1.54 (m, 1H), 1.04 (t, 3H, J=6 Hz).

D.
Cis-1-Ethyl-3-(2-methoxybenzylamino)-2-phenylpiperidine

Under a nitrogen atmosphere, in a round-bottom flask were placed 80 mg (0.24 mmol) of the amine prepared above and 5 mL of THF. To this system was added 0.59 mL (1.18 mmol) of 2.0M borane methylsulfide in THF, and the reaction mixture was heated overnight at 60° C. The mixture was cooled, ca. 2 mL of methanol was added carefully to the system, and the mixture was stirred for 1 hour and concentrated with a rotary evaporator. Sixty-six mg (0.48 mmol) of potassium carbonate in 2 mL of ethanol was added to the system, and the mixture was heated at reflux for 2.5 hours, cooled and concentrated. The residue was partitioned between water and methylene chloride, the layers were separated and the aqueous phase was extracted with three portions of dichloromethane. The combined organic fractions were dried (sodium sulfate) and concentrated to obtain 64 mg of a yellow oil. This oil was dissolved in methylene chloride, and then ether saturated with hydrogen chloride was added to the solution. The resulting yellow solid was collected, affording 60 mg of the hydrochloride salt of the title compound.

$^1$H NMR (free base, CDCl$_3$) δ 7.22 (m, 5H), 7.03 (t, 1H, J=6 Hz), 6.78 (d, 1H, J=6 Hz), 6.68 (t, 1H, J=6 Hz), 6.56 (d, 1H, J=6 Hz), 3.62 (d, 1H, J=12 Hz), 3.39 (s, 3H), 3.31 (d, 1H, J=12 Hz), 3.25 (d, 1H, J=2 Hz), 3.16 (m, 1H), 2.55 (m, 2H), 1.99 (m, 2H), 1.86 (m, 2H), 1.40 (m, 2H), 0.90 (t, 3H, J=6 Hz). HRMS Calc'd. for C$_{21}$H$_{28}$N$_2$O: 324.2201. Found: 324.2193.

The title compounds of Examples 4–14 were prepared by a procedure similar to that described in Example 2.

EXAMPLE 4

Cis-3-(2-methoxybenzylamino)-2-phenyl-1-(prop-1-yl)piperidine

M.p. 223°–225° C. $^1$H NMR (CDCl$_3$) δ 7.28 (m, 5H), 7.10 (t, 1H, J=6 Hz), 6.87 (d, 1H, J=6 Hz), 6.74 (t, 1H, J=6 Hz), 6.60 (d, 1H, J=6 Hz), 3.86 (d, 1H, J=12 Hz), 3.46 (d, 1H, J=12 Hz), 3.40 (s, 3H), 3.29 (m, 1H), 2.64 (m, 1H), 2.50 (m, 1H), 2.02 (m, 4H), 1.46 (m, 4H), 0.72 (t, 3H, J=7 Hz). Mass spectrum m/e 338 (parent).

EXAMPLE 5

Cis-1-butyl-3-(2-methoxybenzylamino)-2-phenylpiperidine

M.p. 139°–140° C. (HCl salt). $^1$H NMR (CDCl$_3$) δ 7.20 (m, 5H), 7.02 (t, 1H, J=6 Hz), 6.77 (d, 1H, J=6 Hz), 6.66 (t, 1H, J=6 Hz), 6.55 (d, 1H, J=6 Hz), 3.60 (d, 1H, J=14 Hz), 3.37 (s, 1H), 3.30 (d, 1H, J=14 Hz), 3.22 (d, 1H, J=2 Hz), 3.16 (m, 1H), 2.48 (m, 2H), 1.98 (m, 3H), 1.36 (m, 3H), 1.08 (m, 3H), 0.71 (t, 3H, J=9 Hz). Mass spectrum m/e 352 (parent).

EXAMPLE 6

Cis-3-(2-methoxybenzylamino)-2-phenyl-1-(2-phenyleth-1-yl)piperidine $^1$H NMR (CDCl$_3$) δ 7.18 (m, 10H), 6.92 (d, 1H, J=6 Hz), 6.82 (d, 1H, J=6 Hz), 6.71 (t, 1H, J=6 Hz), 6.00 (d, 1H, J=6 Hz), 3.66 (d, 1H, J=15 Hz), 3.44 (s, 3H), 3.35 (m, 2H), 2.72 (m, 3H), 2.60 (m, 1H), 2.12 (m, 4H), 1.68 (m, 1H), 1.44 (m, 2H). HRMS Calc'd for C$_{27}$H$_{32}$N$_2$O: 400.2515. Found: 400.2521.

EXAMPLE 7

Cis-3-(2-methoxybenzylamino)-2-phenyl-1-propargylpiperidine

M.p. 147°–149° C. (HCl salt, dec). $^1$H NMR (CDCl$_3$) δ 7.22 (m, 5H), 7.02 (t, 1H, J=7 Hz), 6.82 (d, 1H, J=7 Hz), 6.68 (t, 1H, J=7 Hz), 6.56 (d, 1H, J=7 Hz), 3.62 (d, 1H, J=12 Hz), 3.47 (d, 1H, J=2 Hz), 3.38 (m, 4H), 3.30 (d, 1H, J=12 (Hz), 3.21 (d, 1H, J=2 Hz), 3.15 (d, 1H, J=2 Hz), 2.94 (m, 1H), 2.55 (m, 2H), 2.06 (m, 3H), 1.40 (m, 1H). Mass spectrum m/e 334 (parent). Calc'd for C$_{22}$H$_{26}$OH$_2$ 2HCl2.75 H$_2$O: C, 57.83; H, 7.39; N, 6.13. Found: C, 57.81; H, 7.58; N, 5.91.

EXAMPLE 8

Cis-3-(2-Methoxybenzylamino)-2-phenyl-1-(3-phenylprop-1-yl)piperidine

M.p. 120°–125° C. (HCl salt, dec). $^1$H NMR (CDCl$_3$) δ 7.14 (m, 1H), 6.80 (d, 1H, J=6 Hz), 6.68 (t, 1H, J=6 Hz), 6.58 (d, 1H, J=8 Hz), 3.62 (d, 1H, J=14 Hz), 3.40 (s, 3H), 3.32 (d, 1H, J=14 Hz), 3.26 (d, 1H, J=2 Hz), 3.18 (m, 1H), 2.52 (m, 2H), 2.35 (m, 1H), 2.00 (m, 3H), 1.76 (m, 4H), 1.42 (m, 2H). Mass spectrum m/e 414 (parent). Calc'd for C$_{28}$H$_{34}$ON$_2$ 2HCl2.75H$_2$O: C, 62.62; H, 7.79; N, 5.22. Found: C, 62.63; H, 7.82; N, 5.08.

EXAMPLE 9

Cis-1-(carboxamidomethyl)-3-(2-methoxybenzylamino)-2-phenylpiperidine

M.p. 235° C. (HCl salt). $^1$H NMR (CDCl$_3$) δ 7.20 (m, 5H), 7.05 (t, 1H, J=7 Hz), 6.82 (d, 1H, J=7 Hz), 6.68 (t, 1H, J=7 Hz), 6.56 (d, 1H, J=7 Hz), 3.64 (d, 1H, J=16 Hz), 3.39 (d, 1H, J=2 Hz), 3.30 (s, 3H), 3.29 (d, 1H, J=16 Hz), 3.20 (d, 1H, J=18 Hz), 3.06 (m, 1H), 2.57 (m, 1H), 2.36 (d, 1H, J=18 Hz), 2.06 (m, 3H), 1.41 (m, 2H). Mass spectrum m/e 353 (parent).

EXAMPLE 10

Cis-1-Carboxymethyl-3-(2-methoxybenzylamino)-2-phenylpiperidine

M.p. 58° C. (HCl salt, very hygroscopic). $^1$H NMR (CD$_3$OD) δ 7.72 (m, 2H), 7.62 (m, 3H), 7.36 (t, 1H, J=7 Hz), 7.28 (d, 1H, J=7 Hz), 6.96 (m, 2H), 5.14 (m, 1H), 4.18 (m, 2H), 4.00 (m, 1H), 3.66 (m, 3H), 3.40 (m, 1H), 2.34 (m, 5H), 2.07 (m, 1H). Mass spectrum m/e 354 (parent).

EXAMPLE 11

Cis-3-(2-Methoxybenzylamino)-2-phenyl-1-(5-phenylpent-1-yl)piperidine

M.p. 109° C. (HCl salt, dec). $^1$H NMR (CDCl$_3$) δ 7.14 (m, 11H, 6.78 (d, 1H, J=6 Hz), 6.68 (t, 1H, J=6 Hz), 6.56 (d, 1H, J=6 Hz), 3.62 (d, 1H, J=14 Hz), 3.40 (s, 3H), 3.32 (d, 1H, J=14 Hz), 3.24 (d, 1H, J=2 Hz), 3.16 (m, 1H), 2.50 (m, 4H), 2.00 (m, 4H), 1.76 (m, 1H), 1.42 (m, 5H), 1.14 (m, 2H). Mass spectrum m/e 442 (parent).

EXAMPLE 12

Cis(2-Methoxybenzylamino)-2-phenyl-1-(4-phenylbut-1-yl)piperidine

M.p. 65°–70° C. (HCl salt). $^1$H NMR (CDCl$_3$) δ 7.20 (m, 11H), 6.84 (d, 1H, J=7 Hz), 6.73 (t, 1H, J=7 Hz), 6.62 (d, 1H, J=7 Hz), 3.68 (d, 1H, J=12 Hz), 3.44 (s, 3H), 3.38 (d, 1H, J=12 Hz), 3.30 (d, 1H, J=3 Hz), 3.18

(m, 1H), 2.34 (m, 4H), 2.02 (m, 3H), 1.80 (m, 1H), 1.47 (m, 6H). Mass spectrum m/e 428 (parent).

EXAMPLE 13

Cis-3-(2-Methoxybenzylamino)-2-phenyl-1-(3-phenyl-prop-2-ene-1yl)piperidine

M.p. 54°–58° C. (HCl salt, dec). $^1$H NMR (CDCl$_3$) δ 7.20 (m, 11H), 6.84 (d, 1H, J=6 Hz), 6.72 (t, 1H, J=6 Hz), 6.60 (d, 1H, J=6 Hz), 6.28 (m, 2H), 3.76 (d, 1H, J=12 Hz), 3.40 (m, 5H), 3.20 (m, 1H), 2.56 (m, 2H), 2.04 (m, 4H), 1.44 (m, 1H). Mass spectrum m/e 412 (parent).

EXAMPLE 14

Cis-3-(2-Methoxybenzylamino)-1-(2-phenoxyeth-1-yl)-2-phenylpiperidine $^1$H NMR (CDCl$_3$) δ 7.26 (m, 7H), 7.08 (t, 1H, J=6 Hz), 6.80 (m, 5H), 6.61 (d, 1H, J=6 Hz), 4.04 (m, 1H), 3.68 (d, 1H, J=14 Hz), 3.42 (s, 3H), 3.37 (d, 1H, J=14 Hz), 2.97 (m, 1H), 2.60 (m, 1H), 2.28 (m, 2H), 2.06 (m, 3H), 1.47 (m, 1H), 1.26 (m, 3H). Mass spectrum m/e 323 (parent).

The title compounds of Examples 15–17 were prepared by a procedure similar to that described in Example 3.

EXAMPLE 15

Cis-3-(2-Methoxybenzylamino)-1-methyl-2-phenyl-piperidine

M.p. 58° C. (HCl salt, very hygroscopic, dec). $^1$H NMR (CDCl$_3$) δ 7.22 (m, 5H), 7.04 (t, 1H, J=6 Hz), 6.82 (d, 1H, J=6 Hz), 6.78 (t, 1H, J=6 Hz), 6.58 (d, 1H, J=6 Hz), 3.62 (d, 1H, J=12 Hz), 3.42 (s, 3H), 3.32 (d, 1H, J=12 Hz), 3.02 (m, 2H), 2.56 (m, 1H), 2.04 (m, 3H), 2.02 (s, 3H), 2.38 (m, 2H). Mass spectrum m/e 310 (parent).

EXAMPLE 16

Cis-1-Benzyl-3-(2-Methoxybenzylamino)-2-phenyl-piperidine

M.p. 68°–70° C. (HCl salt, dec). $^1$H NMR (CDCl$_3$) δ 7.28 (m, 11H), 6.83 (d, 1H, J=6 Hz), 6.70 (t, 1H, J=6 Hz), 6.61 (d, 1H, J=6 Hz), 3.85 (d, 1H, J=14 Hz), 3.64 (d, 1H, J=14 Hz), 3.47 (s, 3H), 3.35 (m, 2H), 2.96 (m, 1H), 2.79 (d, 1H, J=14 Hz), 2.62 (m, 1H), 1.96 (m, 3H), 1.38 (m, 2H). Mass spectrum m/e 386 (parent).

EXAMPLE 17

Cis-1-(2-Hydroxyeth-1-yl)-3-(2-methoxybenzylamino)-2-phenylpiperidine

M.p. 148°–149° C. (HCl salt, dec). $^1$H NMR (CDCl$_3$) δ 7.28 (m, 5H), 7.12 (t, 1H, J=7 Hz), 6.88 (d, 1H, J=7 Hz), 6.75 (t, 1H, J=7 Hz), 6.63 (d, 1H, J=7 Hz), 3.70 (m, 3H), 3.44 (m, 5H), 3.26 (m, 1H), 2.85 (m, 1H), 2.64 (m, 1H), 2.06 (m, 3H), 1.88 (m, 1H), 1.30 (m, 2H). HRMS Calc'd for C$_{21}$H$_{28}$N$_2$O$_3$: 340.2150. Found: 340.2142. Calc'd. for C$_{21}$H$_{28}$O$_2$N$_2$ 2HCl2.6H$_2$O: C, 54.81; H, 7.71; N, 6.08. Found; C, 54.81; H, 8.02; N, 5.82.

EXAMPLE 18

Cis-3-(2-Methoxybenzylamino)-2-phenylpyrrolidine

1-Benzyl-3-carboethoxy-2-phenyl-2,3-didehydropyr-rolidine, made according to the procedure described by Celerier et al., *Tetrahedron Lett.*, 28, 6597 (1987), (2.0 g, 6.5 mmol) was dissolved in 70 mL of ethanol. To this solution was added 1 mL of concentrated aqueous hydrogen chloride and 2.0 g of 5% palladium on carbon. The mixture was placed on a Parr apparatus (40 p.s.i. hydrogen) for 1 hour. The mixture was filtered through diatomaceous earth (Celite (trademark)) and the filtrate was concentrated with a rotary evaporator. Saturated aqueous sodium bicarbonate was added to the residue until the liquid was basic (pH 8), and the material was extracted with three portions of methylene chloride. The combined organic fractions were dried (sodium sulfate) and concentrated (rotary evaporator) to obtain 1.1 g of an oil. This material was suspended in 10 mL of 10% aqueous sodium bicarbonate, and the system was cooled in an ice bath. To the system was added 0.65 mL (4.6 mmol) of benzylchloroformate, the cold bath was removed and the mixture was stirred for 30 min. Ether was then added, the layers were separated, and the ether phase was washed with water, dried (sodium sulfate) and concentrated with a rotary evaporator. The crude material was purified by flash column chromatography (80 g of silica gel) using 1:3 ethyl acetate/hexanes as the eluant to obtain 940 mg of pure 1-benzyl-3-carbo-ethoxy-2-phenylpyrrolidine. $^1$H NMR (CDCl$_3$) 7.16 (m, 9H), 6.76 (m, 1H), 5.02 (m, 3H), 3.78 (m, 3H), 3.54 (m, 1H), 3.34 (m, 1H), 2.40 (m, 1H), 2.02 (m, 1H), 1.94 (t, 3H, J=6 Hz). Mass spectrum m/e 353 (parent).

This material was converted to the title compound by a procedure similar to that described in Example 63 E-G. $^1$H NMR (CDCl$_3$) δ 7.26 (m, 5H), 7.12 (t, 1H, J=7 Hz), 6.98 (d, 1H, J=7 Hz), 6.80 (t, 1H, J=7 Hz), 6.70 (d, 1H, J=6 Hz), 4.11 (d, 1H, J=4 Hz), 3.86 (d, 1H, J=12 Hz), 3.52 (s, 3H), 3.42 (d, 1H, J=12 Hz), 3.34 (m, 1H), 3.25 (m, 1H), 2.98 (m, 1H), 1.9 (m, 2H).

EXAMPLE 19

Cis-3-(N,N-Methyl-2-methoxybenzylamino)-2-phenyl-piperidine

Under a nitrogen atmosphere in a round-bottom flask were placed 75 mg (0.24 mmol) of the lactam 5-(2-methoxybenzylamino)-2-oxo-6-phenylpiperidine, 0.036 mL (0.48 mmol) of methyl iodide, 0.066 mL (0.48 mmol) of triethylamine and 0.2 mL of THF. The reaction mixture was stirred at room temperature for 5 hours and poured into saturated aqueous sodium bicarbonate. This mixture was extracted with three portions of methylene chloride. The methylene chloride extracts were dried (sodium sulfate) and concentrated with a rotary evaporator. The residue was resubjected to the above conditions, employing the following quantities of reagents: 0.11 mL (1.4 mmol) of methyl iodide and 0.066 mL (0.48 mmol) of triethylamine. The mixture was stirred at room temperature for 7.5 hours, and during this period additional methyl iodide (0.11 mL) was added to the system. The reaction mixture was treated as described above to obtain 70 mg of a clear colorless oil. The crude material was purified by flash column chromatography (7 g of silica gel) using 3:97 methanol/chlorform as the eluant to obtain 44 mg of cis-3-(N,N-methyl-(2-methoxybenzylamino) -2-phenylpiperidin-6-one.

$^1$H NMR (CDCl$_3$) δ 1.86 (m, 5H), 2.52 (m, 1H), 2.70 (m, 1H), 3.34 (m, 1H), 3.52 (d, 1H, J=14), 3.74 (d, 1H, J=14), 3.84 (s, 3H), 4.68 (m, 1H), 6.90, (m, 2H), 7.80 (m, 7H), HRMS: Calcd. for C$_{20}$H$_{24}$N$_2$O$_2$: 324.1838. Found: 324.1884.

Under a nitrogen atmosphere in a round-bottom flask were placed 54 mg (0.17 mmol) of cis-3-(N,N-methyl-(2-methoxy)benzylamino)-2-phenylpiperidin-6-one and 2.5 mL of THF. To the system was added slowly 0.43 mL (0.86 mmol) of 2.0M borane-methylsulfide complex in THF, and the reaction mixture was heated at 60° C. overnight. The reaction mixture was cooled to room temperature, methanol was added slowly to the system and the mixture was stirred at room temperature for 30 min and concentrated with a rotary evaporator. Two milliliters of ethanol and 48 mg (0.35 mmol) of potassium carbonate were then added, and the reaction mixture was heated at reflux for 4 hours and cooled to room temperature. The solvent was removed with a rotary evaporator. The residue was partitioned between chloroform and water, the layers were separated, and the aqueous phase was extracted with chloroform. The combined organic fractions were dried (sodium sulfate) and concentrated to obtain 75 mg of an oil. This oil was dissolved in a minimum volume of methylene chloride and ether saturated with hydrogen chloride was added to the solution. Water was added to the system, and the mixture was washed with two portions of methylene chloride. The aqueous phase was basified with aqueous sodium hydroxide and extracted with four portions of methylene chloride. These combined fractions were dried and concentrated to obtain 20 mg of the title compound as an oil.

$^1$H NMR (CDCl$_3$) δ 7.62 (d, 2H, J=6 Hz), 7.22 (m, H), 7.06 (t, 1H, J=7 Hz), 6.82 (d, 1H, J=6 Hz), 6.70 (m, 2H), 4.06 (d, 1H, J=2 Hz), 3.71 (s, 3H), 3.62 (d, 1H, J=12 Hz), 3.44 (d, 1H, J=12 Hz), 3.11 (m, 1H), 2.81 (m, 2H), 2.19 (s, 3H), 1.73 (m, 4H). Mass spectrum m/e 310 (parent).

EXAMPLE 20

Cis-2,4-Diphenyl-3-(2-methoxybenzylamino)piperidine

Under a nitrogen atmosphere in a round-bottom flask equipped with a reflux condenser were placed 21.1 g (89 mmol) of ethyl 4-nitro-3-phenylbutyrate (McMurray, J. E. et. al., *Syn. Comm.*, 8, 53(1978)) and 90 mL of ethanol. To the system was added 9.04 mL (89 mmol) of benzaldehyde and 13.7 g (180 mmol) of ammonium acetate, and the reaction mixture was heated at 70° C. overnight. The reaction mixture was cooled, a small volume of ethanol was added and the suspension was filtered. The collected solid was rinsed with a small volume of ethanol followed by ether to afford 22.7 g of 4,6-diphenyl-5-nitro-2-oxopiperidine.

$^1$H NMR (DMSO) δ 2.53 (dd, 1H, J=6, 18), 2.82 (m, 1H), 3.88 (m, 1H), 4.80 (d, 1H, J=8), 5.47 (t, 1H, J=8), 7.3 (m 10H). Mass spectrum m/e 296 (parent).

In a round-bottom flask were placed 15 g (50.6 mmol) of the nitro lactam 4,6-diphenyl-5-nitro-2-oxopiperidine and 85 mL of methylene chloride. Potassium tert-butoxide (5.72 g, 50.6 mmol) was added and the mixture was stirred for 15 min. To this system was added 85 mL of methanol. The mixture was stirred for 15 min and the system was cooled to −78° C. Ozone was bubbled through the reaction mixture for 4 hours, nitrogen was bubbled through the mixture, 10 mL of dimethyl sulfide was added and nitrogen was bubbled through the mixture overnight. A mixture of water and methylene chloride was added to the system and the resulting solid (8.8 g of a mixture of the nitro lactam 4,6-diphenyl-5-nitro-2-oxopiperidine and 2,5-dioxo-4,6-diphenyl-piperidine was collected by suction filtration. The filtrate was concentrated with a rotary evaporator and the residue was partitioned between methylene chloride and water. The layers were separated, and the aqueous phase was extracted with two portions of methylene chloride. The combined organic fractions were dried (sodium sulfate) and concentrated to afford 5.14 g of crude 2,5-dioxo-4,6-diphenylpiperidine which was used immediately without further purification.

Under a nitrogen atmosphere in a round-bottom flask were placed 2,5-dioxo-4,6-diphenylpiperidine (5.14 g, 19 mmol) and 75 mL of ethanol. A solution of 3.96 g (57 mmol) of hydroxylamine hydrochloride and 7.74 g (95 mmol) of sodium acetate in 25 mL of water were added and the reaction mixture was stirred at room temperature. The reaction mixture was concentrated to ca. ½ its initial volume, and the resulting precipitate was collected by suction filtration. This precipitate (1.5 g) was washed with saturated aqueous sodium bicarbonate, water and ether to afford 722 mg of 4,6-diphenyl-5-oximino-2-oxopiperidine as a white solid.

$^1$H NMR (DMSO) δ 2.52 (m, 2H), 2.76 (m, 1H), 4.12 (m, 1H), 5.80 (m, 1H), 7.30 (m, 10H), 8.24 (m, 1H). Mass spectrum m/z=280 (parent).

To a solution of 4,6-diphenyl-5-oximino-2-oxopiperidine (700 mg, 2.5 mmol) was added ca. 2 g of wet Raney nickel which had been washed with water (until washings had a neutral pH) followed by ethanol, and the mixture was placed under an atmosphere of hydrogen (40 psi, Parr apparatus) overnight. The mixture was filtered through a pad of diatomaceous earth (Celite (trademark)), and the filter cake was rinsed well with ethanol. The filtrate was concentrated to afford 500 mg of 5-amino-4,6-diphenyl-2-oxopiperidine as a foam.

$^1$H NMR (CDCl$_3$) δ 2.96 (m, 4H), 4.12, 4.5 (m, 1H), 7.2 (m, 10H). Mass spectrum: m/z 266 (parent).

Under a nitrogen atmosphere in a round bottom flask were placed 500 mg (1.9 mmol) of 5-amino-4,6-diphenyl-2-oxopiperidine and 5 mL of methanol. To the system was added 1 g of 3 Å molecular sieves, and the pH of the mixture was adjusted to 4.5 using methanol saturated with hydrogen chloride. To this system was added 284 mg (2.1 mmol) of 2-methoxybenzaldehyde, and the mixture was stirred at room temperature overnight. The mixture was filtered through diatomaceous earth (Celite (trademark)), the filter cake was rinsed well with methanol and the filtrate was concentrated with a rotary evaporator. The residue was partitioned between saturated aqueous sodium bicarbonate and chloroform, the layers were separated and the aqueous phase was extracted with three portions of chloroform. The combined chloroform extracts were dried (sodium sulfate) and concentrated, and the residue was subjected to flash column chromatography (30 g of silica gel) using 3:97 methanol/chloroform as the eluant to obtain 115 mg of 4,6-diphenyl-5-(2-methoxybenzylamino)-2-oxopiperidine.

$^1$H NMR (CDCl$_3$) δ 2.36 (dd, 1H, J=6, 18), 2.99 (m, 2H), 3.30 (m, 1H), 3.35 (s, 3H), 3.62 (d, 1H, J=16), 3.74 (d, 1H, J=16), 4.22 (m, 1H), 6.62 (d, 1H, J=6), 6.80 (t, 1H, J=6), 6.96 (m, 3H), 7.18 (m, 10H). Mass spectrum: m/z 386 (parent).

Under a nitrogen atmosphere in a round-bottom flask were placed 115 mg (0.3 mmol) of the amine 4,6-diphenyl-5-(2-methoxybenzylamino)-2-oxopiperidine and 5 mL of THF. To the system was added 0.74 mL (1.5 mmol) of 2.0 M borane-methyl sulfide complex in THF, and the reaction mixture was heated at 60° C. overnight. The mixture was cooled to room temperature, and methanol was added carefully to the system. The mixture was stirred for 2 hours and concentrated with a rotary evaporator. To this system were added 85 mg (0.6 mmol) of potassium carbonate and ca. 3 mL of ethanol, and the mixture was heated at 85° C. for 3 hours. The mixture was cooled to room temperature, concentrated, partitioned between methylene chloride and saturated aqueous sodium bicarbonate and extracted with three portions of methylene chloride. The combined methylene chloride fractions were dried (sodium sulfate) and concentrated to obtain 109 mg of an oil. This crude material was subjected to flash column chromatography (5 g of silica gel) using 1:19 methanol/chloroform as the eluant to afford 56 mg of the title compound. The hydrochloride salt of this material was prepared by treating a methylene chloride solution of the product with ether saturated with hydrogen chloride, concentrating, triturating with ether, scratching and repeating the concentration from ether. M.P. 176°–178° C. (HCl salt, dec).

$^1$NMR (CDCl$_3$) δ 7.18 (m, 11H), 6.92 9 (d, 1H)=6 Hz), 6.76 (t, 1H, J=6 Hz), 6.61 (d, 1H, J=6 Hz), 4.01 (d, 1H, J=2 Hz), 3.66 (d, 1H, J=12 Hz), 3.53 (d, 1H, J=12 Hz), 3.38 (s, 3H), 3.30 (m, 1H), 3.12 (m, 3H), 2.12 (m, 2H). HRMS calc'd. for C$_{25}$H$_{28}$N$_2$O: 3.72.2202. Found: 372.2193.

The title compounds of Examples 21-26 have the following general formula

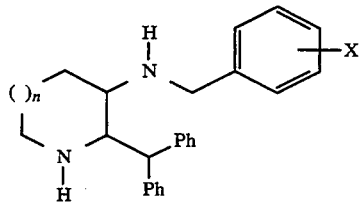

and were prepared by the following procedure.

A. Methyl 4-hydroxy-5-nitro-6,6-diphenyl hexanoate

A solution of 2,2-diphenyl-nitroethane (42.6 gm, 187 mmole) and potassium tert. butoxide (3.15 gm, 28 mmole) was stirred into a mixture of tetrahydrofuran and tert. butanol (1.5:1, 320 mL) at −78° C. and methyl 3-formyl-propionate (24.0 gm, 206 mmole) was added. The reaction mixture was then allowed to warm to 10° C. over a period of 1 hour, after which it was quenched with acetic acid (1.8 ml). The mixture was concentrated under vacuum, diluted with pH 7 butter (400 ml), and extracted with methylene chloride (3×400 ml). The combined extracts were dried (magnesium sulfate), filtered and concentrated to afford an orange oil which on trituration with ether afforded methyl 4-hydroxy-5-nitro-6,6-diphenyl hexanoate (29.94 gm). The filtrate was concentrated and flash chromatographed. Elution with 10% ethyl acetate in hexane afforded an additional 20.66 gm of methyl 4-hydroxy-5-nitro-6,6-diphenyl hexanoate. Total yield (79%).

$^1$NMR (CDCl$_3$) δ 7.2–7.4 (10H, m), 5.3 (1H, dd, J=2.5, 12 Hz), 4.9 (1H, d, J=12 Hz), 3.6 (3H, s), 2.6 (1H, m), 2.45 (2H, t, J=7 Hz), 1.7–2.0 (1H, m), 1.6–1.7 (1H, m).

B. 2-Oxo-5-hydroxy-6-benzhydrylpiperidine

To a stirred solution of methyl 4-hydroxy-5-nitro-6,6-diphenyl hexanoate (50.5 gm, 147 mmol) in ethanol (200 ml) at 25° C. was added neutral Raney nickel (50 gms). The reaction mixture was shaken on a Parr shaker under hydrogen (30 psi). After 18 hours, the reaction mixture was filtered through diatomaceous earth (Celite (trademark)) which was thoroughly washed with ethanol (400 ml) and methylene chloride (600 ml). The organic phases were combined and concentrated under vacuum to a yellow oil (40.25 gms), which on trituration with cold ether afforded 2-oxo-5-hydroxy-6-benzhydryl piperidine (18.5 gm, m.p. 208° C., 45%). Evaporation of the mother liquor afforded an oily residue upon treatment with potassium tert. butoxide in tetrahydrofuran at room temperature for 6 hours. Extraction with methylene chloride and trituration with ether afforded an additional 2.55 gms of 2-oxo-5-hydroxy-5-benzhydryl-piperidine (overall yield 51%).

IR (neat max 3380, 1649 cm$^{-1}$)

$^1$H NMR (CDCl$_3$) δ 7.17–7.4 (10H, m), 5.49 (1H, bs), 41.8 (2H, s), 3.86 (1H, bs), 2.54–2.7 (1H, m), 2.3–2.42 (1H, m), 1.8–2.08 (2H, m).

HRMS Calc'd for C$_{18}$H$_{20}$N$_2$O: 282.1495. Found: 282.1495.

C. 2,5-Dioxo-6-benzhydrylpiperidine

To a stirred solution of 2-oxo-5-hydroxy-6-benzhydryl piperidine (18.15 gm, 64.5 mmole) in acetone (150 ml) at −5° C. was added Jones reagent (2.67 M, 94 mmole), and the reaction mixture was further stirred for 4 hrs. At the end of this period, the excess reactant was decomposed with 2-propanol and the solution concentrated under vacuum to half of its volume. The contents of the flask were then dilutes with water (1000 ml) and extracted with methylene chloride (3×1000 ml). the combined organic phases were dried (anhyd. magnesium sulfate) and the methylene chloride was removed under vacuum to afford 2,5-dioxo-6-benzhydrylpiperidine (15.35 gm, 85%).

$^1$H NMR (CDCl$_3$) δ 7.18–7.4 (10H, m), 4.8 (1H, d, J=4 Hz), 4.7 (1H, dd, J=4, 1.6 Hz), 2.38–2.6 (2H, m), 2.16–2.3 (2H, m), 1.9–2.01 (1H, m).

D. 2-Oxo-5-oximino-6-benzhydrylpiperidine

To a stirred solution of 2,5-dioxo-6-benzhydrylpiperidine (15.35 gm, 55 mmole) in pyridine (150 ml) was added hydroxylamine hydrochloride (10.68 gm, 165 mmole) and the reaction mixture was stirred for 15 min. The reaction mixture was concentrated under vacuum, and the contents were poured into 1N HCl (250 ml). The aqueous phase was extracted with methylene chloride (2×300 ml) and dried (anhyd. magnesium sulfate). The methylene chloride was removed under vacuum to afford 2-oxo-5-oximino-6-benzhydrylpiperidine (10.62 gms, 65%).

$^1$NMR (CDCl$_3$) δ 7.18–7.4 (10H, m), 5.96 (1H, bd), 5.59 (1H, bs), 4.8 (1H, m), 3.8 (1H, d, J=10 Hz), 2.98–3.09 (1H, m), 2.05–2.42 (3H, m).

The title compounds of examples 21-26 were prepared from the title compound of "D" above by a procedure similar to that described in Examples 1(B) and 1(C).

EXAMPLE 21

Cis-3-benzylamino-2-benzhydrylpiperidine (X=H, n=1) M.p. 117° C. $^1$H NMR (CDCl$_3$) δ 7.04–7.4 (15H, m), 4.39 (1H, d, J=10 Hz), 3.76 (1H, d, J=12 Hz), 3.4 (1H, d, J=12 Hz), 3.28 (1H, d, J=10 Hz), 2.94 (1H, m), 2.54 (1H, m), 2.54 (1H, m), 2.0 (2H, m), 1.7 (1H, m), 1.22 (1H, m). HRMS Calc'd for C$_{25}$H$_{28}$N$_2$: 356.2253. Found: 356.2256.

EXAMPLE 22

Trans-3-benzylamino-2-benzhydrylpiperidine (X=H, n=1) M.p. 186° (HCl salt). $^1$H NMR (CDCl$_3$) δ 7.1–7.6 (15H, m), 4.57 (1H, d, J=10 Hz), 3.82 (1H, d, J=14 Hz), 3.65 (1H, d, J=14 Hz), 3.46 (1H, bt), 2.9 (1H, m), 2.5 (3H, m), 2.05 (1H, m), 1.72 (1H, m), 1.45 (1H, m). HRMS Calcd for C$_{25}$H$_{28}$N$_2$: 356.2253. Found: 356.2269.

EXAMPLE 23

Cis-3-(2-methoxybenzylamino)-2-benzhydrylpiperidine (x=2-OMe, n=1) M.p. 258° C. (dec. HCl salt). $^1$H NMR (CDCl$_3$) δ 6.7–7.4 (14H, m), 4.4 (1H, d, J=10 Hz), 3.8 (3H, s), 3.75 (2H, dd, J=12 Hz), 3.45 (1H, bd), 3.39 (1H, d, J=10 Hz), 3.0 (1H, bd), 2.62 (2H, m), 2.08 (1H, m), 1.7 (1H, m), 1.4 (1H, m), 1.2 (1H, m). HRMS Calc'd for C$_{26}$H$_{30}$N$_2$O: 386.2358. Found: 386.2358.

EXAMPLE 24

Trans-3-(2-methoxybenzylamino)-2-benzhydryl-piperidine (X=2-OMe, n=1) Oil. $^1$H NMR (CDCl$_3$) δ 6.7–7.4 (14H, m), 4.55 (1H, d, J=10 Hz), 3.8 (3H, s), 3.81 (1H, d, J=14 Hz), 3.6 (1H, d, J=14 Hz), 3.4 (1H, m), 2.9 (1H, m), 2.54 (2H, m), 2.0 (2H, m), 1.53 (1H, m), 1.45 (1H, m). HRMS Calcd for C$_{26}$H$_{30}$N$_2$O: 386.2358. Found: 386.2318.

EXAMPLE 25

Cis-3-benzylamino-2-benzhydrylazepine (X=H, n=2) M.p. 111°–112° C. $^1$H NMR (CDCl$_3$) δ 6.94–7.45 (15H, m), 4.33 (1H, d, J=10 Hz), 3.52 (1H, d, J=12 Hz), 3.34 (1H, d, J=12 Hz), 3.21 (1H, dd, J=2.1, 10 Hz), 3.16 (1H, bd), 2.4–2.58 (2H, m), 1.8 (1H, m), 1.56 (3H, m), 1.32 (2H, m).

EXAMPLE 26

Trans-3-benzylamino-2-benzhydrylazepine (X=H, n=2) M.p. 186°–187° C. (HCl salt). $^1$H NMR (CDCl$_3$) δ 7.0–7.5 (15H, m), 3.88 (1H, d, J=11 Hz), 3.45–3.6 (2H, m), 3.22 (1H), d, J=12 Hz), 3.0 (1H, d, J=12 Hz), 2.45–2.62 (2H, m), 1.75 (1H, m), 1.5 (2H, m), 1.08–1.25 (3H, m). HRMS Calcd for C$_{26}$H$_{31}$N$_2$: 371.2487. Found: 371.2495.

The title compounds of Examples 27–33 have the following general formula and were prepared by a procedure similar to that of Example 1.

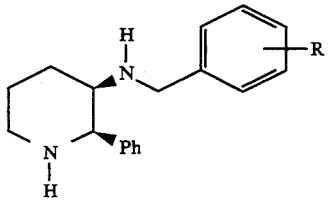

EXAMPLE 27

Cis-3-benzylamino-2-phenylpiperidine (R=H). M.p. 250° C. (HCl salt). $^1$H NMR (CDCl$_3$) δ 6.94–7.0 (10H, m), 3.89 (1H, d, J=2.3 Hz), 3.52 (1H, d, J=13 Hz), 3.32 (1H, d, J=13 Hz), 3.25 (1H, bd, J=12 Hz), 2.88 (1H, d, J=2.5 Hz), 2.78 (1H, dt, J=12, 3 Hz), 2.4 (1H, d, J=12 Hz), 1.8–1.98 (1H, m), 1.6 (1H, tt, J=12, 2.5 Hz), 1.42 (1H,) d, J=12 Hz).

EXAMPLE 28

Cis-3-(2-fluorobenzylamino)-2-phenylpiperidine (R=2-F). M.p.>260° C. (dec., HCl salt). $^1$H NMR (CDCl$_3$) δ 7.31–7.2 (5H, m), 7.15–7.07 (1H, m), 6.97–6.85 (3H, m), 3.88 (1H, d, J=3Hz), 3.64 (1H, d, J=14 Hz), 3.50 (1H, d, J=14 Hz), 3.36–3.2 (1H, m), 2.87–2.73 (2H, m), 2.07 (1H, bd, J=13 Hz), 1.88 (1H, qt, J=13, 4 Hz), 1.67–1.58 (1H, m), 1.43 (1H, bd, J=13 Hz). $^{13}$C NMR (CDCl$_3$) δ 162.6, 159.4, 142.6, 130, 129.8, 128.2, 128, 127, 127.8, 127.6, 126.8, 126.4, 123.73, 123.7, 115, 114.7, 64.3, 55.5, 47.8, 44.5, 44.4, 29.1, 29.4. HRMS Calc'd for C$_{18}$H$_{21}$N$_2$F: 284.1689. Found: 284.1701.

EXAMPLE 29

Cis-3-(2,6-difluorobenzylamino)-2-phenylpiperidine (R=2,6-di F). M.p.>260° C. (dec., HCl salt). $^1$NMR (CDCl$_3$) δ 7.33–7.02 (6H, m), 6.7 (2H, t, J=8 Hz), 3.86 (1H, d, J=2 Hz), 3.63 (1H, d, J=14 Hz), 3.52 (1H, d, J=14 Hz), 3.24 (1H, bd, J=10 Hz), 2.83–2.74 (1H, m), 2.09 (1H, bd, J=13 Hz), 1.9 (1h, qt J=14, 4 Hz), 1.63 (1H, tt, J=14, 4 Hz), 1.4 (1H, bd, J=12 Hz). $^{13}$C NMR (CDCl$_3$) δ 142.1, 128.4, 128.3, 126.7, 126, 111.1, 110.8, 110.7, 63.8, 55.2, 47.7, 38.5, 28.9, 20.4. HRMS Calc'd for: 302.1595. Found: 302.1607.

EXAMPLE 30

Cis-3-(2-methylbenzylamino)-2-phenylpiperidine (R=2-CH$_3$). M.p. 254° C. (dec., HCl salt). $^1$H NMR (CDCl$_3$) δ 7.31–7.21 (4H, m), 7.09–6.96 (4H, m), 3.9 (1H, d, J=2 Hz), 3.54 (1H, d, J=14 Hz), 3.28 (1H, d, J=14 Hz), 3.22–3.14 (1H, m), 2.91–2.87 (1H, m), 2.79 (1H, td, J=8, 4 Hz), 2.14 (1H, bd, J=9 Hz), 1.98 (3H, s), 1.97–1.75 (1H, m), 1.7–1.48 (3H, m). $^{13}$C NMR (CDCl$_3$) δ 142.7, 138.6, 136.4, 130, 128.4, 128.2, 126.7, 126.6, 125.5, 64.3, 56.2, 49.7, 29.3, 20.5, 18.5. HRMS Calc'd for C$_{19}$H$_{24}$N$_2$: 280.1939. Found: 280.1952.

EXAMPLE 31

Cis-3-(2-trifluoromethylbenzylamino)-2-phenylpiperidine (R=2-CF$_3$). M.p. 249° C. (dec., HCl salt). $^1$H NMR (CDCl$_3$) δ 7.49 (1H, d, J=8Hz), 7.49–7.16 (8H, m), 3.89 (1H, d, J=2 Hz), 3.7 (1H, d, J=15 Hz), 3.57 (1H, d, J=15 Hz), 3.25 (1H, bd, J=12 Hz), 2.86–2.74 (2H, m), 2.08 (1H, bd, J=12 Hz), 1.93–1.8 (1H, m), 1.67–1.55 (2H, m), 1.44 (1H, bd, J=14 Hz). $^{13}$C NMR (CDCl$_3$) δ 142.7, 139.8, 131.5, 129.7, 128.2, 126.8, 126.5, 126.2, 125.4, 125.4, 64.6, 56.2, 47.8, 47.0, 29, 20.5. HRMS Calc'd for C$_{19}$H$_{21}$N$_2$F$_3$: 334.1657. Found: 334.1665.

EXAMPLE 32

Cis-3-(2-chlorobenzylamino)-2-phenylpiperidine (R=2-Cl). M.p. 256° C. (dec., HCl salt). $^1$H NMR (CDCl$_3$) δ 7.31–6.97 (9H, m), 3.88 (1H, d, J=2 Hz), 3.63 (1H, d, J=15 Hz), 3.48 (1H, d, J=15 Hz), 3.25 (1H, bd, J=10 Hz), 2.87–2.74 (2H, m), 2.09 (1H, bd, J=15 Hz), 1.9 (1H, qt, J=13, 4 Hz), 1.68–1.57 (1H, m), 1.43 (1H, bd, J=13 Hz). $^{13}$C NMR (CDCl$_3$) δ 142.5, 138.1, 133.6, 129.7, 129.1, 128.3, 127.7, 126.8, 126.4, 64.3, 55.6, 48.7, 47.8, 29, 20.4 HRMS Calc'd for C$_{18}$H$_{21}$N$_2$Cl: 300.1394. Found: 300.1394.

EXAMPLE 33

Cis-3-(3-trifluoromethylbenzylamino)-2-phenylpiperidine (R=3-CF₃). M.p. 240° C. (dec., HCl salt). ¹H—NMR (CDCl₃) δ 7.41–7.14 (9H, m), 3.88 (1H, d, J=2 Hz), 3.55 (1H, d, J=14 Hz), 3.38 (1H, d, J=14 Hz), 3.22 (1H, bd, J=14 Hz), 2.84–2.74 (2H, m), 2.01 (1H, bd, J=14 Hz), 1.85 (1H, qt, J=12, 4 Hz), 1.63–1.54 (1H, m), 1.45 (1H, bd, J=13 Hz). ¹³C NMR (CDCl₃) δ 142.8, 142.1, 131.1, 128.4, 128.3, 127, 126.4, 124.5, 123.3, 123.3, 64.5, 55.8, 51, 47.7, 29.4, 20.4. HRMS Calc'd for $C_{19}H_{21}N_2F_3$: 334.1657: Found: 334.1663.

The title compounds of examples 34–55 have the following general formula and were prepared by a procedure similar to that described in Example 1.

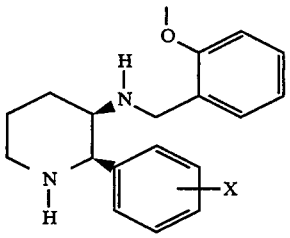

EXAMPLE 34

Cis-3-(2-methoxybenzylamino)-2-(2-fluorophenyl)-piperidine (X=2-F). M.p. 253° C. (HCl salt). ¹H NMR (CDCl₃) δ 8.03 (1H, t, J=7 Hz), 7.62–7.54 (1H, m), 7.47–7.35 (2H, m), 7.27–7.19 (2H, m), 6.94 (2H, dd, J=9, 2 Hz), 5.25 (1H, d, J=4 Hz), 5.25 (1H, d, J=13 Hz), 4.03–4.00 (1H, m), 3.87 (1H, d, J=13 Hz), 3.75 (3H, s), 3.67 (1H, bd J=13 Hz), 3.42–3.37 (2H, m), 2.6–2.42 (2H,) m), 2.38–2.3 (1H, m), 2.08–1.96 (1H, m). HRMS Calcd for $C_{19}H_{23}N_2OF$: 314.1795. Found: 314.1778.

EXAMPLE 35

Cis-3-(2-methoxybenzylamino)-2-(2-chlorophenyl)-piperidine (X=2-Cl). M.p. 264° C. (HCl salt). ¹NMR (CDCl₃) δ 8.15 (1H, d, J=6 Hz), 7.66–7.5 (1H, m), 7.39 (1H, t, J=8 Hz), 7.15 (1H, d, J=6 Hz), 6.94 (2H, t, J=8 Hz), 5.21 (1H, d, J=3 Hz), 4.19–4.1 (2H, m), 3.27 (1H, d, J=12 Hz), 3.78 (3H, s), 3.76–3.64 (1H, m), 3.52–3.4 (1H, m), 2.64–2.44 (2H, m), 2.38–2.26 (1H, m), 2.16–1.96 (1H, m). HRMS Calc'd for $C_{19}H_{23}N_2OCl$: 330.1499. Found: 330.1412

EXAMPLE 36

Cis-3-(2-methoxybenzylamino)-2-(2-methylphenyl)-piperidine (X=2-CH₃). M.p. 260° C. (HCl salt). ¹H NMR (CDCl₃) δ 7.97 (1H, bd, J—8Hz), 7.49–7.32 (4H, m), 7.08 (1H, d, J=6 Hz), 6.95–6.88 (2H, m), 5.04 (1H, d, J=3 Hz), 4.1 (1H, d, J=14 Hz), 3.88–3.8 (2H, m), 3.68 (3H, s), 3.49–3.36 (1H, m), 2.59–2.27 (4H, m), 2.25 (3H, s), 2.0 (1H, bd, J=10 Hz). HRMS Calc'd for $C_{20}H_{26}N_2O$: 310.2045. Found: 310.2080. C, 62.66; H, 7.36; N, 7.31. Found: C, 62.75; H, 7.46; N, 7.2

EXAMPLE 37

Cis-3-(2-methoxybenzylamino)-2-(3-trifluoromethylphenyl)-piperidine (X=3-CF₃). M.p. 268° C. (HCl salt). ¹H NMR (CDCl₃) δ 8.03–7.94 (2H, m), 7.84 (1H, d, J=8 Hz), 7.77 (1H, t, J=8 Hz), 7.37 (1H, t, J=8 Hz), 7.16 (1H, d, J=8 Hz), 6.93 (2H, t, J=7 Hz), 5.05 (1H, d, J=2 Hz), 4.14 (1H, d, J=13 Hz), 3.86 (1H, d, J=13 Hz), 3.72 (3H, s), 3.7–3.62 (1H, m), 3.3–3.2 (1H, m), 2.49–2.34 (2H, m), 2.3–2.18 (1H, m), 2.01 (1H, bd, J=14 Hz).

EXAMPLE 38

Cis-3-(2-methoxybenzylamino)-2-(3-fluorophenyl)-piperidine (X=3-F). M.p. 264° C. (HCl salt). ¹H NMR (CDCl₃) δ 7.62–7.45 (3H, m), 7.38 (1H, t, J=7 Hz), 7.3–7.21 (2H, m), 6.93 (2H, t, J=8 Hz), 5.03 (1H, d, J=3Hz), 4.16 (1H, d, J=15 Hz), 4.06–3.96 (1H, m), 3.85 (1H, d, J=13 Hz), 3.75 (3H, s), 3.66 (1H, bd, J=12 Hz), 2.47–2.40 (2H, m), 2.30–2.15 (1H, m), 2.06–1.92 (1H, m). HRMS Calc'd for $C_{19}H_{23}N_2OF$: 314.1795. Found: 314.1790.

EXAMPLE 39

Cis-3-(2-methoxybenzylamino)-2-(3-chlorophenyl)-piperidine (X=3-Cl). M.p. 258°–260° C. (HCl salt). ¹H NMR (CDCl₃) δ 7.72 (1H, bs), 7.7–7.58 (1H, m), 7.54 (2H, d, J=4 Hz), 7.4 (1H, t, J=8 Hz), 7.2 (1H, d, J=7 Hz), 6.97–6.92 (2H, m), 5.01 (1H, d, J=4 Hz), 4.17 (1H, d, J=13 Hz), 3.99 (1H, bs), 3.88 (1H, d, J=13 Hz), 3.75 (3H, s), 3.69–3.54 (1H, m), 3.17–3.14 (1H, m), 2.49–2.4 (2H, m), 2.3–2.16 (1H, m), 2.05–1.94 (1H, m). HRMS Calc'd for $C_{19}H_{23}N_2OCl$: 330.1499. Found: 330.1508.

EXAMPLE 40

Cis-3-(2-methoxybenzylamino)-2-(3-methoxyphenyl)-piperidine (X=3-OMe). M.p. 252° C. (HCl salt). ¹H NMR (CDCl₃) δ 7.49–7.34 (2H, m), 7.28–7.16 (3H, m), 7.07 (1H, d, J=6 Hz), 6.96–6.91 (2H, m), 4.94 (1H, d, J=4 Hz), 4.15 (1H, d, J=13 Hz), 3.96 (1H, bs), 3.86 (1H, d, J=13 Hz), 3.83 (3H, s), 3.69 (3H, s), 3.68–3.6 (1h, m), 3.28–3.22 (1H, m), 2.49–2.35 (2H, m), 2.32–2.16 (1H, m), 2.06–1.94 (1H, m). HRMS Calc'd for $C_{20}H_{26}N_2O_2$: 326.1994. Found: 326.1983. C. 60.15; H, 7.07; N, 7.01. Found: C, 59.78; H, 6.75; N, 7.01.

EXAMPLE 41

Cis-3-(2-methoxybenzylamino)-2-(3-methylphenyl)-piperidine (X=3-CH₃). M.p. 243° C. (HCl salt). ¹H NMR (CDCl₃) δ 7.15 (2H, dd, J=8.7 Hz), 7.07–6.94 (4H, m), 6.79 (1H, t, J=7 Hz), 6.67 (1H, d, J=8 Hz), 3.83 (1H, d, J=2 Hz), 3.68 (1H, d, J=14 Hz), 3.44 (3.44 (3H,s), 3.4 (1H, d, J=14 Hz), 3.26 (1H, bd, J=12 Hz), 2.85–2.73 (1H, m), 2.3 (3H, s), 2.12 (1H, bd, J=14 Hz), 1.92 (1H, qt, J=13, 4 Hz), 1.58 (1H, tt, J=14 Hz), 1.38 (1H, bd, J=13 Hz). HRMS Calc'd for $C_{20}H_{26}N_2O$: 310.2045. Found: 310.2069. C, 62.66; H, 7.36; N, 7.31. Found: C, 62.61; H, 7.44; N, 7.24.

EXAMPLE 42

Cis-3-(2-methoxybenzylamino)-2-(4-phenylphenyl)-piperidine (X=4-Ph). M.p. 255° C. (HCl salt). $^1$H NMR (CDCl$_3$) δ 7.77–7.7 (4H, m), 7.63–7.44 (3H, m), 7.41 (2H, t, J=2 Hz), 7.39–7.31 (2H, m), 7.15 (1H, dd, J=6, 2 Hz), 6.92 (1H, t, J=7 Hz), 6.79 (1H, d, J=8 Hz), 5.03 (1H, bs), 4.13 (1H, d, J=13 Hz), 3.87 (2H, d, J=13 Hz), 3.6 (4H, s), 3.34–3.3 (2H, bs), 2.58–2.1 (3H, m), 2.00–1.89 (1H, m). HRMS Calc'd for C$_{25}$H$_{28}$N$_2$O: 372.2202. Found: 372.2220.

EXAMPLE 43

Cis-3-(2-methoxybenzylamino)-2-(4-fluorophenyl)-piperidine (X=4-F). M.p. 252° C. (HCl salt). IR (KBr) max 3280, 2600, 1605, 1520, 1240, 1020 cm$^{-1}$. $^1$H NMR (CDCl$_3$) δ 7.25–7.12 (3H, m), 6.99–6.94 (3H,m), 6.8 (1H, t, J=6 Hz), 6.68 (1H, d, J=8 Hz), 3.83 (1H, bs), 3.67 (1H, d, J=14 Hz), 3.49 (3H, s), 3.38 (1H, d, J=14 Hz), 3.26–3.2 (1H, m), 2.82–2.71 (2H, m), 2.11 (1H, bd, J=13 Hz), 1.97–1.83 (1H, m), 1.63–1.52 (1H, m), 1.38 (1H, bd, J=13 Hz). $^{13}$C NMR (CDCl$_3$) δ 157.6, 138.3, 129.6, 128.3, 127.9, 127.8, 120, 114.9, 114.6, 109.8, 63.4, 54.8, 54.6, 47.8, 46.7, 28.2, 20.3. HRMS Calc'd. for C$_{19}$H$_{23}$N$_2$OF: 314.1795. Found: 314.1802.

EXAMPLE 44

Cis-3-(2-methoxybenzylamino)-2-(4-methylphenyl)-piperidine (X=4-CH$_3$). M.p. 233° C. (HCl salt). IR (KBr) max 3400, 2700, 1610, 1570, 1460, 1260, 1040 cm$^{-1}$. $^1$H NMR (CDCl$_3$) δ 7.18–7.11 (5H, m) 6.97 (1H, dd, J=7, 2 Hz) 6.79 (1H, t, J=8 Hz), 6.67 (1H, d, J=8 Hz), 3.84 (1H, d, J=2 Hz), 3.67 (1H, d, J=14 Hz), 3.45 (3H, s), 3.4 (1H, d, J=14 Hz), 3.25 (1H, bd, J=8 Hz), 2.82–2.73 (2H, m), 2.31 (3H, s), 2.11 (1H, bd, J=13 Hz), 1.91 (1H, qt, J=9, 4 Hz), 1.57 (1H, tt, J=14, 4 Hz), 1.37 (1H, bd, J=13 Hz). $^{13}$C NMR (CDCl$_3$) δ 157.6, 139.4, 135.9, 129.6, 128.8, 128.4, 127.7, 126.2, 120, 109.8, 63.7, 54.8, 54.7, 47.8, 46.7, 28.2, 21.0, 20.4. HRMS Calcd for C$_{20}$H$_{26}$N$_2$O: 310.2045. Found: 310.2043.

EXAMPLE 45

Cis-3-(2-methoxybenzylamino)-2-(4-chlorophenyl-piperidine (X=4-Cl). M.p. 247° C. (HCl salt). IR (KBr) max 2950, 2640, 1610, 1570, 1500, 1450, 1250 cm$^{-1}$. $^1$H NMR (CDCl$_3$) δ 7.26–7.13 (5 H, m), 6.97 (1H, dd, J=7, 2 Hz), 6.81 (1H, t, J=8 Hz), 6.68 (1H, d, J=8 Hz), 3.84 (1H, d, J=Hz), 3.7 (1H, d, J=14 Hz), 3.48 (3H, s), 3.37 (1H, d, J=14 Hz), 3.26 (1H, bd, J=8 Hz), 2.83–2.72 (2H, m), 2.12 (1H, bd, J=9 Hz), 1.91 (1H, qt, J=13, 4 Hz), 1.58 (1H, tt, J=13, 4 Hz), 3.83 (1H, bd, J=13 Hz). $^{13}$C NMR (CDCl$_3$) δ 157.6, 140.6, 132.4, 129.7, 128.2, 128, 127.7, 120, 109.9, 63.3, 54.8, 54.5, 47.7, 46.8, 28, 20. HRMS Calc'd for C$_{19}$H$_{23}$N$_2$OCl: 330.1498. Found: 330.1489. C, 56.52; H, 6.24; N, 6.94. Found: C, 56.52; H, 6.2; N, 6.86.

EXAMPLE 46

Cis-3-(2-methoxybenzylamino)-2-(4-methoxyphenyl)-piperidine (X=4-OMe). M.p. 245° C. (HCl salt). $^1$H NMR (CDCl$_3$) δ 7.14 (3H, t, J=8 Hz), 6.97 (1H, dd, J=7, 2 Hz), 6.84–6.77 (3H, m), 6.67 (1H, d, J=8Hz), 3.81 (1H, d, J=2 Hz), 3.78 (1H, s), 3.67 (1H, d, J=14 Hz), 3.47 (3H, s), 3.4 (1H, d, J=14 Hz), 3.24 (1H, bd, J=10 Hz), 2.81–2.72 (2H, m), 2.1 (1H, bd, J=14 Hz), 1.9 (1H, qt, J=14, 4 Hz), 1.56 (1H, tt, J=14, 4 Hz), 1.36 (1H, bd, J=14 Hz). $^{13}$C NMR (CDCl$_3$) δ 158.3, 157.6, 134.6, 129.6, 128.4, 127.7, 127.3, 120, 113.5, 109.8, 63.4, 55.2, 54.8, 54.7, 47.8, 46.7, 28.2, 20.3. HRMS Calc'd for C$_{20}$H$_{26}$N$_2$O$_2$: 326.1996. Found: 326.1968. C, 60.15, H, 7.07; N, 7.01. Found: C, 59.36; H, 6.79; N, 6.82.

EXAMPLE 47

Cis-3-(2-methoxybenzylamino)-2-(4-trifluoromethyl-phenyl)-piperidine

X=4-CF$_3$). M.p. 250° C. (dec., HCl salt). $^1$H NMR (CDCl$_3$) δ 7.51 (2H, d, J=8 Hz), 7.33 (2H, d, J=8 Hz), 7.13 (1H, t, J=8 Hz), 6.93 (1H, d, J=8 Hz), 6.77 (1H, t, J=8 Hz), 6.63 (1H, d, J=8 Hz), 3.89 (1H, s), 3.67 (1H, d, J=14 Hz), 3.39 (3H, s), 3.33 (1H, d, J=14 Hz), 3.24 (1H, bd, J=12 Hz), 2.82–2.74 (2H, m), 2.13 (1H, bd, J=14 Hz), 1.98–1.78 (1H, m), 1.64–1.46 (1H, m), 1.38 (1H, bd, J=14 Hz). $^{13}$C NMR (CDCl$_3$) δ 157.4, 146.5, 129.5, 127.8, 126.5, 124.8, 124.7, 119.8, 109.7, 63.6, 54.4, 54.3, 47.5, 46.6, 28, 10. HRMS Calcd for C$_{20}$H$_{23}$N$_2$OF$_3$: 364.1762. Found: 364.1710.

EXAMPLE 48

Cis-3-(2-methoxybenzylamino)-2-(4-bromophenyl)-piperidine (X=4-Br). M.p. 250° C. (HCl salt). $^1$H NMR (CDCl$_3$) δ 7.36 (2H, d, J=8 Hz), 7.14–7.05 (3H, m), 6.95 (1H, dd, J=8, 2 Hz), 6.79 (1H, t, J=8 Hz), 6.67 (1H, d, J=8 Hz), 3.79 (1H, d, J=2 Hz), 3.66 (1H, d, J=14 Hz), 3.48 (3H, s), 3.34 (1H, d, J=14 Hz), 3.22 (1H, bd, J=14 Hz), 2.78–2.68 (2H, m), 2.17 (1H, bd, J=14 Hz), 1.96–1.78 (1H, m), 1.56 (1H, tt, J=14, 4 Hz), 1.38 (1H, bd, J=14 Hz). $^{13}$C NMR (CDCl$_3$) δ 157.6, 141.4, 131.1, 129.7, 128.1, 128, 127.9, 120.4, 120, 109.8, 63.4, 54.8, 54.4, 47.6, 46.8, 28.1, 20.2. HRMS Calc'd for C$_{19}$H$_{23}$N$_2$OBr: 374.0980. Found: 374.0926. C, 50.91; H, 5.62; N, 6.25 Found: C, 51.41; H, 5.48; N, 6.23.

EXAMPLE 49

Cis-3-(2-methoxybenzylamino)-2-(4-hydroxymethyl-phenyl)-piperidine

X=4-CH$_2$OH). M.p. 248° C. (HCl salt). $^1$H NMR (CDCl$_3$) δ 7.2–7.04 (5H, m), 6.95 (1H, dd, J=8, 2 Hz), 6.7 (1H, t, J=8 Hz), 6.64 (1H, d, J=8 Hz), 4.6 (2H, s), 3.82 (1H, d, J=2Hz), 3.62 (1H, d, J=14 Hz), 3.43 (3H, s), 3.37 (1H, d, J=14 Hz), 3.24 (1H, bd, J=8 Hz), 2.8–2.68 (2H, m), 1.96–1.8 (1H, m), 1.56 (1H, tt, J=14, 4 Hz), 1.36 (1H, bd, J=8 Hz). HRMS Calc'd for C$_{20}$H$_{26}$N$_2$O$_2$: 326.1994. Found: 326.1979. C, 60.15; H, 7.07; N, 7.02. Found: C, 60.04; H, 6.93; H, 6.83.

EXAMPLE 50

Cis-3-(2-methoxybenzylamino)-2-(3-fluoro-4-methoxy-phenyl)-piperidine (X=3-F, 4-OMe). M.p. 250° C. (dec., HCl salt). $^1$H NMR (CDCl$_3$) δ 7.15 (1H, dt, J=8, 2 Hz), 7.01–6.93 (3H, m), 6.89–6.78 (2H, m), 6.7 (1H, d, J=8 Hz), 3.87 (3H, s), 3.78 (1H, d, J=2 Hz), 3.68 (1H, d, J=14 Hz), 3.52 (3H, s), 3.38 (1H, d, J=14 Hz), 3.22 (1H, bd, J=9 Hz), 2.75 (2H, td, J=13, 3 Hz), 2.1 (1H, bd, J=13 Hz), 1.86 (1H, qt, J=13, 4 Hz), 1.56 (1H, tt, J=13, 3 Hz), 1.35 (1H, bd, J=13 Hz). $^{13}$C NMR (CDCl$_3$) δ 157.6, 135.8, 129.7, 128.2, 128, 121.8, 121.7, 120, 114.3, 114.1, 113, 109.8, 63, 56.3, 54.7, 54.5, 47.7, 46.8, 28.2, 20.3

EXAMPLE 51

Cis-3-(2-methoxybenzylamino)-2-(2,3-difluorophenyl)-piperidine (X=2,3-diF). M.p. 243° C. (HCl salt). $^1$H NMR (CDCl$_3$) δ 7.21–7.12 (2H, m), 7.09–7.01 (1H, m), 6.98 (1H, dd, J=7.2 Hz), 6.81 (1H, t, J=7 Hz), 6.69 (1H, d, J=8 Hz), 4.17 (1H, s), 3.61 (1H, d, J=14 Hz), 3.54 (3H, s), 3.36 (1H, d, J=14 Hz), 3.23 (1H, d, J=14 Hz), 2.89 (1H, bs), 2.79 (1H, td, J=12, 3 Hz), 2.03 (1H, bd, J=13 Hz), 1.85 (1H, qt, J=13, 4 Hz), 1.68–1.56 (1H, m), 1.41 (1H, bd, J=14 Hz). $^{13}$C NMR (CDCl$_3$) δ 157.5, 132.6, 132.4, 129.5, 128.3, 127.9, 123.6, 122.8, 120.2, 115.3, 115.1, 109.9, 58.3, 54.8, 53.2, 47.1, 28.6, 20.4.

EXAMPLE 52

Cis-3-(2-methoxybenzylamino)-2-(2,3-dichlorophenyl)-piperidine (X=2,3-diCl). M.p. 249° C. (HCl salt). $^1$H NMR (CDCl$_3$) δ 7.42 (1H, d, J=8 Hz), 7.35 (1H, d, J=8 Hz), 7.19 (1 H, t, J=8 Hz), 7.14 (1H, t, J=8 Hz), 6.91 (1H, d, J=8 Hz), 6.79 (1H, t, J=8 Hz), 6.68 (1H, d, J=8 Hz), 4.19 (1H, d, J=2 Hz), 3.55 (1H, d, J=12 Hz), 3.53 (3H, s), 3.32 (1H, d, J=14 Hz), 3.23 (1H, bd, J=12 Hz), 3.03–2.98 (1H, m), 2.81 (1H, td, J=13, 3 Hz), 2.01 (1H, bd, J=13 Hz), 1.97–1.75 (1H, m), 1.7–1.62 (1H, m), 1.42 (1H, bd, J=12 Hz).

EXAMPLE 53

Cis-3-(2-methoxybenzylamino)-2-(4-ethylaminophenyl)-piperidine (X=4-NEt). M.p. 241° C. (HCl salt). $^1$H NMR (CDCl$_3$) δ 7.14 (1H, t, J=8 Hz), 7.08–6.94 (3H, m), 6.78 (1H, t, J=8 Hz), 6.67 (1H, d, J=8 Hz), 6.52 (2H, d, J=8 Hz), 3.77 (1H, bs), 3.69 (1H, d, J=14 Hz), 3.5 (3H, s), 3.43 (1H, d, J=14 Hz), 3.33 (1H, bd, J=2 Hz), 3.12 (1H, q, J=8 Hz), 2.84–2.68 (1H, m), 2.09 (1H, bd, J=4 Hz), 1.96–1.49 (1H, m), 1.61–1.49 (1H, m), 1.35 (1H, bd, J=14 Hz), 1.25 (3H, t, J=8 Hz).

EXAMPLE 54

Cis-3-(2-methoxybenzylamino)-2-(3-methyl-4-methoxyphenyl)-piperidine (X=3-Me, 4-OMe). M.p. 248° C. (HCl salt). IR (KBr) max 3540, 2600, 1610, 1560, 1460, 1270, 1030 cm$^{-1}$. $^1$H NMR (CDCl$_3$) δ 7.13 (1H, t, J=8 Hz), 7.02 (1H, d, J=8 Hz), 6.94–6.9 (2H, m), 6.74 (1H, t, J=8 Hz), 6.7 (1H, d, J=8 Hz), 6.64 (1H, d, J=8 Hz), 3.79 (3H, s), 3.78 (1H, s), 3.67 (1H, d, J=1 Hz), 3.43 (3H, s), 3.38 (1H, d, J=14 Hz), 3.21 (1H, bd, J=14Hz), 2.14 (3H, s), 2.11–2.07 (1H, m), 1.93–1.74 (1H, m), 1.59–1.53 (1H, m), 1.38–1.33 (1H, m), $^{13}$C NMR (CDCl$_3$) δ 157.6, 156.5, 134.1, 129.6, 128.6, 128.4, 127.7, 126.1, 124.4, 119.9, 109.7, 109.6, 63.3, 55.4, 54.7, 53.4, 47.8, 46.6, 28.1, 20.4, 16.3. HRMS Calc'd for C$_{21}$H$_{28}$N$_2$O$_2$: 340.2151. Found: 340.2172.

EXAMPLE 55

Cis-3-(2-methoxybenzylamino)-2-(2-fluoro-6-chlorophenyl)-piperidine (X=2-F, 6-Cl). M.p. 245°–246° C. (HCl salt. IR (KBr) max 3280, 2700, 1610, 1580, 1500, 1450, 1260, 1010 cm$^{-1}$. $^1$H—NMR (CDCl$_3$) δ 7.16–7.1 (3H, m), 6.99–6.82 (2H, m), 6.79 (1H, t, J=8 Hz), 6.68 (1H, d, J=8 Hz), 4.37 (1H, d, J=2Hz), 3.68 (1H, d, J=14 Hz), 3.55 (1H, s), 3.47 (1H, d, J=14 Hz), 3.2 (1H, bd, J=14 Hz), 2.87–2.78 (1H, m), 2.7 (1H, t, J=14 Hz), 2.4–2.0 (1H, m), 1.84–1.6 (2H, m), 1.36 (1H, bd, J=14 Hz). $^{13}$C NMR (CDCl$_3$) δ 157.4, 129.3, 128.3, 128.2, 127.8, 125.7, 125.6, 120.3, 115.4, 115, 109.9, 62.8, 62.8, 54.9, 53, 47.9, 47.3, 28.6, 20.8. HRMS Calc'd for C$_{19}$H$_{22}$N$_2$OClF: 348.1405. Found: 348.1369.

The title compounds of Examples 56–60 have the following general formula and were prepared by a procedure similar to that described in Example 1.

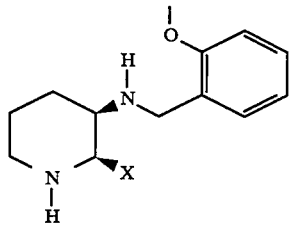

EXAMPLE 56

3-(2-Methoxybenzylamino)-piperidine (X=H). M.p. 198° C. (HCl salt). $^1$H NMR (HCl salt CD$_3$OH) δ 7.48 (2H, t, J=6 Hz), 7.12 (1H, d, J=6 Hz), 7.04 (1H, t, J=8 Hz), 4.33 (2H, a, J=4 Hz), 3.95 (3H, s), 3.8 (1H, bd, J=9 Hz), 3.7–3.54 (1H, m), 3.41 (1H, bd, J=9 Hz), 3.25 (1H, t, J=12 Hz), 3.18–3.01 (1H, m), 2.48–2.4 (1H, m), 2.24–2.1 (1H, m), 2.01–1.79 (1H, m). HRMS Calc'd for C$_{13}$H$_{22}$N$_2$O: 220.1576. Found: 220.1587.

EXAMPLE 57

Cis-3-(2-methoxybenzylamino)-2-(5-indanyl)-piperidine (X=5-indane). M.p. 243° C. (HCl salt). $^1$HNMR (CDCl$_3$) δ 7.24–7.11 (3H, m), 6.97 (2H, t, J=8 Hz), 6.79 (1H, t, J=8 Hz), 6.65 (1H, d, J=8 Hz), 3.83 (1H, bs), 3.68 (1H, d, J=14 Hz), 3.43 (3H, s), 3.39 (1H, d, J=14 Hz), 2.23 (1H, bd, J=14 Hz), 2.88–2.72 (6H, m), 2.13–1.86 (5H, m), 1.56 (1H, tt, J=13, 4 Hz), 1.37 (1H, bd, J=14 Hz).

EXAMPLE 58

Cis-3-(2-methoxybenzylamino)-2-(1-napthyl)-piperidine

X=1-napthyl). M.p. 251° C. (HCl salt). $^1$HNMR (HCl salt, CD$_3$OH) δ 8.16 (1H, d, J=6 Hz), 8.08 (1H, d, J=7 Hz), 8.04–7.98 (1H, m), 7.94–7.86 (1H, m), 7.71 (1H, t, J=8 Hz), 7.64–7.61 ($^1$H, m), 7.17 (1H, t, J=8 Hz), 6.84 (1H, d, J=6 Hz), 6.66 (2H, t, J=8 Hz), 5.73 (1H, bs), 4.06–3.99 (1H, m), 3.8–3.74 (2H, m), 3.49–3.4 (4H, m), 2.72–2.44 (3H, m), 6.84 (1H, bd, J=8 Hz). HRMS Calc'd for C$_{23}$H$_{26}$N$_2$O: 346.2045. Found: 346.2062.

EXAMPLE 59

Cis-3-(2-methoxybenzylamino)-2-(2-napthyl)-piperidine (X=2-naphthyl). M.p.>250° C. (dec., HCl salt). $^1$H NMR (CDCl$_3$) δ 7.87–7.78 (3H, m), 7.69 (1H, d, J=8Hz), 7.5–7.39 (2H, m), 7.14 (1H, d, J=8 Hz), 7.1 (1H, t, J=8 Hz), 6.92 (1H, d, J=8 Hz), 6.75 (1H, t, J=8 Hz), 6.47 (1H, d, J=8 Hz) 4.02 (1H, d, J=2 Hz), 3.66 (1H, d, J=14 Hz), 3.37–3.2 (2H, m), 2.97 (3H, s), 2.89 (1H, bs), 2.88–2.79 (1H, m), 2.16 (1H, bd, J=14 Hz), 1.98 (1H, qt J=8, 3 Hz), 1.63 (1H, tt, J=4, 12 Hz), 1.43 (1H, bd, J=13 Hz).

EXAMPLE 60

Cis-3-(2-methoxybenzylamino)-2-cyclopentyl-piperidine (X=cyclopentyl). M.p. 161° C. (HCl salt). IR (KBr) max 3480, 3420, 2960, 1610, 1500, 1260, 1020 cm$^{-1}$. $^1$HNMR (CDCl$_3$) δ 7.48 (1H, d, J=8 Hz), 7.17 (1H, t, J=8 Hz), 6.9 (1H, t, J=8 Hz), 6.8 (1H, d, J=8 Hz), 3.78 (3H, s), 3.67 (1H, d, J=13 Hz), 3.57 (1H, d, J=13 Hz), 2.97 (1H, bd, J=13 Hz), 2.69–2.64 (2H, m), 2.47 (1H, t, J=9 Hz), 2.3–2.2 (2H, m), 1.75 (1H, bd, J=9 Hz), 1.6–1.16 (7H, m), 1.0–0.9 (1H, m). $^{13}$C NMR (CDCl$_3$) δ 157.9, 130.6, 128.5, 127.5, 120.2, 110, 61.3, 59.2, 55.1, 47.9, 47.2, 39, 29.2, 27.3, 26.2, 25.8, 24.1, 23.1. HRMS Calc'd for C$_{18}$H$_{28}$N$_2$O: 288.2201. Found: 288.2172.

The title compounds of Example 61–62 have the following general formula and were prepared by a procedure similar to that described in Example 1.

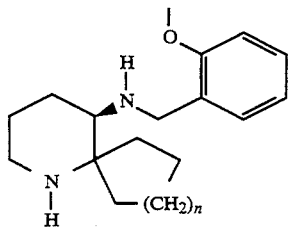

EXAMPLE 61

5-(2-Methoxybenzylamino)-1-aza-spiro[5.5]undecane (n=2) M.p. 257° C. (HCl salt). IR (KBr) max 2940, 1605, 1580, 1500, 1460, 1250, 1020 cm$^{-1}$. $^1$H NMR (CDCl$_3$) δ 7.27–7.18 (2H, m), 6.89 (1H, t, J=8 Hz), 6.84 (1H, d, J=8 Hz), 3.86 (1H, d, J=14 Hz), 3.82 (3H, s), 3.68 (1H, d, J=14 Hz), 2.74–2.68 (2H, m), 2.25–2.08 (1H, m), 1.81–1.25 (13H, m). HRMS Calc'd for C$_{18}$H$_{28}$N$_2$O: 288.2202. Found: 288.2182.

EXAMPLE 62

10-(2-methoxybenzylamino)-6-aza-spiro[4.5]decane (n=1). M.p. 247° C. (HCl salt). IR (KBr) max 2960, 2700, 1605, 1580, 1500, 1480, 1260, 1030 cm$^{-1}$. $^1$H NMR (CDCl$_3$) δ 7.23–7.18 (2H, m), 6.89 (1H, t, J=8 Hz), 6.84 (1H, d, J=8 Hz), 3.89 (1H, d, J=14 Hz), 3.83 (3H, s), 3.66 (1H, d, J=14 Hz), 2.76–2.7 (2H, m), 2.31 (1H, dd, J=8, 3 Hz), 1.81–1.24 (12H, m). HRMS Calc'd for C$_{17}$H$_{26}$N$_2$O; 274.2085. Found: 274.2057.

EXAMPLE 63

Cis-3-(2-methoxybenzylamino)-2-phenylpiperidine

A. 4-Phenyl-1-(tert.-butyldimethylsilyl)asetidin-2-one

4-Phenylazetidin-2-one (10.4 gm, 71.0 mmol) (Graf, Chem. Ber, 111 (1963); Durst et al. *J. Org. Chem.*, 35, 2043 (1970)) was dissolved in DMF (200 ml) and as treated with tert.-butyldimethylsily chloride (12.8 gm, 85 mmol) and triethylamine (11.8 ml, 85 mmol). The mixture was stirred at room temperature for 16 hrs. and taken up in ether (500 ml). The ethereal solution was washed with 1 N hydrochloric acid (1×100 ml), water (2×50 ml) and brine (1×50 ml). After the solution was dried (anhyd. magnesium sulfate) and evaporated, the residue was flash chromatograph on SiO$_2$-gel column. Elution with 15% ethyl acetate in hexane afforded 4-phenyl-1-(tert.-butyldimethylsilyl)azetidin-2-one (18.4 gm, 99%) as an oil which solidified on standing.

$^1$H NMR (CDCl$_3$) δ 7.37–7.29 (5H, m), 4.51 (1H, dd, J=6, 3Hz), 3.5 (1H, dd, J=16, 6 Hz), 2.93 (1H, dd, J=16, 3 Hz), 0.9 (3H, s), 0.89 (9H, s), 0.19 (3H, s).

B. 3-(3'-Chlropropyl)-4-phenyl-1-(tert.-butyldimethylsilyl)azetidin-2-one

To a stirred solution of 4-phenyl-1-(tert.-butyldimethylsilyl)azetidin-2-one (9.75 gm, 37 mmoles) in THF (100 ml) at −50° C., a freshly prepared solution of lithium diethylamide (1M in THF, 44 ml, 45 mmole) wa added rapidly under nitrogen. The reaction mixture was stirred further for 15 min. at −50 C. and then a solution of 1-bromo-3-chloropropane (7.4 ml, 75 mmole) in THF (20 ml) was added. The resulting mixture was stirred for 15 min. at −50° C., after which ammonium chloride (saturated aqueous solution) was added. After the mixture was taken up in ether (2×300 ml), it was washed with saturated aqueous sodium chloride. The ether solution was dried (magnesium sulfate) and concentrate, and the residue (17.0 gm) was chromatographed on a silicon dioxide-gel column. Elution with 5% ethyl acetate in hexane afforded 3-(3'-chloropropyl)-4-phenyl-1-(tert.-butyldimethylsilyl)azetidin-1-one as an oil (7.6 gms, 58%).

$^1$H NMR (CDCl$_3$) δ 7.2–7.4 (1H, m), 4.18 (1H, d, J=2.5 Hz), 3.5 (2H, t, J=5 Hz), 3.04 (1H, dt, J=2.5, 7.5 Hz), 1.7–2.05 (4H, m), 0.9 (9H, s), 0.2 (3H, s).

C. Cis-Methyl-2-phenylpiperidine-3-carboxylate 3-(3'-Chloropropyl)-4-phenyl-1-(tert.-butyldimethylsilyl)azetidin-2-one (3.07 gm, 9.0 mmole) was dissolved in 10% methanolic sulfuric acid and refluxed for 16 hours. At the end of this period, the reaction mixture was cooled, the sulfuric acid was neutralized with sodium bicarbonate and the mixture was taken up in ether (2×200 ml). The ethereal solution was washed with water (2×50 ml) and dried (anhyd. magnesium sulfate). Evaporation afforded essentially pure 5-chloro-2-carbomethoxy-1-phenylpent-1-ylamine as an oil (2.11 gms). The 5-chloro-2-carbomethoxy-1-phenylpent-1-ylamine thus obtained was dissolved in the dimethylformamide ("DMF") (20 ml) and sodium iodide (2.11 gm) and sodium bicarbonate (2.11 gm) were added. The resulting mixture was refluxed for 15 min. At the end of this period, the reaction mixture was cooled and taken up in ether (200 ml). The ethereal solution as washed with water (2×50 ml) and dried (anhyd. magnesium sulfate). Evaporation of the ether afforded chromatographically pure cis-methyl 2-phenylpiperidine-3-carboxylate as an oil (1.54 gm, 78%).

$^1$H NMR (CDCl$_3$) δ 7.31–7.5 (5H, m), 3.95 (1H, d, J=3.5 Hz), 3.42 (3H, s), 3.39–3.30 (1H, m), 3.01–2.93 (1H, m), 2.84–2.74 (1H, m), 2.22–2.11 (1H, m), 1.90–1.66 (3H, m), 1.53–1.46 (1H, m).

D. Cis-methyl 2-phenylpiperidine-1-(benzyloxycarbonyl)-3-carboxylate

Cis-methyl-2-phenylpiperidine-3-carboxylate (1.54 gm, 7.0 mmole), triethylamine (1.5 ml, 11.0 mmole) and benzyl chloroformate (1.5 ml, 11.0 mmole) were mixed in methylene chloride (45 ml) at 25 C. and stirred for 15 hours. At the end of this period, the reaction mixture was taken up in ether (100 ml), washed with water (2×50 ml) and dried (anhyd. magnesium sulfate). The solvent was removed under reduced pressure to afford a residue which was chromatographed on a flash SiO$_2$-gel column. Elution with 1:1 ethyl acetate/hexane afforded cis-methyl 2-phenylpiperidine-1-(benzyloxycarbonyl)-3-carboxylate as an oil (1.91 gm, 77%).

$^1$H NMR (CDCl$_3$) δ 7.34–7.12 (10H, m), 5.97 (1H, bd), 5.30–5.1 (1H, m), 5.17 (1H, s), 4.15–3.90 (1H, m), 3.59 (3H, s), 2.98–2.91 (1H, m), 2.75 (1H, bt, J=12 Hz), 2.14–2.00 (2H, m), 1.85–1.48 (2H, m).

$^{13}$C NMR (CDCl$_3$) δ 172.9, 138.3, 126.7, 128.5, 128.0, 127.9, 127.3, 67.4, 54.6, 51.8, 39.7, 25.1, 21.5.

E.
Cis-2-phenylpiperidine-1-(benzyloxycarbonyl)-3-carboxamide

To a suspension of ammonium chloride (1.66 gm, 31 mmole) in benzene (60 ml) at −5° C., was slowly added a 2 M solution (15.6 ml, 31 mmole) of trimethyl aluminum in hexane. After addition was complete, the reaction mixture was allowed to warm to room temperature and was stirred for 1 hr until gas evolution had ceased. A solution of cis-methyl 2-phenylpiperidine-1-(benzyloxycarbonyl)-3-carboxylate (2.2 gm, 6.2 mmole) in benzene (10 ml) was added and the solution was maintained at 50° C. for 16 hours. The reaction mixture was cooled to room temperature and was carefully quenched with 5% HCl. The resulting mixture was filtered through diatomaceous earth (Celite (trademark)) and the residue was washed with methylene chloride (200 ml). The organic layer was separated while the aqueous layer was made basic and extracted with methylene chloride (200 ml). The organic extracts were combined, dried (anhyd. magnesium sulfate) and concentrated in vacuo to afford a residue which was suspended in 1:1 ether-pentane to afford cis-2-phenylpiperidine-1-(benzyloxycarbonyl)-3-carboxamide as a white solid (1.4 gm, 66%). M.p. 171° C.

$^1$H NMR (CDCl$_3$) δ 7.35–7.28 (10H, m), 5.86 (1H, d, J=4.9 Hz), 5.66–5.58 (1H, m), 5.48–5.37 (1H, m), 5.21 (1H, d, J=12 Hz), 5.13 (1H, d, J=12 Hz), 4.02 (1H, bd, J=13 Hz), 2.9–2.74 (2H, m), 2.11–1.98 (2H, m), 1.86–1.76 (1H, m), 1.66–1.5 (1H, m).

HRMS Calc'd for C$_{20}$H$_{22}$N$_2$O$_3$: 338,1630. Found: 338.1634.

F.
Cis-1-(benzyloxycarbonyl)-3-amino-2-phenylpiperidine

Cis-2-phenylpiperidine-1-(benzyloxycarbonyl)-3-carboxamide (1.4 gm, 4.1 mmole) was dissolved in dry tert.-butanol (40 ml) at 50° C., and lead tetraacetate (1.9 gm, 4.3 mmole) was added. The resulting brown reaction mixture was refluxed for 0.5 hours. Additional lead tetraacetate (1.9 gm, 4.3 mmole) was added over a period of 1 hour. At the end of this period, the reaction mixture was poured into cold 1 N hydrochloric acid and filtered through diatomaceous earth (Celite (trademark)). The aqueous phase was extracted with ethyl acetate (3×100 ml) and the combined organic layers were washed successively with water, 5% aqueous sodium hydroxide, water, and brine and dried (anhyd. magnesium sulfate). Evaporation of the solvent under reduced pressure afforded a residue which was chromatographed on a SiO$_2$-gel column. Elution with 25% ethyl acetate in hexane afforded chromato- graphically homogeneous cis-1-(benzoyloxycarbonyl)-3-(N-tert-butoxycarbonyl)-2-phenylpiperidine (1.1 gm) as oil. This was dissolved in ethyl acetate (20 ml) and hydrogen chloride gas was bubbled through it for 5 min. Then the reaction mixture was taken up in aqueous ammonia and extracted with methylene chloride (2×200 ml). the organic extracts were combined, dried and evaporated to afford chromatographically pure cis-1-(benzyloxycarbonyl)-3-amino-2-phenylpiperidine as oil (0.830 gms, 65%).

Cis-1-(benzoyloxycarbonyl)-3-(N-tert.-butoxycarbonyl)-2-phenylpiperidine: $^1$H NMR (CDCl$_3$) δ 7.39–7.16 (10H, m), 5.46 (1H, bd, J=6 Hz), 5.13 (1H, d, J=13 Hz), 4.98 (1H, d, J=13 Hz), 4.14–3.93 (2H, m), 3.23 (1H, bt), 1.9–1.5 (5H, m), 1.39 (9H, s).

Cis-1-(benzyloxycarbonyl)-3-amino-2-phenylpiperidine: $^1$H NMR (CDCl$_3$) 7.42–7.36 (2H, m), 7.32–7.12 (8H, m), 5.26 (1H, d J=5 Hz), 5.07 (1H, d, J=12 Hz), 4.95 (1H, d, J=12 Hz), 4.06 (1H, bd, J=12, 5 Hz), 3.12–3.08 (2H, m), 1.88–1.53 (4H, m).

G. Cis-3-(2-methoxybenzylamino)-2-phenylpiperidine

Cis-1-(benzyloxycarbonyl)-3-amino-2-phenylpiperidine (0.78 gm, 2.5 mmole) was dissolved in methanol (25 ml) and the pH of the medium was adjusted to 5 with the help of methanolic hydrochloric acid. To it crushed molecular sieves (1.0 gm), sodium cyanoborohydride (0.163 gm, 2.5 mmole) and o-methoxybenzaldehyde (0.411 gm, 3.0 mmole) were added, and the resulting reaction mixture was stirred at room temperature for 16 hours. At the end of this period, the reaction mixture was filtered through diatomaceous earth (Celite (trademark)) and the filtrate was taken up in aqueous ammonium hydroxide. The aqueous phase was extracted with methylene chloride (3×60 ml) and dried (anhyd. magnesium sulfate). The solvents were removed under reduced pressure to afford an oily residue (1.18 gm). This was dissolved in ethanol (27 ml) and 10% palladium on carbon (1.2 gm) and ammonium formate (0.864 gm, 14 mmole) were added. The resulting reaction mixture was stirred at 25 C for 16 hrs. At the end of this period, the reaction mixture as filtered through diatomaceous earth (Celite (trademark)), which was washed with ethanol (50 ml) and methylene chloride (100 ml). The solvents were removed under vacuum to afford a solid which was taken up in aqueous ammonium hydroxide and extracted with methylene chloride (3×60 ml). The organic extracts were combined and dried (anhyd. magnesium sulfate). Evaporation of the solvents under pressure afforded a yellow oil from which cis-3-(2-methoxybenzylamino)-2-phenylpiperidine (728 mg, 83%) was isolated as white solid by treatment with ether-HCl. This was crystallized from ethanol/methanol to afford the hydrochloride salt of the title compound (0.58 mg, m.p. 250 C.).

EXAMPLE 64
(+) S,S-Cis-3-(2-methoxybenzylamino)-2-phenylpiperidine

The title compound was prepared according to the procedure of Example 63, starting with enantiomerically pure (+)R-4-phenylazetidin-2-one.

M.p. 249° C. (dec., HCl salt). [α]$_D$=+77 (c=1, CH$_3$OH).

EXAMPLE 65
(−)R,R-Cis-3-(2-methoxybenzylamino)-2-phenylpiperidine

The title compound was prepared by the procedure described in example 63, starting with enantiomerically pure (−)S-4-phenylazetidin-2-one.

M.p. 251° C. (dec., HCl salt). [α]_D = −79° (c=1, CH₃OH).

The title compounds of examples 66–70 have the following general formula and were prepared by a procedure similar to that described in Example 1.

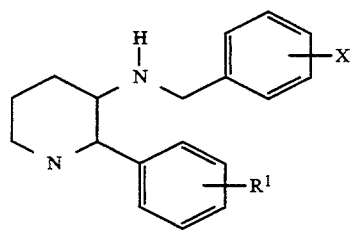

EXAMPLE 66

Trans-3-(2-chlorobenzylamino)-2-phenylpiperidine (R₁=H, X=2-Cl). M.p.>255° C. (dec., HCl salt). $^1$H NMR (CDCl₃) δ 7.42–7.02 (9H, m), 3.69 (1H, d, J=13.9 Hz), 3.56 (1H, d, J=13.8 Hz), 3.80 (1H, d, J=9.1 Hz), 3.09 (1H, bd, J=11.4 Hz), 2.75 (1H, dt, J=11.8, 2.9 Hz), 2.62–2.54 (1H, m), 2.29–2.23 (1H, m), 1.79–2.23 (2H, m), 1.34–1.24 (1H, m). HRMS Calc'd for $C_{18}H_{21}N_2Cl$: 300.1392. Found: 300.1387.

EXAMPLE 67

Cis-3-benzylamino-2-(3-trifluorophenyl)-piperidine (R₁=3-CF₃, X=H). M.p.>270° C. (dec., HCl salt). $^1$H NMR (HCL salt, MeOH—CDCl₃) δ 8.85 (2H, bs), 8.74–8.44 (2H, m), 8.21 (1H, 2), 81.6–8.02 (4H, m), 5.97 (1H, bs), 4.86 (1H, bs), 4.58 (1H, t, J=10 Hz), 4.46–4.36 (2H, m), 4.2–4.14 (2H, m), 3.24–3.08 (3H, m), 2.75 (1H, bd, J=10 Hz). HRMS Calc'd for $C_{19}H_{21}N_2CF_3$: 296.1889. Found: 296.1904.

EXAMPLE 68

Cis-3-benzylamino-2-phenylpiperidine (R¹=H, X=H). M.p. 250° C. (dec. HCl salt). $^1$H—NMR (CDCl) δ 6.94–7.4 (10H, m), 3.89 (1H, d, J=2.3 Hz), 3.52 (1H, d, J=13 Hz), 3.32 (1H, d, J=13 Hz), 3.25 (1H, bd, J=12 Hz), 2.88 (1H, d, J=2.5 Hz), 2.78 (1H, dt, J=12, 3Hz), 2.4 (1H, d, J=12 Hz), 1.8–1.98 (1H, m), 1.6 (1H, d, J=12, 2.5 Hz), 1.42 (1H, d, J=12 Hz).

EXAMPLE 69

Trans-3-(2-methoxybenzylamino)-2-phenylpiperidine (R₁=H, X=2-OMe). M.p>250° C. (dec., HCl salt). $^1$H NMR (CDCl₃) δ 7.29–7.24 (5H, m), 7.14 (1H, t, J=8 Hz), 6.97 (1H, d, J=8 Hz), 6.81 (1H, t, J=8 Hz), 6.67 (1H, d, J=8 Hz), 3.68 (1H, d, J=14 Hz), 3.47 (1H, bd, J=14 Hz), 3.39 (3H, s), 3.38–3.34 (1H, m), 3.06 (1H, bd, J=14 Hz), 2.73 (1H, td, J=9, 3 Hz), 2.51 (1H, td, J=8, 3 Hz), 2.32–2.2 (1H, m), 1.76–1.5 (2H, m), 1.36–1.2 (1H, m). MS (M+298.18).

EXAMPLE 70

Cis-3-benzylamino-2-(4-phenylphenyl)piperidine (R₁=4-Ph, X=H) M.p.>268° C. (HCl salt). $^1$H NMR (CD₃OH, HCl salt) δ 7.8 (4H, m), 7.59 (2H, d, J=5 Hz), 7.40 (2H, t, J=3 Hz), 7.38=7.24 (6H, m), 4.98 (1H, bs), 3.98 (1H, bs), 3.87 (1H, d, J=10 Hz), 3.68–3.58 (2H, m), 3.34–3.22 (3H, m), 2.46–2.16 (3H, m), 2.01–1.90 (1H, m). HRMS Calc'd for $C_{24}H_{26}N_2$: 342.2096. Found: 342.2057.

The title compounds of Examples 71–75 have the following general formula and were prepared by a procedure similar to that described in Example 1.

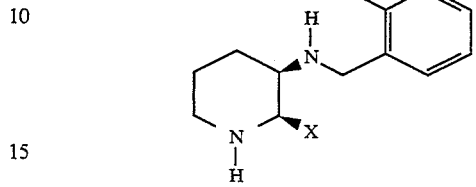

EXAMPLE 71

Cis-3-(2-methoxybenzylamino)-2-(3-thienyl)-piperidine (X=3-thienyl). M.p.>239° C. (HCl salt). $^1$H NMR (CDCl₃) δ 7.25–7.11 (3H, m), 7.03 (1H, dd, J=7.3, 1.7 Hz), 6.85–6.82 (2H, m), 6.73 (1H, d, J=8.2 Hz), 3.94 (1H, bs), 3.73 (1H, d, J=13.7 Hz), 3.57 (3H, s), 3.45 (1H, d, J=13.7 Hz), 3.20 (1H, bd, J=10.4 Hz), 2.82 (1H, d, J=2.7 Hz), 2.76 (1H, dt, J=12.5, 3.1 Hz), 2.11 (1H, bd, J=13.4 Hz), 1.97–1.84 (1H,m), 1.57 (1H, tt, J=13.4, 3.5 Hz), 1.36 (1H, bd, J=13.2 Hz). HRMS Calc'd for $C_{17}H_{22}N_2OS$: 302.1535. Found: 302.1444.

EXAMPLE 72

Cis-3-(2-methoxybenzylamino)-2-benzylpiperidine (X=benzyl). M.p.>241° C. (HCl salt). $^1$H NMR (CDCl₃) δ 7.37 (1H, dd, J=7.3, 1.6 Hz), 7.29–7.2 (6H, m), 6.93 (1H, dt, J=7.4, 1.0 Hz), 6.88 (1H, dd, J=8.2, 0.7 Hz), 3.89 (1H, d, J=13.5 Hz), 3.85 (1H, s), 3.70 (1H, d, J=13.5 Hz), 3.00–2.89 (2H, m), 2.82 (1H, s), 2.79 (1H, d, J=3.6 Hz), 2.71–2.67 (1H, m), 2.57 (1H, dt, J=10.7, 3.2 Hz), 1.97–1.92 (1H, m), 1.75–1.63 (1H, m), 1.44–1.36 (2H, m). HRMS Calc'd for $C_{20}H_{26}N_2O$: 310.2045. Found: 310.2073.

EXAMPLE 73

Cis-3-(2-methoxybenzylamino)-2-cyclohexylpiperidine (X=cyclohexyl). M.p. >225° C. (HCl salt. $^1$H NMR (CDCl₃) δ 7.13–7.31 (2H, m), 6.9 (1H, t, J=8 Hz), 6.82 (1H, d, J=9 Hz), 3.9 (1H, d, J=14 Hz), 3.81 (3H, s), 3.6 (1H, d, J=15 Hz), 3.11 (1H, bd, J=9 Hz), 2.72 (1H, bs), 2.6 (1H, t, J=10 Hz), 2.19 (1H, d, J=9 Hz), 2.11 (1H, bd, J=12 Hz), 2.01–1.53 (1H, m), 1.38–1.04 (6H, m), 0.92–0.65 (2H, m). HRMS Calc'd for $C_{19}H_{30}N_2O$: 302.2358. Found: 302.2352.

EXAMPLE 74

Cis-3-(2-methoxybenzylamino)-2-tert.butylpiperidine (X=tert. butyl). Mp.>251° C. (HCl salt). $^1$H NMR (CDCl₃) δ 7.33 (1H, dd, J=7.3, 1.6 Hz), 7.21 (1H, dd, J=7.8, 1.7 Hz), 6.90 (1H, dt, J=7.4, 0.95 Hz), 6.84 (1H, d, J=8.2 Hz), 3.91 (1H, d, J=13.6 Hz), 3.81 (3H, s), 3.55 (1H, d, J=13.6 Hz), 3.13 (1H, bd, J=12.1 Hz), 2.88 (1H, bs), 2.61 (1H, dt, J=12.3, 2.9 Hz), 2.19 (1H, d, J=1.9 Hz), 2.12 (1H, bd, J=12.9 Hz), 1.76–1.66 (1H, m, 1.35–1.22 (2H, m), 9.95 (9H, s). HRMS Calc'd for $C_{17}H_{28}N_2O$: 276.2201. Found: 276.2217.

EXAMPLE 75

Cis-3-(2-methoxybenzylamino)-2-(3-furanyl)-piperidine (X=3-furanyl). M.p.>247° C. (HCl salt). $^1$H NMR (CDCl$_3$) δ 7.34 (2H, d, J=1.4 Hz), 7.19 (1H, dt, J=7.7, 1.7 Hz), 7.11 (1H, dd, J=7.3, 1.6 Hz), 6.85 (1H, t, J=7.4 Hz), 6.77 (1H, d, J=8.1 Hz), 6.15 (1H, td, J=1.2 Hz), 3.8 (2H, d, J=14.0 Hz), 3.65 (3H, s), 3.54 (1H, d, J=13.6 Hz), 3.14 (1H, bd, J=12.7 Hz), 2.75 (2H, dt, J=12.1, 3.2 Hz), 2.09, (1H, bd, J=13.6 Hz), 1.93–1.83 (1H, m), 1.54 (1H, tt, J=13.2, 3.5 Hz), 1.36 (1H, bd, J=13.1 Hz). HRMS Calc'd for C$_{17}$H$_{22}$N$_2$O$_2$: 286.1681. Found: 286.1682.

EXAMPLE 76

Cis-3-(2-methoxybenzylamino)-2-phenylazacycloheptane

The title compound was prepared according to the procedure of Example 63 starting with (+)-4-phenylazetidine-2-one and using 1-bromo-4-chlorobutane in procedure B instead of 1-bromo-3-chloropropane. M.p. 230°–230° C. (dec HCl salt).

$^1$H—NMR (CDCl$_3$) δ 1.21 (m, 1H) 1.55 (m, 1H), 1.80 (m, 5H), 2.75 (m, 1H), 3.06 (m, 1H), 3.36 (m, 1H), 3.39 (s, 1H), 3.45 (d, 1H, J=13 Hz), 3.50 (m, 1H), 6.62 (d, 1H, J=6Hz), 6.76 (t, 1H, J=6 Hz), 6.91 (d, 1H, J=6 Hz), 7.12 (m, 2H), 7.22 (m, 4H). HRMS Calc'd for C$_{20}$H$_{27}$N$_2$O: 311.2124. Found: 311.2132.

The title compounds of examples 77–81 have the following general formula and were prepared similar to that described in Example 1.

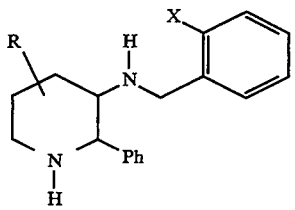

EXAMPLE 77

3α-(Benzylamino)-3β-methyl-2β-phenylpiperidine (R=CH$_3$, S=H)

M.p. 269° C. (dec., HCl salt).

$^1$H—NMR δ (CDCl$_3$, 300 MHz) 7.1–7.45 (m, 10H), 3.81 (dd, J=13Hz, 1H), 3.71 (s, 1H), 3.66 (dd, J=13Hz, 1H), 3.05–3.1 (m, 1H), 2.78 dt, J=3 and 11Hz, 1H), 1.4–2.0 (m, 4H), 1.15 (s, 3H). $^{13}$C—NMR (CDCl$_3$) δ 141.6, 141.1, 128.8, 128.3, 127.83, 127.81, 127.3, 126.6, 70.0, 65.9, 54.8, 47.9, 45.5, 37.1, 23.5, 18.9 and 15.3. Calc'd for C$_{19}$H$_{24}$N$_2$·2HCl·1/8H$_2$O C, 64.18; H, 7.44; N, 7.88. Found: C, 64.12; H, 7.36; N, 7.85. HRMS Calcd for C$_{19}$H$_{24}$N$_2$: 280.193. Found: 280.1932.

EXAMPLE 78

3β-(Benzylamino)-3α-methyl-2β-phenylpiperidine (R=CH$_3$, X=H)

M.p. 238° C. (HCl salt).

$^1$H—NMR δ (CDCl$_3$, 300 MHz) 7.1–7.4 (m, 10H), 3.64 (dd, J=13Hz, 1H), 3.52 (dd, J=13Hz, 1H), 3.50 (s, 1H, 3.13–3.18 (m, 1H), 2.73 (dt, J=12 and 3Hz, 1H), 2.1 (bd, J=13.8Hz, 1H), 1.45–1.52 (m, 1H), 1.25–1.4 (m, 1H), 0.93 (s, 3H). $^{13}$C—NMR (CDCl$_3$) δ 142.1, 141, 129.1, 128.1, 127.9, 127.5, 127, 126.4, 72.1, 53.3, 47.9, 45.3, 34.5, 24.7, 22.5. HRMS Calcd for C$_{19}$H$_{24}$N$_2$: 280.193. Found: 280.1930.

EXAMPLE 79

3α-(2-Methoxybenzylamino)-3β-methyl-2β-phenylpiperidine (R=CH$_3$, X=OCH$_3$)

M.p. 233° C. (dec., HCl salt).

$^1$H—NMR δ (CDCl$_3$, 300 MHz) 7.15–7.46 (m, 7H), 6.85 (dt, J=7 and 1Hz, 1H), 6.74 (d, J=8Hz, 1H), 3.7 (s, 1H), 3.68 (dd, J=13Hz, 1H), 3.6 (s, 3H), 3.16 (m, 1H), 2.76 (dt, J=3 and 11Hz, 1H), 1.97 (bd, J=11Hz, 1H), 1.55–1.83 (m, 3H), 1.14 (s, 3H), HRMS Calcd for C$_{20}$H$_{26}$N$_2$O: 310.2046. Found: 310.2038.

EXAMPLE 80

3β-(2-Methoxybenzylamino)-3α-methyl-2β-phenylpiperidine (R=CH$_3$, X=OCH$_3$)

M.p 242° C. (HCl salt).

$^1$H—NMR δ (CDCl$_3$, 300 MHz) 7.15–7.4 (m, 7H), 6.91 (dt, J=7 and 1 Hz, 1H), 6.81 (d, J=8 Hz, 1H), 3.73 (s, 3H), 3.63 dd, J=13Hz, 1H), 3.52 (s, 1H, 3.5 (dd, J=13Hz, 1H), 3.13–3.21 m, 1H), 2.75 (dt, J=12 and 3Hz, 1H), 2.16 (bd, J=14Hz, 1H), 1.73–1.91 (m, 1H), 1.48 (bd, J=13Hz, 1H), 1.33 (dt, J=14 and 4Hz, 1H), 0.93 (s, 3H). HRMS Calc'd for C$_{20}$H$_{26}$N$_2$O: 310.2045. Found: 310.2092.

EXAMPLE 81

3α-(2-Methoxybenzylamino)-5β-methyl-2β-phenylpiperidine (R=CH$_3$, X=OCH$_3$)

M.p. 208° C. (dec.).

$^1$H—NMR δ (CDCl$_3$, 300 MHz) 7.22–7.31 (m, 5H), 7.16 (dt, J=7 and 1Hz, 1H, 6.99 (dd, J=8 and 1Hz, 1H), 6.81 (dt, J=8 and 1Hz, 1H), 6.69 (bd, J=8Hz, 1H), 3.66 (dd, J=13, 1H), 3.46 (dd, J=13Hz, 1H), 3.43 (s, 0.3H), 3.36 (d, J=9Hz, 1H), 2.97 (dd, J=11 and 3Hz, 1H), 2.67–2.86 (m, 2H), 1.97–2.09 (m, 1H), 1.43–1.58 (m, 2H). 1.13 (d, J=7Hz, 3H). HRMS Calc'd for C$_{20}$H$_{26}$N$_2$O:310.2046. Found: 310.2045.

EXAMPLE 82

3β-(3-Thienylmethylamino)-2β-(3-thienyl)piperidine

The title compound was prepared by a procedure similar to that described in Example 1.

M.p. 262° C. (HCl salt).

$^1$H—NMR δ (CDCl$_3$, 300 MHz) 7.05–7.3 (m, 3H), 6.97 (dd, J=5 and 1Hz, 1H), 6.77 (dd, J=5 and 1Hz, 1H), 3.98 (d, J=2Hz, 1H), 3.6 (dd, J=14, 1H, 3.44 (dd, J=14Hz, 1H), 3.16–3.21 (m, 1H, 2.89–2.92 (m, 1H), 2.76 (dt, J=12 and 3Hz, 1H), 1.3–2.1 (m, 4H). $^{13}$C—NMR (CDCl$_3$) δ 144.1, 142, 127.5, 126.2, 125.7, 125.3, 120, 120.3, 61.2, 54.8, 47.5, 46.4, 28.7, 20.5. HRMS Calc'd for C$_{14}$H$_{18}$N$_2$S$_2$: 278.0906. Found: 278.0922. C, 47.86; H, 5.74; N, 7.97. Found: C, 47.87; H, 5.79; N, 7.61.

EXAMPLE 82-A

The title compound was prepared by a procedure similar to that described in Example 1.

Trans-3-benzylamino-2-phenylpiperidine (R=X=H)

M.p. 269° C. (dec., HCl salt).

$^1$H—NMR δ (CDCl$_3$, 300 MHz) 6.9–7.4 (m, 10H), 3.63 (dd, J=13Hz, 1H), 3.42 (dd, J=13 Hz, 1H), 3.38 (d, J=7.4 Hz, 1H), 3.07 (bdt, J=11.6 Hz, 1H), 2.14–2.24 (m, 1H), 1.56–1.8 (m, 3H), 1.2–1.38 (m, 1H). HRMS Calc'd for C$_{18}$H$_{22}$N$_2$: 266.1783. Found: 266.1764.

EXAMPLE 83

Cis-(2S,3S)-1-(4,4-bis-(4-fluorophenyl)butyl)-3-(2-methoxybenzyl)amino-2-phenyl-piperidine dimesylate The title compound was prepared by a procedure similar to that of Example 2.

$C_{35}H_{38}F_2N_2O \cdot 2CH_3SO_3H$, mp. 55°–60° C. (41%).

$^1H$ NMR (CDCl$_3$) δ 1.20–1.80 (m, 4H), 1.92–2.20 (m, 4H), 2.40 (m, 1H), 2.46–2.66 (m, 2H), 3.14 (m, 1H), 3.25 (s, 3H), 3.45 (s, 1H), 3.60–3.82 (m, 4H), 4.32 (m, 1H), 6.60 (d, 1H), 6.78–6.95 (m, 5H), 7.00 (d, 1H), 7.06–7.24 (m, 5H), 7.26–7.42 (m, 5H).

Ms (m/e, %): 540 (5, M+), 364 (100), 314 (15), 148 (53), 121 (87), 91 (90).

EXAMPLE 84

Cis-(2S,3S)-3-(2-methoxybenzyl)amino-2-phenyl-1-[4-(thiophen-2-yl)but-1-yl]

The title compound was prepared by a procedure similar to that of Example 2.

$C_{27}H_{34}N_2OS$, oil.

$^1H$ NMR (CDCl$_3$) δ 1.32–1.60 (m, 6H), 2.8–2.9 (m, 1H), 1.96–2.3 (m, 4H), 2.50–2.72 (m, 4H), 3.16–3.38 (m, 3H), 3.40 (s, 3H), 3.65–3.80 (m, 1H), 6.59–6.76 (m, 3H), 6.81–6.88 (m, 2H), 7.02–7.12 (m, 2H), 7.20–7.38 (m, 5H).

MS (m/e, %): 434 (60, M+), 271 (31), 258 (100), 121 (32), 91 (35).

The title compounds of Example 85–89 were prepared by a procedure similar to that described in Example 1.

EXAMPLE 85

Cis-3-(5-chloro-2-methoxybenzyl)amino-2-(3-fluorophenyl)piperidine dimesylate $C_{19}H_{22}ClFN_2O \cdot 2CH_3SO_3H$, hygroscopic solid, (34%).

$^1H$ NMR (CDCl$_3$) δ 1.40 (m, 1H), 1.60 (m, 1H), 1.78 (s, 2H), 1.87 (m, 1H), 2.09 (m, 1H), 2.79 (m, 2H), 3.25 (m, 1H), 3.36 (d, 1H), 3.51 (s, 3H), 3.62 (d, 1H), 3.87 (d, 1H, J=2Hz), 6.61 (d, 1H, J=8.7 Hz), 6.89–7.12 (m, 5H), 7.22–7.31 (m, 1H).

MS-FAB (m/e, %): 349 (100, M+), 351 (35), 178 (25), 155 (29), 119 (31).

EXAMPLE 86

Cis-3-(2,5-dimethoxybenzyl)amino-2-(3-methoxyphenyl)piperidine dihydrochloride $C_{21}H_{28}N_2O_3 \cdot 2HCl$, mp. 235°–237° C., (6%).

$^1H$ NMR (CDCl$_3$, free base) δ 1.42 (m, 1H), 1.60 (m, 1H), 1.83–2.20 (m, 4H), 2.72–2.87 (m, 2H), 3.27 (m, 1H), 3.40 (d, 1H), 3.43 (s, 3H), 3.65 (d, 1H), 3.72 (s, 3H), 3.77 (s, 3H), 3.86 (d, 1H), 6.58–6.70 (m, 2H), 6.73–6.88 (m, 3H), 7.18–7.28 (m, 2H).

MS-FAB (m/e, %): 357 (100, M+), 190 (18), 151 (26), 119 (29).

EXAMPLE 87

Cis-3-(2,5-dimethoxybenzyl)amino-1-ethyl-2-(3-fluorophenyl)piperidine dimesylate $C_{22}H_{29}FN_2 \cdot 2CH_3SO_3H$, oil. $^1H$ NMR (CDCl$_3$, free base) δ 0.97 (t, 3H), 1.5 (m, 2H), 1.86–2.15 (m, 5H), 2.55–2.70 (m, 2H), 3.23 (m, 1H), 3.32 (s, 1H), 3.40 (d, 1H), 3.50 (s, 3,H), 3.68 (d, 1H), 3.70 (s, 3H), 6.58–6.70 (m, 3H), 6.93 (m, 1H), 7.10 (dd, 2H), 7.25 (m, 1H).

MS-FAB (m/e, %): 373 (100, M+), 359 (10), 206 (46).

EXAMPLE 88

Cis-3-(5-chloro-2-methoxybenzyl)amino-2-(3-methoxyphenyl)piperidine dihydrochloride $C_{20}H_{25}ClN_2O_2 \cdot 2HCl$, mp. 256°–259° C., (25%).

$^1H$ NMR (CDCl$_3$, free base) δ 1.40 (m, 1H), 1.58 (m, 1H), 1.80–2.15 (m, 4H), 2.78 (m, 2H), 3.25 (m, 1H), 3.32 (d, 1H), 3.46 (s, 3H), 3.63 (d, 1H), 3.75 (s, 3H), 3.85 (d, 1H), 6.58 (d, 1H), 6.75–6.88 (m, 3H), 6.95 (d, 1H), 7.08 (dd, 1H), 7.20 (t, 1H).

$^{13}C$ NMR (CDCl$_3$, free base) δ 20.1, 28.2, 46.1, 47.6, 54.7, 55.0, 55.1, 63.9, 110.8, 111.1, 112.8, 118.5, 124.8, 127.2, 129.13, 129.18, 130.2, 143.9, 156.0, 159.6.

EXAMPLE 89

Cis-3-(5-chloro-2-methoxybenzyl)amino-2-(3-chlorophenyl)piperidine dihydrochloride $C_{19}H_{22}Cl_2N_2O \cdot 2HCl$, mp. 270°–273° C., (6%).

$^1H$ NMR (D$_6$-DMSO, 2HCl salt) δ 1.39–1.65 (m, 3H), 1.87 (m, 4H), 2.13 (d, 1H), 2.77 (t, 2H), 3.21–3.66 (m, 6H), 3.84 (s, 1H), 6.60 (d, 1H, J=8.7 Hz), 6.94 (d, 1H, J=2.6 Hz), 7.07–7.27 (m, 5H).

EXAMPLE 90

(+)-(2S,3S)-3-Amino-2-phenylpiperidine

In a bottle were placed 10 g of 10% palladium-carbon, 100 ml of methanol, 150 ml of ethanol, 3.5 ml of concentrated hydrochloric acid and 5 g of the hydrochloride salt of the title compound of Example 64. The mixture was shaken under hydrogen (40 p.s.i.) overnight, 5 g of additional catalyst was added to the system and the mixture was shaken under hydrogen for 3 days. The mixture was diluted with water, filtered through diatomaceous earth (Celite (trademark)) and the Celite (trademark) was rinsed with H$_2$O. The filtrate wa concentrated to remove most of the alcohol, the remaining liquid was extracted with chloroform and the chloroform extracts were dried (sodium sulfate) and concentrated to obtain 2.16 g of the title compound.

$[\alpha]_D$ (HCl salt) = +62.8° (C=0.46, MeOH).

$^1H$ NMR (CDCl$_3$) δ 1.68 (m, 4H), 2.72 (m, 1H), 2.95 (m, 1H), 3.16 (m, 1H), 3.80 (d, 1H, J=3), 7.24 (m, 5H).

HRMS Calc'd for $C_{11}H_{16}N_2$:176.1310. Found: 176.1309. Calc'd for $C_{11}H_{16}N_2 \cdot 2HCl \cdot 1/3H_2O$: C, 51.78; H, 7.36; N, 10.98. Found: C, 51.46; H, 7.27; N, 10.77.

EXAMPLE 91

(+)-(2S,3S)-3-(2,5-Dimethoxybenzyl)amino-2-phenylpiperidine

Under a nitrogen atmosphere in a round-bottom flask were placed 600 mg (3.4 mmol) of (+)-(2S,3S)-3-amino-2-phenylpiperidine, 8 ml of acetic acid and 622 mg (3.7 mmol) of 2,5-dimethoxybenzaldehyde, and the mixture was stirred for 30 minutes. To the system was added 1.58 g (7.5 mmol) of sodium triacetoxyborohydride, and the mixture was stirred at room temperature overnight. The mixture was concentrated, basified with 1 M aqueous sodium hydroxide and extracted with methylene chloride. The methylene chloride extracts were washed with water and extracted with 1 M aqueous hydrochloric acid. The hydrochloric acid extracts were basified with 1 M aqueous sodium hydroxide and extracted with methylene chloride. The methylene chloride extracts were dried (sodium sulfate) and concentrated to obtain 528 mg of colorless oil. The oil was dissolved in methylene chloride, and ether saturated with hydrogen chloride was added to the solution. The resulting white solid was collected by filtration and stirred in isopropanol at 60° C. for 2 hours. Filtration afforded 414 mg of the title compound as its hydrochloride. Additional material (400 mg) was obtained by extracting the initial basic layer with additional methylene chloride, drying (sodium sulfate) and concentration. [α]$_D$ ((HCl salt)= +60.5° (c=0.58, CH$_3$OH).

$^1$H NMR (CDCl$_3$) δ 1.38 (m, 1H), 1.58 (m, 1H), 1.88 (m, 1H), 2.13 (m, 1H), 2.78 (m, 2H), 3.25 (m, 1H), 3.36 (d, 1H), J=18), 3.44 (s, 3H), 3.62 (d, 1H, J=18), 3.72 (s, 3H), 3.88 (d, 1H, J=3), 6.62 (m, 3H), 7.24 (m, 5H). Mass spectrum: m/z 326 (parent). Calc'd for C$_{20}$H$_{26}$N$_2$O$_2$·2HCl·0.25H$_2$O: C, 59.48; H, 7.11; N, 6.93. Found: C, 59.33; H, 6.91; N, 7.23.

EXAMPLE 92

3-(2-Methoxy-5-methylbenzyl)amino-2-phenylpiperidine

A.

3-(2-Methoxy-5-methylbenzyl)amino-2-phenylpyridine

Under a nitrogen atmosphere in a round-bottom flask were placed 1.5 g (10 mmol) of 2-methoxy-5-methylbenzaldehyde and 22 ml of acetic acid. To the system, cooled in an ice bath, was added 3.6 g (17 mmol) of sodium triacetoxyborohydride in portions. The mixture was stirred at room temperature overnight. The reaction mixture was concentrated and partitioned between aqueous sodium hydroxide and dichloromethane. The layers were separated, the aqueous phase was extracted with dichloromethane and the combined organic fractions were dried (sodium sulfate) and concentrated to obtain 2.5 g of a brown oil. The crude product was purified by flash column chromatography using 5:1 hexanes/ethyl acetate as the eluant to obtain 1.65 g of the title compound as a yellow oil.

$^1$H NMR (CDCl$_3$) δ 2.22 (s, 3H), 3.72 (s, 3H), 4.24 (d, 2H, J=4), 4.73 (broad t, 1H), 6.70 (d, 1H, J=5), 7.0 (m, 4H), 7.33 (m, 1H), 7.44 (m, 2H), 7.59 (d, 2H), J=4), 7.99 (d, 1H, J=1).

B.

3-(2-Methoxy-5-methylbenzyl)amino-2-phenylpiperidine

In a bottle were placed 600 mg (1.97 mmol) of the title compound of Example 92A, 32 ml of ethanol, 118 μl (2.07 mmol) of acetic acid and 30 mg of platinium oxide. The mixture was shaken under hydrogen (ca. 40 p.s.i) for ca. 30 hours. During this period, additional (270 mg) platinium oxide and acetic acid (~18 ml) were added to the system. The reaction mixture was filtered through diatomaceous earth (Celite (trademark)), the filter cake was washed with ethanol and the filtrate was concentrated. The residue was partitioned between dichloromethane and 1 M aqueous sodium hydroxide. The layers were separated and the aqueous phase was extracted with dichloromethane. The combined organic fractions were dried (sodium sulfate) and concentrated to obtain 540 mg of yellow oil. This oil was partitioned between dichloromethane and 1 M aqueous hydrogen chloride, the layers were separated and the organic phase was extracted with 1 M hydrochloric acid. The combined aqueous extracts were washed with dichloromethane and were made basic with 1 M aqueous sodium hydroxide. The aqueous solution was extracted with dichloromethane, and the extracts were dried (sodium sulfate) and concentrated. The resulting oil was purified by flash column chromatography using 4.5–5% methanol/chloroform as the eluant to obtain 110 mg of the title compound, which was converted to its hydrochloride salt, mp 245°–247° C.

M.P. 245°–247° C.

$^1$H NMR (CDCl$_3$) δ 1.30–1.42 (m, 1H), 1.48–1.98 (m, 2H), 2.04–2.16 (m, 1H), 2.18 (s, 3H), 2.68–2.70 (m, 2H), 3.18–3.30 (m, 1H), 3.35 d, 1H, J=12), 3.40 (s, 3H), 3.58 (d, 1H, J=12), 3.85 (d, 1H, J=3), 6.53 (d, 1H, J=8), 6.71 (d, 1H, J=2), 6.88 (dd, 1H, J=4,10), 7.14–7.26 (m, 5H). HRMS Calc'd for C$_{20}$H$_{26}$N$_2$O:310.2041. Found: 310.2024. Anal. Calc'd for C$_{20}$H$_{26}$N$_2$O·2HCl·1.2H$_2$O: C, 59.31; H, 7.56; N, 6.92. Found: C, 59.31; H, 7.40; N, 6.85.

EXAMPLE 93

(2S,3S)-1-(3-Cyanoprop-1-yl)-3-(2-methoxybenzyl)amino-2-phenylpiperidine

The title compound was prepared by a procedure analogous to that of Example 2, replacing allyl bromide with 4-bromobutyronitrile.

M.P. 63°–67° C. (dec).

$^1$H NMR (CDCl$_3$) δ 1.40 (m, 2H), 1.80 (m, 6H), 2.12 (m, 1H), 2.28 (m, 1H), 2.52 (m, 2H), 3.08 (m, 1H), 3.21 (d, 1H, J=3), 3.34 (d, 1H, J=13), 3.40 (s, 3H), 3.60 (d, 1H, J=13), 6.58 (d, 1H, J=9), 6.68 (t, 1H, J=6), 6.78 (d, 1H, J=6), 7.02 (t, 1H, J=9), 7.20 (m, 5H). Mass spectrum: m/z 363 (parent).

EXAMPLE 94

(2S, 3S)-1-(4-Aminobut-1-yl)-3-(2-methoxybenzyl)amino-2-phenylpiperidine

The title compound of Example 93 (1.9 g) was dissolved in 10 ml of acetic acid in a bottle. To the system was added 1.9 g of 5% platinum/carbon (60% water), and the mixture was shaken under hydrogen (40 p.s.i.) for 4 hours. The mixture was diluted with ethanol, filtered through diatomaceous earth (Celite (trademark)) and the filtrate was concentrated. Saturated aqueous sodium bicarbonate was added to the residue until the pH of the mixture was ca. 8, and the mixture was extracted with chloroform. The chloroform extracts were dried (sodium sulfate) and concentrated to obtain 1.6 g of the title compound as an oil.

$^1$H NMR (CDCl$_3$) δ 1.50 (m, 8H), 2.02 (m, 3H), 2.52 (m, 3H), 3.18 (m, 1H), 3.26 (d, 1H, J=3), 3.32 (d, 1H, J=15), 3.43 (s, 3H), 3.64 (d, 1H, J=15), 4.77 (br s, 2H), 6.60 (d, 1H, J=9), 6.71 (t, 1H, J=6), 6.82 (d, 1H, J=6), 7.07 (t, 1H, J=9), 7.26 (m, 5H). Mass spectrum: m/z 367 (parent).

EXAMPLE 95

(2S, 3S)-3-(2-Methoxybenzyl)amino-1-[4-(2-naphthamidobut-1-yl)]-2-phenylpiperidine Under a nitrogen atmosphere in a round-bottom flask were placed 100 mg (0.27 mmol) of the title compound of Example 94 and 0.5 ml of methylene chloride, and the system was cooled in an ice bath. To the system was added 38 μl (0.27 mmol) of 2-naphthoyl chloride, and the mixture was stirred for 20 minutes. The mixture was poured into saturated aqueous sodium bicarbonate and extracted with chloroform. The chloroform extracts were dried (sodium sulfate) and concentrated to obtain 150 mg of an oil. The crude product was purified by flash column chromatography (6 g of silica gel) using 1:10 methanol/chloroform as the eluant to obtain 71 mg of the title compound, which was converted to its hydrochloride salt.

M.p. 105°–107° C. (dec.)

$^1$H NMR (CDCl$_3$) δ 1.50 (m, 6H), 1.70 (m, 2H), 2.04 (m, 3H), 2.60 (m, 2H), 3.22 (m, 1H), 3.30 (d, 1H, J=1), 3.40 (m, 5H), 3.68 (d, 1H, J=15), 6.28 (br s, 1H), 6.61 (d, 1H, J=9), 6.72 (t, 1H, J=6), 6.84 (d, 1H, J=6), 7.08 (t, 1H, J=9), 7.26 (m, 5H), 7.52 (m, 2H), 7.82 (m, 4H), 8.22 (s, 1H). Mass spectrum: m/z 521 (parent).

EXAMPLE 96

(2S,3S)-3-(2-(Methoxybenzyl)amino-1-[(N-naphth-2-ylmethyl)-4-aminobut-1-yl)]-2-phenylpiperidine The title compound of Example 95 is treated with borane dimethylsulfine, employing conditons analogous to those described in Example 1B, to obtian the title compound.

EXAMPLE 97

(2RS, 3RS)1-(5-carboethoxypent-1-yl)-3-(2-methoxybenzyl)amino-2-phenylpiperidine The title compound was prepared by a procedure analogous to that described in Example 2, replacing allyl bromide with ethyl 6-bromohexanoate.

M.p. 80°–95° C.

$^1$H NMR (CDCl$_3$) δ 1.12 (m, 5H), 1.42 (m, 6H), 1.72 (m, 1H), 1.98 (m, 3H), 2.16 (t, 2H, J=7), 2.46 (m, 1H), 2.54 (m, 1H), 3.15 (m, 1H), 3.23 (m, 1H, J=3), 3.30 (d, 1H, J=15), 3.41 (s, 3H), 3.60 (d, 1H, J=15), 4.02 (q, 2H, J=6), 6.58 (d, 1H, J=9), 6.78 (t, 1H, J=6), 6.80 (d, 1H, J=6), 7.04 (t, 1H, J=9), 7.22 (m, 5H). Mass spectrum: m/z 438 (parent).

EXAMPLE 98

(2RS,3RS)-1-(6-Hydroxyhex-1-yl)-3-(2-methoxybenzyl)amino-2-phenylpiperidine

Under a nitrogen atmosphere in a round-bottom flask were placed 95 mg (0.22 mmol) of the title compound of Example 97 and 1 ml of THF. The system was cooled in an ice/acetone bath, 0.44 ml (0.44 mmol) of 1M lithium aluminum hydride in ether was added to the system and the mixture was stirred fro 10 minutes. The cold bath was removed, the mixture was stirred at room temperature for 20 minutes and the cold bath was replaced. The the system was added cautiously ca. 0.4 ml of 2M aqueous sodium hydroxide, and the mixture was stirred at room temperatre for 20 minutes. Sodium sulfate was added tothe system, the mixture was stirred for 30 minutes, solides were removed by suction filtration and the filtrate was concentrated. The crude material was purified by flash column chromatography (5 g of silica gel) usign 3:47 methanol/chloroform as the eluant to obtain 49 mg of the title compound.

M.p. (HCl salt) 67°–68° C.(dec).

$^1$H NMR (CDCl$_3$) δ 1.18 (m, 4H), 1.42 (m, 4H), 1.72 (m, 1H), 2.00 (m, 5H), 2.50 (m, 2H), 3.16 (m, 1H), 3.23 (d, 1H, J=3), 3.30 (d, 1H, J=15), 3.41 (s, 3H), 3.52 (t, 2H, J=6), 3.62 (d, 1H, J=15), 6.58 (d, 1H, J=9) 6.69 (t, 1H, J=6), 6.81 (d, 1H, J=6), 7.05 (t, 1H, J=9), 722 (m, 5H). Mass spectrum: M/z 396 (parent).

EXAMPLE 99

(2S,3S)-1-(5-Carboxypentyl)-3-(2-methoxybenzyl)amino-2-phenylpiperidine (2S, 3S)-1-(5-Carboethoxypentyl)-3-(2-methoxybenzyl) amino-2-phenylpiperidine was prepared by the process of Example 97, utilizign the single enantiomer (2S,3S)-3-(2-methoxybenzyl)amino-2-phenylpiperidine instead of the corresponding racemate. In a round-bottom flask were placed 250 mg of this ester and 8 ml of 4M aqueous hydrochloric acid. The reaction mixture was heated at 60° C. for 2 hours and concentrated. The crude product was triturated with ether and with isopranol/ether to obtain the title compound as its hydrochloride salt.

$^1$H NMR (DMSO-d$_6$) δ 1.14 (m, 2H), 1.40 (m, 2H), 1.78 (m, 3H), 2.36 (m, 10H), 3.00 (m, 1H), 3.80 (m, 4H), 4.22 (m, 1H), 6.98 (m, 2H), 7.38 (m, 2H), 7.60 (m, 3H), 7.92 (m, 2H). HRMS calc'd for C$_{25}$H$_{34}$N$_2$O$_3$:410.2569. Found: 410.2546.

EXAMPLE 100

(2S,3S)-3-(2-Methoxybenzyl)amino-1-(N-methyl-5-carboxamidopent-1-yl)-2-phenylpiperidine Under a nitrogen atmosphere in a round-bottom flask were placed 75 mg (0.17 mmol) of the title compound of Example 99 and 0.5 ml of THF. To this stirring suspension were added 47 μl (0.34 mmol) of triethylamine and 54 mg (0.34 mmol) of N,N-carbonyldiimidazole. The reaction mixture was stirred for 30 minutes and concentrated. To the system was added 0.25 ml of 40% methylamine in water. The reaction mixture was stirred for 30 minutes and concentrated. To into a mixture of saturated aqueous sodium bicarbonate and chloroform. The mixture was extracted with chloroform and the chloroform extracts were dried (sodium sulfate) and concentrated. The crude produce was purified by flash column chromatography (5 g of silica gel) using 1:9 methanol/chloroform as the eluant to obtain 36 mg of the title compound as an oil.

$^1$H NRM δ 1.14 (m, 2H), 1.48 (m, 6H), 1.82 (m, 1H), 2.04 (m, 5H), 2.32 (m, 2H), 272 (d, 3H, J=5), 3.18 (m, 1H), 3.27 (d, 1H, J=3), 3.32 (d, 1H, J=15), 3.44 (s, 3H), 3.66 (d, 1H, J=15), 6.61 (d, 1H, J=9), 6/72 (t, 1H, J=6), 6.83 (d, 1H, J=6), 7.08 (t, 1H, J=9), 7.24 (m, 5H). Mass spectrum: m/z 423 (parent).

EXAMPLE 101

(2S,3S)-1-[4-(4-Fluorophenyl)-4-oxobut-1-yl]-3-(2-methoxybenzyl) amino-2-phenylpiperidine The title compound was prepared by a procedure analogous to that descibed in Example 2, replacing allyl bromide with 4-iodobutyl-4-fluorophenylketone.

M.p. 50°–60° C. (dec).

$^1$H NRM (CDCl$_3$) δ 1.46 (m, 2H), 1.96 (m, 6H), 2.58 (m, 2H), 2.84 (m, 2H), 3.24 (m, 1H), 3.30 (d, 1H, J=16), 6.62 (d, 1H, J=9), 6.72 (t, 1H, J=6), 6.84 (d, 1H, J=6), 7.08 (m, 3H), 7.27 (m, 5H), 7.92 (m, 2H). HRMS calc'd for C$_{29}$H$_{33}$N$_2$O$_2$F:460.2532. Found: 460.2528.

EXAMPLE 102

(2S,3S)-1-[4-(4-Fluorophenyl)-4-hydroxybut-1-yl]-3-(2-methoxybenzyl) amino-2-phenylpiperidine Under a nitrogen atmosphere in a round-bottom flask were place 569 mg (1.24 mmol) of the title compound of Example 101 and 2.5 ml of methanol, and the system was cooled in an ice bath. To the system was added 47 mg (1.24 mmol) of sodium borohydride in two poritons. The mixture was stirred for 30 minutes, 12 mg of sodium borohydride was added ad the mixture was stirred fo 30 minutes. To the system was added 0.5 ml of saturated aqueous sodium bicarbonate. the mixture was diluted with chloroform, allowed to warm to room temepratre and poured into a mixture of chloroform and saturated aqueous sodium bicarboate. The mixture was extracted with chloroform, dried (sodium sulfate) and concentrated to obtain 500 mg of an oil. The crude produce was purified by flash column chromatography (20 g of silica gel) usign 1:19 methanol/chloroform as the eluant to obtain 295 mg of the title compound, which was converted to its methanesulfonic acid salt.

$^1$H NRM (CDCl$_3$ $\delta$ 1.50 (m, 4H), 1.94 (m, 6H), 2.40, 2.55 (2m, 1H), 2.72 (m, 1H), 2.98, 3.40 (2m, 3H), 3.52 (s, 3H), 3.66 (m, 1H), 4.57, 471 (2m, 1H), 6.62 (d, 1H, J=9), 6.70 (m, 1H), 6.94 (m, 3H), 7.08 (m, 1H), 7.28 (m, 6H), 7.46 (m, 1H). HRMS calc'd for C$_{29}$H$_{35}$N$_2$O$_2$F:462.2678. Found: 462.2688.

EXAMPLE 103

(2S,3S)-1-(5,6-Dimethylmethylenedioxyhex-1-yl)-30(2-methoxybenzyl) amino-2-phenylpiperidine The title compound wa prepared by a procedure analogous to that described in Example 2, replacing allyl bromide with 5,6-dimethylenedioxy-1-methylsulfonyloxyhexane.

$^1$H NMR (CDCl$_3$ $\delta$ 1.34 (s, 3H), 1.40 (s, 3H), 1.44 (m, 4H), 1.76 (m, 2H), 2.00 (M, 3H), 2.50 (m, 2H), 3.17 (m, 1H), 3.25 (m, 1H), 3.32 (d, 1H, J=15), 3.44 (s, 3H), 3.48 (m, 2H), 3.60 (m, 1H), 3.98 (m, 4H), 6.58 (d, 1H, J=9), 6.70 (t, 1H, J=6), 6.80 (d, 1H, J=6), 7.05 (t, 1H, J=9), 7.24 (m, 5H0.

EXAMPLE 104

(2S,3S)-1-(5,6-Dihydroxyhes-1-yl)-3-(2-methoxybenzyl)amino-2-phenylpiperidine

In a round-bottom flask were placed 3.2 g of the title compound of Example 1-3 and 100 ml of a 1:1 mixture pf methanol and dichloromethane. To the system was added 50 ml of dichloromethane saturated with hydrogen chloride, and the reaciton mixture was allowed to stand at room temperature for 3 hours and concentrated. The residue was dissolved in hot isopropanol and ether was added. The solvent was poured off the resultign gum and discarded. The gum was triturated with hot isopropranol/ether and this solvent was saved. The resultign gum was scratched to form a solid (630 mg). The mother liquor was concentrated and the residual oil was triturated with hot isopropanol/ether and ether to obtian a solid (850 mg). Each of the lots of produce as stirred in 50 ml of either for 2 hour,, and the solvent was removed with a pipet. The latter solid was further purified by partitioning between dichloromethane and 1M aqueous sodium hydroxide, extracing the aqueous phase with dichloromethane, drying (sodium sulfate) and concentrating the combied organic fracitosn and treatign a dichloromethane solution of the residue with ethereal hydrogen chloride. This seqence afforded 710 mg of the title compound (hydrochloride) as a very hygroscopic off white solid.

$^1$H NRM (CDCl$_3$) $\delta$ 1.34 (m, 8H), 1.80 (m, 1H), 2.08 (m, 3H), 2.54 (m, 4H), 3.20 (m, 1H), 3.34 (m, 2H), 3.44 (s, 3H), 3.56 (m, 1H), 3.66 (d, 1H, J=12), 6.60 (d, 1H, J=9), 6.74 (t, 1H, J=6), 6.84 (d, 1H, J=6), 7.09 (t, 1H, J=9), 7.26 (m, 5H).

HRMS calc'd for C$_{25}$H$_{36}$N$_2$O$_3$:412.2726. Found: 412.2699.

The title compound of Examples 105 and 106 were prepared by a procedure similar to that of Example 1.

EXAMPLE 105

(2RS,3RS,5SR)-3-(2-Methoxbenzylamino)-5-methyl-2-phenylpiperidine

M.p. 179°–181° C. (HCl salt, dec.).

$^1$H NRM (CDCl$_3$) $\delta$ 7.20 (m, 6H), 7.00 (d, 1H, J=7 Hz), 6.76 (t, 1H, J=7 Hz), 6.66 (d, 1H, J=6 Hz), 3.97 (d, 1H, J=2 Ha), 3.64 (d, 1H, J=12 Hz), 3.51 (d, 1 H, J=12 hz), 3.48 (s, 3H), 2.84 (m, 3H), 1.78 (m, 3H), 1.13 (d, 3H, J=7 Hz). HRMS calc'd for C$_{20}$H$_{26}$N$_2$O: 310.2045. Found: 310.2101.

EXAMPLE 106

(2RS,3RD,5RS)-3-(2-Methoxybenzyamino)-5-methyl-2-phenylpiperidine

M.P. 248°–249° C. (HCl salt, dec).

$^1$H NRM (CDCl$_3$) $\delta$ 7.18 (m, 5H), 7.07 (t, 1H, J=7 Hz), 6.90 (d, 1H, J=7 Hz), 6.72 (t, 1H, J=7 Hz), 6.60 (d, 1H, J=7 Hz), 3.77 (d, 1 H, J=2 Hz), 3.60 (d, 1H, J=12 Hz), 3.38 (s, 3H), 3.34 (s, 1H, J=12 Ha), 3.14 (m, 1H), 2.77 (m, 1H), 2.32 (t, 1H, J=10 Hz), 2.02 ( m, 2H), 1.18 (m, 1H), 0.81 (d, 3H, J=6 Hz). HRMS CAlc'd for C$_{20}$H$_{26}$N$_2$O: 310.2045. Found: 310.2076. Calc'd for C$_{20}$H$_{26}$N$_2$O·2HCl·2/3H$_2$O: C, 60.75; H, 7.47; N, 7.09. Found: C, 60.78; H, 7.32; N, 6.84

EXAMPLE 107

Cis-3-(2,5-dimethoxybenzylamino)-1-[4-(4-fluorophenyl)-4-oxobut-1-yl ]-2-phenylpiperidine The title compound was prepared by a procedure similar to that described in Example 101.

$^1$H NMR (CDCl$_3$) $\delta$ 1.38 (m, 2H), 1.86 (m, 6H), 2.50 (m, 2H), 1.86 (m, 6H), 2.50 (m, 2H), 2.74 (m, 2H), 3.16 (s, 1H), 3.26 (m, 2H), 3.38 (s, 3H), 3.54 (m, 4H), 6.50 (m, 3H), 7.00 (m, 2H), 7.16 (m, 5H), 7.82 (m, 2H).

HRMS Calc'd for C$_{30}$H$_{35}$N$_2$FO$_3$:490.2629. Found: 490.2633. Calc'd for C$_{30}$H$_{35}$N$_2$O$_3$F·2CH$_3$SO$_3$H·4.75-H$_2$O: C, 50.01; H, 6.88: N, 3.64. Found: C, 49.93; H, 6.52; N, 3.56.

EXAMPLE 108

Cis-3-(4,5-difluoro-2-methoxybenzylamono)-2-phenyl-piperidien

The title compound was prepared by a procedure similar to that described in Example 91.

$^1$H NMR (CDCl$_3$) $\delta$ 1.30 (m, 1H), 1.62 (m, 2H), 1.96 (m, 1H), 2.68 (m, 2H), 3.18 (m, 2H), 3.32 (s, 3H), 3.44 d, 1H, J=14), 3.82 (d, 1H, J=3), 6.38 dd, 1H, J=6,12), 6.66 (dd, 1H, J=8,10), 7.16 (m, 5H).

HRMS Calc'd for C$_{19}$H$_{22}$N$_2$F$_2$O: 332.1697. Found: 332.1698. Calcd for C$_{19}$H$_{22}$N$_2$OF$_2$·2HCl·0.85H$_2$O: C, 54.25; H, 6.15; N, 6.66. Found: C, 54.26; H, 5.84; N, 6.94.

EXAMPLE 109

Cis-3-(2-chloro-4-fluorobenzylamino)-2-phenyl-piperidien

The title compound was prepared by a procedure similar to that described in Example 91.

$^1$H NMR (CDCl$_3$) $\delta$1.44 (m, 1H), 2.06 (m, 1H), 2.78 (m, 2H), 3.24 (m, 1H), 3.40 (d, 1H, J=12), 3.58 (d, 1H, J=12), 3.88 (d, 1H, J=3), 6.75 (m, 1H), 6.92 (m, 2H), 7.26 (m, 5H).

HRMS Calc'd for C$_{18}$H$_{20}$N$_2{}^{35}$ClF:318.1294. Found: 318.1280.

EXAMPLE 110

Cis-3-(2-ethoxybenzylamino)-2-phenylpiperidien

The title compound was prepared by a procedure similar to that described in Example 91.

$^1$H NRM (CDCl$_3$) δ1.10 (t, 3H, J=5), 1.40 (m, 1H), 1.62 (m, 1H), 1.90 (m, 1H), 2.14 (m, 1H), 2.80 (m, 2H), 3.27 (m, 1H), 3.38 (d, 1H, J=15), 3.69 (m, 3H), 3.86 (d, 1H, J=2), 6.64 (d, 1H, J=8), 6.78 (t, 1H, J=6), 6.94 (d, 1H, J=6), 7.12 (t, 1H, J=8), 7.24 (m, 5H).

HRMS Calc'd for C$_{20}$H$_{26}$N$_2$O:310.2041. Found: 310.2045.

EXAMPLE 111

Cis-b 3-(2-hydroxybenzylamino)-2-phenylpiperidine

The title compound was prepared by a procedure similar to that described in Example 91.

$^1$H NMR (CDCl$_3$) δ 1.62 (m, 3H), 2.10 (m, 1H), 2.79 (m, 1H), 2.92 (m, 1H), 3.20 (m, 1H), 3.48 (s, 2H), 3.82 (d, 1H, J=2), 6.72 (m, 3H), 7.08 (m, 1H), 7.36 (m, 5H).

HRMS Calc'd for C$_{18}$H$_{22}$N$_2$O:282.1732. Found: 282.1724. Calcd for C$_{18}$H$_{22}$N$_2$O·2HCl·2H$_2$O: C, 55.26, H, 7.20; N, 7.16. Found: C, 55.13; H, 7.12; N, 6.84.

EXAMPLE 112

Cis-3-(3,5-difluoro-2-methoxybenzylamino)-2-phenylpiperidine

The compound was prepared by a procedure similar to that described in Example 91.

$^1$H NMR (CDCl$_3$) δ 1.45 (m, 1H), 1.64 (m, 1H), 1.86 (m, 1H), 2.08 (m, 1H), 2.80 (m, 2H), 3.24 (m, 1H), 3.44 (d, 1H, J=15), 3.54 (d, 1H, J=15), 3.68 (s, 3H), 3.90 (d, 1H, J=3), 6.57 (dd, 1H, J=8, 9), 6.69 (dd, 1H, J=9, 12), 7.28 (m, 5H).

HRMS Calc'd for C$_{19}$H$_{22}$N$_2$OF$_2$:332.1698. Found: 332.1700. Calc'd for C$_{19}$H$_{22}$N$_2$OF$_2$·2HCl:C, 56.30; H, 5.97; N, 6.92. Found: C, 56.17; H, 5.84; N, 6.59.

EXAMPLE 113

Cis-3-(2-chloro-6-fluorobenzylamino)-2-phenylpiperidine

The title compound was prepared by a procedure similar to that described in Example 91.

$^1$H NMR (CDCl$_3$) δ 1.40 (m, 1H), 1.66 (m, 1H), 1.90 (m, 1H), 2.15 (m, 1H), 2.78 (m, 2H), 3.26 (m, 1H), 3.68 (d, 2H, J=18), 3.72 (d, 1H, J=18), 6.82 (m, 1H), 7.04 (m, 2H), 7.22 m, 5H).

HRMS Calc'd for C$_{18}$H$_{20}$N$_2$ClF·2HCl·2/3H$_2$O: C, 53.56; H, 5.83; N, 6.95. Found: C, 53.63; H, 5.53; N, 6.83.

EXAMPLE 114

(2S, 3S)-3-(5-chloro-2-methoxybenzylamino)-2-phenylpiperidine

The title compound was prepared by a procedure similar to that described in Example 91.

Mp 275°–277° C. (HCl salt).

$^1$H NMR (CDCl$_3$) δ 1.40 (m, 1H), 1.60 (m, 1H), 1.90 (m, 1H), 2.08 (m, 1H), 2.79 (m, 2H), 3.26 (m, 1H), 3.36 (d, 1H, J=15), 3.45 (s, 3H), 3.60 (d, 1H, J=15), 3.88 (d, 1H, J=3), 6.56 (d, 1H, J=8), 6.92 (d, 1H, J=3), 7.06 (dd, 1H, J=3,8), 7.28 (m, 5H).

Mass spectrum: m/z 330 (parent).

EXAMPLE 115

Cis-3-(5-chloro-2-methoxybenzylamino)-2-phenylpiperidine

The title compound was prepared by a procedure similar to that described in Example 91.

$^1$H NMR (CDCl$_3$δ 1.37 (m, 1H), 156 (m, 1H), 1.86 (m, 1H), 2.06 (m, 1H), 2.76 (m, 2H), 3.23 (m, 1H), 3.32 (d, 1H, J=15), 3.42 (5, 3H), 3.58 (d, 1H, J=15), 3.85 (d, 1H, J=3), .654 (d, 1H, J=8), 6.90 (d, 1H, J=3), 7.04 (dd, 1H, J=3,8), 7.24 (m, 5H),

EXAMPLE 116

(2S,3S)-1-(5-acetamidopent-1-yl)-3-(2-methoxybenzylamino)-2-phenylpiperidine

The title compound was prepared by a procedure similar to that described in Example 95.

$^1$NMR (CDCl$_3$) δ 1.14 (m, 2H), 1.40 (m, 5H), 1.86 (m, 1H), 1.91 (s, 3H), 2.00 (m, 3H), 2.52 (m, 2H), 3.12 (m, 3H), 3.22 (d, 1H, J=15), 6.60 (d, 1H, J=9), 6.70 (t, 1H, J=9), 6.82 (d, 1H, J=6), 7.06 (t, 1H, J=6), 7.22 (m, 5H).

HRMS Calc'd for C$_{26}$H$_{37}$N$_3$O$_2$:423.2885. Found: 423.2869.

EXAMPLE 117

(2S,3S)-1-(5-aminopent-1-yl)-3-(2-methoxbenzylamino)-2-phenylpiperidine

The title compound was prepared by a procedure similar to that described in Example 94.

$^1$H NMR (CDCl$_3$) δ 1.30 (m, 7H), 1.76 (m, 3H), 2.02 (m, 3H), 2.54 (m, 3H), 3.02 (m, 1H), 3.28 (d, 1H, J=3), 3.36 (d, 1H, J=15), 3.46 (s, 3H), 3.66 (d, 1H, J=15), 6.60 (d, 1H, J=6), 6.72 (t, 1H, J=6), 6.83 (d, 1H, J=6), 7.08 (t, 1H, J=6), 7.24 (m, 5H).

HRMS Calc'd for C$_{24}$H$_{35}$N$_3$O:381.2780. Found: 381.2755.

EXAMPLE 118

(2S,3S)-1-(5-benzamidopent-1-yl)-3-(2-methoxybenzylamino)-2-phenylpiperidine

The title compound was prepared by a procedure similar to that described in Example 95.

$^1$H NRM δ 1.40 (m, 8H), 1.96 (m, 5H), 2.54 (m, 2H), 3.34 (m, 7H), 3.80 (m, 1H), 6.61 (d, 1H, J=9), 6.76 (t, 1H, J=6), 6.88 (d, 1H, J=9), 7.12 (t, 1H, J=6), 7.26 (m, 5H), 7.40 (m, 3H), 7.78 (d, 2H, J=6).

HRMS Calc'd for C$_{31}$H$_{39}$N$_3$O$_2$:485.3042. Found: 485.3001.

EXAMPLE 119

(2S,3S)-1-(6-hydroxyhex-1-yl)-3-(2-methoxybenzylamino)-2-phenylpiperidine

The title compund was prepared by a procedure similar to that described in Example 98.

$^1$H NRM (CDCl$_3$) δ 1.22 (m, 4H), 1.48 (m, 4H), 1.84 (m, 1H), 2.10 (m, 5H), 2.54 (m, 1H), 2.62 (d, 1H, J=3), 3.26 (m, 1H), 3.32 (d, 1H, J=3), 3.39 (, 1H, J=15), 3.48 (s, 3H), 3.60 (t, 2H, J=6), 3.70 (d, 1H, J=15), 6.66 (d, 1H, J=9), 6.78 (t, 1H, J=6), 6.89 (d, 1H, J=6), 7.14 (t, 1H, J=9), 7.28 (m, 5H).

HRMS Calc'd for C$_{25}$H$_{36}$N$_2$O$_2$:396.2777. Found: 396.2738.

EXAMPLE 120

(2S,3S)-1-(5-carboethoxypent-1-yl)-3-(2-methoxybenzylamino)-2-pheylpiperidine

The title compound ws prepared by a procedure similar to that described in Example 97.

$^1$H NMR (CDCl$_3$) δ 1.14 (m, 5H), 1.48 (m, 6H), 1.96 (m, 4H), 2.20 (t, 2H, J=7), 2.74 (m, 2H), 3.19 (m, 1H), 3.26 (d, 1H, J=3), 3.34 (d, 1H, J=15), 3.44 (s, 3H), 3.64 (d, 1H, J=15), 4.06 (q, 2H, J=6), 6.61 (d, 1H, J=9), 6.72 (t, 1H, J=6), 6.83 (d, 1H, J=6), 7.08 (t, 1H, J=9), 7.22 (m, 5H).

HRMS Calc'd for C$_{27}$H$_{38}$N$_2$O$_3$:438.2879. Found: 438.2839.

EXAMPLE 121

Cis-1-(5-hydroxypent-1-yl)-3-(2-methoxybenzylamino)-2-phenylpiperidine

The title compund was prepared by a procedure similar to that descirbed in Example 98.

$^1$H NMR (CDCl$_3$) δ 1.08 (m, 2H), 1.22 (m, 4H), 1.72 (m, 3H), 2.00 (m, 3H), 2.48 (m, 1H), 2.54 (m, 1H), 3.36 (m, 1H), 3.25 (d, 1H, J=3), 3.32 (d, 1H, J=15), 3.42 (s, 3H), 3.52 (t, 2H, J=6), 3.62 (d, 1H, J=15), 6.58 (d, 1H, J=9), 6.69 (t, 1H, J=6), 6.81 (d, 1H, J=6), 7.05 (t, 1H, J=9), 7.22 (m, 5H).

HRMS Calc'd for C$_{24}$H$_{34}$N$_2$O$_2$:382.2616. Found: 382.2565.

EXAMPLE 122

Cis-1-(4-carboethoxybut-1-yl)-3-(2-methoxybenzylamino)-2-phenylpiperidine

The title compound was prepared by a procedure similar to that described in Example 97.

$^1$H NMR (CDCl$_3$) δ 1.22 (t, 3H, J=6), 1.46 (m, 4H), 1.74 (m, 3H), 2.02 (m, 3H), 2.16 (m, 2H), 2.54 (m, 2H), 3.28 (m, 1H), 3.26 (m, 1H), 3.34 (d, 1H, J=15), 3.46 (s, 3H), 3.62 (d, 1H, J=15), 4.06 (q, 2H, J=6), 6.61 (d, 1H, J=9), 6.72 (t, 1H, J=6), 6.83 (d, 1H, J=6), 7.08 (t, 1H, J=9), 7.28 (m, 5H).

HRMS Calc'd for C$_{26}$H$_{36}$N$_2$O$_3$:424.2723. Found: 424.2734.

EXAMPLE 123

Cis -1-(5-carboxypent-1-yl)-3-(2-methoxybenzylamino)-2-phenylpiperidine

The title compound was prepared by a procedure similar to that described in Example 99.

M.p. 53°–65° C.

$^1$H NMR (DMSO-d$_6$) δ 1.10 (m, 2H), 1.36 (m, 2H), 1.70 (m, 3H), 2.30 (m, 10H), 2.96 (m, 1H), 3.70 (m, 2H), 3.90 (m, 2H), 4.20 (m, 1H), 6.98 (m, 2H), 7.38 (m, 2H), 7.60 (m, 3H), 7.90 (m, 2H). Mass spectrum: m/z 410 (parent).

EXAMPLE 124

Cis-1-(3-hydroxyprop-1-yl)-3-(2-methoxybenzylamnio)-2-phenylpiperidine

The title compound was prepared by a procedure similar to that described in Example 98.

M.p. 93°–96° C. (dec).

$^1$H NMR (CDCl$_3$) δ 1.34 (m, 3H), 2.00 (m, 4H), 2.65 (m, 1H), 2.76 (m, 1H), 3.31 (m, 3H), 3.38 (d, 1H, J=15), 3.51 (s, 3H), 3.62 (d, 1H, J=15), 3.74 (m, 2H), 6.64 (d, 1H, J=9), 6.73 (t, 1H, J=6), 6.88 (d, 1H, J=6), 7.08 (t, 1H, J=9), 7.30 (m, 5H).

Mass spectrum: m/z 354 (parent). Calc'd for C$_{22}$H$_{30}$N$_2$O$_2$·2HCl·2.65H$_2$O: C, 55.61; H, 7.90; N, 5.89. Found: C, 55.62; H, 7.75; N, 5.67.

EXAMPLE 125

Cis-1-(3-carboxyprop-1-yl)-3-(2-methoxybenzylamino)-2-phenylpiperidine

The title compound was prepared by a procedure similar to that described in Example 99.

M.p. 100°–105° C. (dec).

$^1$H NMR (DMSO-d$_6$) δ 1.92 (m, 3H), 2.20 (m, 6H), 3.46 (m, 4H), 3.78 (m, 3H), 4.00 (m, 3H), 6.94 (m, 2H), 7.36 (m, 2H), 7.56 (m, 3H), 7.86 (m, 2H).

Mass spectrum: m/z 382 (parent).

EXAMPLE 126

Cis-1-(2-carvboethoxyeth-1-yl)-3-(2-methoxybenzylamino)-2-phenylpiperidien

The title compound was prepared by a procedure similar to that described in Example 97.

M.p. 110°–112° C.

$^1$H NMR (CDCl$_3$) δ 1.18 (t, 3H, J=6), 1.46 (m, 2H), 1.62 (m, 1H), 2.08 (m, 3H), 2.26 (m, 1H), 2.42 9m, 2H), 2.60 (m, 1H), 2.90 (m, 1H), 3.16 (m, 1H), 3.36 (d, 1H, J=15), 3.45 (s, 3H), 3.66 (d, 1H, J=15), 4.04 (q, 2H, J=6), 6.62 (d, 1H, J=9), 6.74 (t, 1H, J=6), 6.85 (d, 1H, J=6), 7.08 (t, 1H, J=9) 7.28 (m, 5H).

Mass spectrum: m/z 396 (parent).

EXAMPLE 127

Cis-1-(3-carboethoxyprop-1-yl)-3-(2-methoxybenzylamino)-2-phenylpiperidine

The title compound was prepared by a procedure similar to that described in Example 97.

M.p. 75°–90° C.

$^1$H NMR (CDCl$_3$)δ 1.14 (t, 3H, J=6), 1.42 (m, 2H), 1.74 (m, 3H), 2.08 (m, 5H), 2.50 (m, 2H), 3.17 (m, 1H), 3.24 (d, 1H, J=3), 3.30 (d, 1H, J=1), 3.42 (s, 3H), 3.60 (d, 1H, J=15), 4.00 (q, 2H, J=6), 6.58 (d, 1H, J=9), 6.68 (t, 1H, J=6), 6.81 (d, 1H, J=6), 7.04 (t, 1H, J=9), 7.22 (m, 5H).

Mass spectrum: m/z 410 (parent).

EXAMPLE 128

Cis-1-(4-hydroxybut-1-yl)-3-(2-methoxybenzylamino)-2-phenylpiperidine

The title compound was prepared by a procedure similar to that described in Example 98.

$^1$H NMR (CDCl$_3$) δ 1.80 (m, 10H), 2.50 (m, 1H), 2.64 (m, 1H), 3.26 (m, 1H), .344 (m, 6H), 3.66 (M, 2H), 6.60 (d, 1H, J=9), 6.70 (t, 1H, J=9), 6.94 (d, 1H, J=9), 7.06 (t, 1H, J=6), 7.30 (m, 5H).

Mass spectrum: m/z 368 (parent). Calc'd for C$_{25}$H$_{34}$N$_2$O$_3$·2HCl·3/4 H$_2$O: C, 60.71; H, 7.86; N, 6.16. Found: C, 60.75; H, 7.55; N, 6.05.

EXAMPLE 129

Cis-1-(hex-1-yl)-3-(2-methoxybenzylamino)-2-phenylpiperidine

The title compound was prepared by a procedure similar to that described in Example 2.

M.p. 48°–50° C.

$^1$H NMR (CDCl$_3$) δ 0.85 (t, 3H, J=7), 1.15 (m, 7H), 1.50 (m, 3H), 2.05 (m, 4H), 2.55 (m, 1H), 2.60 (m, 1H), 3.30 (m, 1H), 3.50 (m, 5H), 3.80 (d, 1H, Jp32 15), 6.65 (d, 1H, J=7), 6.80 (t, 1H, J=7), 6.93 (d, 1H, J=7), 7.13 (t, 1H, J=7), 7.35 (m, 5H).

HRMS Calc'd for $C_{25}H_{36}N_2O$:380.2827. Found: 380.2808.

EXAMPLE 130

Cis-3-(2-methoxybenzylamino)-2-phenyl-1(6-phenyl-hex-1-yl)piperidine

The title compound was prepared by a procedure similar to that described in Example 2.

M.p. 48°–53° C.

$^1$H NMR (CDCl$_3$) δ 1.25 (m, 4H), 1.55 (m, 5H), 1.90 (m, 1H), 2.05 (m, 6H), 2.55 (m, 2H), 2.70 (m, 1H), 3.35 (M, 2H), 3.50 (s, 3H), 3.80 (m, 1H), 6.65 (s, 1H), 6.80 (s, 1H), 7.20 (m, 3H), 7.30 (m, 8H).

HRMS Calc'd for $C_{31}H_{40}N_2O \cdot 2HCl \cdot 3.2H_2O$: C, 63.40; H, 4.77; N, 7.95. Found: C, 63.40; H, 4.71; N, 7.89.

EXAMPLE 131

Cis-3-(2-methoxybenzylamino)-2-phenyl-1-(7-phenyl-hept-1-yl)piperidine

The title compound was prepared by a procedure similar to that described in Example 2.

M.p. 67°–77° C.

$^1$H NMR (CDCl$_3$) δ 1.15 (m, 5H), 1.50 (m, 4H), 1.90 (m, 1H), 2.10 (m, 7H), 2.50 (m, 3H), 3.40 (m, 2), 3.45 (s, 3H), 3.80 (m, 2H), 6.65 (t, 1H, J=8), 6.75 (t, 1H, J=8), 6.90 (d, 1H, J=8), 7.30 (m, 11H).

NRMS Calc'd for $C_{33}H_{44}NO$:470.3297. Found: 470.3281.

EXAMPLE 132

Cis-3(4-methoxybenzylamino)-2-phenylpiperidine

The title compound was prepared by a procedure similar to that described in Example 91.

M.p. 264°–266° C.

$^1$H NMR (CDCl$_3$) δ 128–140 (m, 1H), 1.44–1.88 (m, 2H), 1.92–2.02 (m, 1H), 2.64–2.84 (m, 2H), 3.10–3.22 (m, 1H), 3.19 (d, 1H, J=12), 3.39 (d, 1H, J=12), 3.70 (s, 3H), 3.81 (d, 1H, J=3), 6.65 (d, 2H, J=8), 6.83 (d, 2H, J=6), 7.12–7.28 (m, 5H).

HRMS Calc'd for $C_{19}H_{24}N_2O$:296.1885. Found: 296.1871. Anal. Calc'd for $C_{19}H_{24}N_2O \cdot 2HCl \cdot 0.6H_2O$: C, 60.03; H, 7.21; N, 7.37. Found: 60.08; H, 7.11; N, 7.45.

EXAMPLE 133

Cis-2-phenyl-3-(thien-2-ylmethylamino)piperidine

The title compound was prepared by a procedure similar to that described in Example 91.

M.p. 250°–242° C.

$^1$H NMR (CDCl$_3$) δ 130–1.40 (m, 1H), 1.46–1.52 (m, 1H), 1.68–1.86 (m, 1H), 1.92–2.00 (m, 1H), 2.64–2.78 (m, 1H), 2.84–2.92 (m, 1H), 3.12–3.22 (m, 1H), 3.44 (d, 1H, J=12), 3.54 (d, 1H, J=12), 3.81 (d, 1H, J=3), 6.53 (d, 1H, J=4), 6.72–6.80 (m, 1H), 7.02 (d, 1H, J=6), 7.12–7.30 (m, 5H).

HRMS CAlc'd for $C_{16}H_{20}N_2S$:272.1373. Found: 272.1327. Anal. Calc'd for $C_{16}H_{20}N_2S \cdot 2HCl \cdot 1.1H_2O$: C, 52.62, H, 6.67; N, 7.67. Found: C, 52.64; H, 6.38, N, 7.65.

EXAMPLE 134

Cis-3-(2-methoxynaphth-1-ylmethylamino)-2-phenyl-piperidine

The title compound was prepared by a procedure similar to that described in Example 91.

M.p. 222°–225° C.

$^1$H NMR (CDCl$_3$) δ 1.36–1.48 (m, 1H), 1.52–2.04 (m, 2H), 2.18–2.32 (m, 1H), 2.68–2.82 (m, 1H), 2.90 (d, 1H, J=3), 3.18–3.28 (m, 1H), 3.64 (s, 3H), 3.80 (d, 1H, J=12), 3.86 (d, 1H, J=4), 407 (d, 1H, J=12), 7.02–7.32 (m, 8H), 7.57 (d, 1H, J=8), 7.60–7.70 (m, 2H).

HRMS Calc'd for $C_{23}H_{26}N_2O$:346.2041. Found: 346.2043.

EXAMPLE 135

Cis-2-phenyl-3-(thien-3-ylmethylamino)piperidine

The title compound was prepared by a procedure similar to that described in Example 91.

M.p. 264°–267° C.

$^1$H NMR (CDCl$_3$) δ 1.30–1.40 (m, 1H), 1.46–1.64 (m, 1H), 1.70–1.88 (m, 1H), 1.92–2.02 (M, 1H), 2.68–2.78 (m, 1H), 2.80–2.88 (m, 1H), 3.14–3.22 (m, 1H), 3.31 (d, 1H, J=12), 3.48 (d, 1H, J=12), 3.84 (d, 1H, J=3), 6.65 (d, 1H, J=6), 6.72 (d, 1H, J=3), 7.04–7.10 (m, 1H), 7.14–7.28 (m, 5H).

HRMS Calc'd for $C_{16}H_{20}N_2S$:272.1342. Found: 272.1364. Anal. Calc'd for $C_{16}H_{20}N_2S \cdot 2HCl \cdot 0.6H_2O$:C, 53.96; H, 6.57; N, 7.87. Found: C, 53,97; H, 6.25; N, 7.77.

EXAMPLE 136

Cis-3-(2,5-difluorobenzylamino)-2-phenylpiperidine

The title compound was prepared by a procedure similar to that described in Example 91.

M.p. 274°–276° C.

$^1$H NMR (CDCl$_3$) δ 1.28–1.40 (m, 1H), 1.44–1.62 (m, 1H), 1.66–1.84 (m, 1H), 1.90–2.00 (m, 1H), 2.64–2.76 (m, 2H), 2.10–3.20 (m, 1H), 3.32 (d, 1H, J=12), 3.44 (d, 1H, J=12), 3.81 (d, 1H, J=3), 6.50–6.58 (m, 1H), 6.62–6.78 (m, 2H), 7.10–7.26 (m, 5H).

HRMS CAlc'd for $C_{18}H_{20}N_2F_2$:302.1590. Found: 302.1560. Anal. calc'd for $C_{18}H_{20}N_2F_2 \cdot 2HCl \cdot 0.2H_2O$:C, 57.06; H, 5.96; N, 7.39. Found: C, 56.94; H, 5.94; N, 7.37.

EXAMPLE 137

Cis-3-(3-methoxybenzylamino)-2-phenylpiperidine

The title compound was prepared by a procedure similar to that described in Example 92.

M.p. 243°–246° C. $^1$H NMR (CDCl$_3$) δ 1.32—1.42 (m, 1H), 1.48–1.90 (m, 2H), 1.96–2.04 (m, 1H), 2.68–2.78 (m, 1H), 2.85 (d, 1H, J=4), 3.16–3.26 (m, 1), 3.29 (d, 1H, J=12), 3.46 (d, 1H, J=12), 3.68 (s, 3H), 3.85 (d, 1H, J=3), 6.50–6.58 (m, 2H), 6.62–6.68 (m, 1H), 7.04 (t, 1H, J=8), 7.16–7.38 (m, 5H).

HRMS Calc'd for $C_{19}H_{24}N_2O$:296.1885. Found: 296.1873. Anal. CAlc'd for $C_{19}H_{24}N_2O \cdot 2HCl \cdot 0.3 H_2O$:C, 60.89; H, 6.75; N, 7.48. Found: C, 60.72; H, 6.84; N, 7.27.

EXAMPLE 138

(2S, 3S)-1-(4-oxo-4-phenylbut-1-yl)-3-(-2-methoxyben-zylamino)-2-phenylpiperidine The title compound was prepared by a procedure similar to that described in Example 101.

M.p. 217°–219° C.

$^1$H NMR (CDCl$_3$) δ 1.32–1.56 (m, 2H), 1.68–2.20 (m, 6H), 2.48–2.64 (m, 2H), 2.68–3.00 (m, 2H), 3.20–3.28 (m, 1H), 3.31 (d, 1H, J=4), 3.36 (d, 1H, J=15), 3.44 (s, 3H), 3.65 (d, 1H, J=15), 6.61 (d, 1H, J=7), 6.72 (t, 1H, J=6), 6.84 (t, 1H, J=6), 7.08 (t, 1H, J=8), 7.10–7.30 (m, 6H), 7.40 (t, 1H, J=6), 7.50 (d, 1H, J=6), 7.87 (d, 2H, J=6).

HRMS Calc'd for $C_{29}H_{34}N_2O_2$:442.2616. Found: 442.2577.

EXAMPLE 139

(2S, 3S)-1-(4-hydroxy-4-phenylbut-1-yl)-3-(2-methoxybenzylamino)-2-phenylpiperidine The title compound was prepared by a procedure similar to that described in Example 102.

M.p. 190°–194° C.

$^1$H NMR (CDCl$_3$(δ 1.40–2.24 (m, 10H), 2.42–2.66 (m, 1H), 2.74–2.84 (m, 1H), 3.02–3.14, 3.30–3.40 (2m, 1H), 3.44–3.62 (m, 5H), 3.66–3.82 (m, 1H), 6.68 (d, 1H, J=8), 6.74–6.82 (m, 1H), 6.98 (t, 1H, J=6), 7.08–7.18 (m, 1H), 7.20–7.62 (m, 10H).

HRMS Calc'd for $C_{29}H_{36}N_2O_2$:444.2772. Found: 444.2745. Anal. Calc'd for $C_{29}H_{36}N_2O_2 \cdot 2HCl \cdot 3H_2O$:C, 64.38; H, 7.56; N, 5.18. Found: C, 64.27; H, 7.31; N, 5.15

EXAMPLE 140

Cis-3-(2,5-dimethoxybenzylamino)-2-phenylpiperidine

The title compound was prepared by a procedure similar to that described in Example 91

M.p. 190°–194° C.

$^1$H NMR (CDCl$_3$) δ 1.28–1.40 (m, 1H), 1.48–1.92 (m, 2H), 2.02–2.14 (m, 1H), 2.66–2.80 (m, 2H), 3.14–3.24 (m, 1H), 3.32 (d, 1H, J=18H), 3.38 (s, 3H), 3.56 (d, 1H, J=18H), 3.66 (s, 3H), 3.83 (d, 1H, J=3H), 6.48–6.62 (m, 3H), 710-14 7.26 (m, 5H).

HRMS Calc'd for $C_{20}H_{26}N_2O_2$:326.1995. Found: 326.1959. Anal. Calc'd for $C_{20}H_{26}N_2O_2 \cdot 2HCl \cdot 0.3 - H_2O$:C, 59.34; H, 7.12; N, 6.92. Found: C, 59.33; H, 6.96; N, 6.76.

EXAMPLE 141

Cis-3-(3-fluoro-4-methoxybenzylamino)-2-phenylpiperidine

The title compound was prepared by a procedure similar to that described in Example 92.

M.p. 272°–274° C.

$^1$H NMR (CDCl$_3$) δ 1.34–2.04 (m, 4H), 2.68–2.82 (m, 2H), 3.12–3.26 m, 1H), 3.22 (d, 1H, J=12), 3.40 (d, 1H, J=12), 3.82 (s, 3H), 3.85 (d, 1H, J=4), 6.60–6.76 (m, 3H), 7.10–7.32 (m, 5H).

HRMS Calc'd. for $C_{19}H_{23}FN_2O$:314.1791. Found: 314.1773. Anal. Calc'd for $C_{19}H_{23}FN_2O \cdot 2HCl \cdot 1.1 - H_2O$:C, 56.05; H, 6.73; N, 6.88. Found: C, 55.96; H, 6.48; N, 6.71.

EXAMPLE 142

Cis-3-(5-fluoro-2-methoxybenzylamino)-2-phenylpiperidine

The title compound was prepared by a procedure similar to that described in Example 91.

M.p. 270°–272° C.

$^1$H NMR (CDCl$_3$) δ 1.30–1.42 (m, 1H), 1.48–2.12 (m, 3H), 2.64–2.82 (m, 2H), 3.12–3.26 (m, 1H), 3.32 (d, 1H, J=12), 3.42 (s, 3H), 3.56 (d, 1H, J=12), 3.84 d, 1H, J=3), 6.53 (dd, 1H, J=5, 10), 6.64 (dd, 1H, J=3, 8), 6.70–6.80 (m, 1H), 7.12–7.40 (m, 5H).

HRMS Calc'd for $C_{19}H_{23}FN_2O$:314.1791. Found: 314.1766. Anal. Calc'd for $C_{19}H_{23}FN_2O \cdot 2HCl \cdot 0.5 - H_2O$:C, 57.58; H, 6.61; N, 7.07. Found: C, 57.35; H, 6.36; N, 7.03.

EXAMPLE 143

Cis-3-(5-chloro-2-methoxybenzylamino)-2-phenylpiperidine

The title compound was prepared by a procedure similar to that described in Example 91.

M.p. 270°–273° C.

$^1$H NMR (CDCl$_3$) δ 1.32–1.42 (m, 1H), 1.50–2.12 (m, 3H), 2.68–2.82 (m, 2H), 3.18–3.28 (m, 1H), 3.32 (d, 1H, J=12), 3.42 (s, 3H), 3.58 (d, 1H, J=12), 3.85 (d, 1H, J=4), 6.54 (d, 1H, J=8), 6.90 (d, 1H, J=3), 7.04 (dd, 1H, J=3, 8), 7.12–7.32 (m, 5H).

HRMS Calc'd for $C_{19}H_{23}ClN_2O$:330.1495. Found: 330.1491. Anal. Calc'd for $C_{19}H_{23}ClN_2O$:330.1495. Found: 330.1491. Anal. calcd for $C_{19}H_{23}ClN_2O \cdot 2HCl \cdot 0.4H_2O$:C, 55.52; H, 6.33; N, 6.82. Found: C, 55,52; H, 6.33; N, 6.82. Found: C, 55.53; H, 6.10; N, 6.70.

EXAMPLE 144

Cis-3-(5-chloro-2-methoxybenzylamino)-1-(5,6-dihydroxyhex-1-yl)-2-phenylpiperidine The title compound was prepared by a procedure similar to that described in Example 104.

$^1$H NMR (CDCl$_3$) δ 1.34 (m, 8H), 1.78 (m, 1H), 2.00 (m, 3H), 2.54 (m, 2H), 3.32 (m, 3H), 3.44 (s, 3H), 3.54 (m, 3H), 6.52 (d, 1H, J=9), 6.80 (br s, 1H), 7.02 (m, 1H), 7.22 (m, 5H).

Mass spectrum: m/z 446 (parent).

EXAMPLE 145

Cis-1-(5,6-dihydroxyhex-1-yl)-3-(2,5-dimethoxybenzylamino)-2-phenylpiperidine

The title compound was prepared by a procedure similar to that described in Example 104.

$^1$H NMR (CDCl$_3$) δ 1.38 (m, 8H), 1.78 (m, 1H), 2.00 (m, 3H), 2.50 (m, 1H), 2.60 (m, 1H), 3.30 (m, 3H), 3.40 (s, 3H), 3.60 (m, 4H), 3.65 (s, 3H), 6.56 (m, 3H), 7.26 (m, 5H).

Mass spectrum: m/z 442 (parent).

EXAMPLE 146

Cis-2-phenyl-3-[2-(prop-2-yloxy)benzylamino]piperidine

The title compound was prepared by a procedure similar to that described in Example 91.

$^1$NMR (CDCl$_3$) δ 1.00 (m, 6H), 1.30 (m, 1H), 1.70 (m, 2H), 2.10 (m, 1H), 2.72 (m, 2H), 3.18 (m, 1H), 3.30 (m, 1H), 3.50 (m, 1H), 3.80 (br s, 1H), 4.06 (m, 1H), 6.66 (m, 2H), 6.90 (m, 1H), 7.05 (m, 1H), 7.20 (m, 5H).

HRMS Calc'd for $C_{21}H_{28}N_2O$:324.2197. Found: 324.2180. Calc'd for $C_{21}H_{28}N_2O \cdot 2HCl \cdot 1.66H_2O$:C, 59.02; H, 7.85; N, 6.55. Found: C, 59.07; H, 7.77; N, 6.69.

EXAMPLE 147

Cis-3-(3-fluoro-2-methoxybenzylamino)-2-phenylpiperidine

The title compound was prepared by a procedure similar to that described in Example 91.

$^1$H NMR (CDCl$_3$) δ 1.40 (m, 1H), 1.60 (m, 1H), 1.86 (m, 1H), 2.08 (m, 1H), 2.80 (m, 2H), 3.23 (m, 1H), 3.36 (m, 1H), 3.58 (m, 4H), 3.88 (m, 1H), 6.80 (m, 3H), 7.26 (m, 5H).

HRMS Calc'd for $C_{19}H_{23}N_2OF$:314.1794. Found: 314.1768. Calc'd for $C_{19}H_{23}N_2OF \cdot 2HCl \cdot 1.5H_2O$:C, 55.08; H, 6.80; N, 6.76. Found: C, 54.89; H, 6.48; N, 6.79.

EXAMPLE 148

Cis-3-(5-chloro-3-fluoro-2-methoxybenzylamino)-2-phenylpiperidine

The title compound was prepared by a procedure similar to that described in Example 91.

$^1$H NMR (CDCl$_3$) δ 1.42 (m, 1H), 1.54 (m, 1H), 1.80 (m, 1H), 2.06 (m, 1H), 2.78 (m, 2H), 3.20 (m, 1H), 3.42 (d, 1H), J=15), 3.58 (d, 1H, J=15), 3.64 (s, 3H), 3.86 (m, 1H), 6.66 (d, 1H, J=9), 6.91 (d, 1H, J=9), 7.26 (m, 5H).

HRMS Calc'd for C$_{19}$H$_{22}$N$_2$OClF:348.1401. Found: 348.1406.

EXAMPLE 149

Cis-3-(3-chloro-5-fluoro-2-methoxybenzylamino)-2-phenylpiperidine

The title compound was prepared by a procedure similar to that described in Example 91.

$^1$H NMR (CDCl$_3$) δ 1.44 (m, 1H), 1.58 (m, 1H), 1.80 (m, 1H), 2.06 (m, 1H), 2.80 (m, 2H), 3.22 (m, 1H), 3.42 (d, 1H, J=18), 3.54 (d, 1H, J=18), 3.66 (s, 3H), 3.88 (d, 1H, J=2), 6.55 (d, 1H, J=6), 6.92 (d, 1H, J=9), 7.26 (m, 5H).

HRMS Calc'd for C$_{19}$H$_{22}$N$_2$OClF:348.1401. Found: 348.1411. Calc'd for C$_{19}$H$_{22}$N$_2$OClF·2HCl·0.25H$_2$O:C, 53.53; H, 5.79; N, 6.57. Found: C, 53.58; H, 5.60; N, 6.41.

EXAMPLE 150

Cis-3-(3,5-dichloro-2-methoxybenzylamino)-2-phenylpiperidine

The title compound was prepared by a procedure similar to that described in Example 91.

$^1$H NMR (CDCl$_3$) δ 1.44 (m, 1H), 1.56 (m, 1H), 1.82 (m, 1H), 2.08 (m, 1H), 2.80 (m, 2H), 3.20 (m, 1H), 3.50 (m, 2H), 3.64 (s, 3H), 3.88 (m, 1H), 6.68 (s, 1H), 7.26 (m, 6H).

HRMS Calc'd for C$_{19}$H$_{22}$N$_2$OCl$_2$:364.1105. Found: 364.1105. Calc'd for C$_{19}$H$_{22}$N$_2$OCl$_2$·2HCl:C, 52.07; H, 5.52; N, 6.39. Found: C, 51.69; H, 5.50; N, 6.32.

EXAMPLE 151

Cis-3-(2-Methoxybenzylamino)-4-methyl-2-phenylpiperidine

The title compound was prepared by a procedure similar to that of Example 1.

$^1$H NMR (CDCl$_3$) δ 7.10 (m, 6H), (d, 1H, J=7 Hz), 6.68 (t, 1H, J=7 Hz), 6.68 (t, 1H, J=7 Hz), 6.55 (d, 1H, J=7 Hz), 3.97 (d, 1H, J=2 Hz), 3.56 (d, 1H, J=14 Hz), 3.34 (s, 3H), 3.28 (d, 1H, J=14 hz), 2.90 (m, 2H), 2.36 (s, 1H), 2.16 (s, 1H), 2.04 (s, 1H), 1.12 (m, 1H), 1.06 (d, 3H, J=6 Hz). HRMS Calc'd for C$_{20}$H$_{26}$N$_2$O:310.2045. Found: 310.2035.

EXAMPLE 152

(2S,3S)-1-(4-Oximino-4-phenylbut-1-yl)-3-(2-methoxybenzylamino)-2-phenylpiperidine Under a nitrogen atmosphere in a round bottom flask were placed 445 mg (1 mmol) of (2S,3S)-1-(4-oxo-4-phenylbut-1-yl)-3-(2-methoxybenzylamino-2-phenylpiperidine and 6 ml of ethanol. To the system were added 209 mg (3.2 mmol) of hydroxylamine hydrochloride and 417 mg (5 mmol) of sodium acetate in 6 ml of H$_2$O, and the mixture was stirred at room temperature overnight. The reaction mixture was concentrated and partitioned between chloroform and water. The layers were separated, and the aqueous phase was extracted two times with chloroform. The combined organic extracts were dried (sodium sulfate) and concentrated to 368 mg of gold oil. The crude product was purified by flash column chromatography using 7% in chloroform as the eluant to obtain 174 mg of the title compound as an oil.

$^1$H NMR (CDCl$_3$) δ 1.78 (m, 7H), 2.56 (m, 3H), 2.80 (m, 1H), 3.18 (m, 1H), 3.38 (m, 2H), 3.45 (s, 3H), 3.72 (m, 2H), 6.61 (d, 1H, J=8), 6.72 (t, 1H, J=6), 6.87 (d, 1H), J=6), 7.08 (t, 1H, J=8), 7.28 (m, 8H), 7.48 (m, 2H).

A sample of this compound was crystallized by slow evaporation from chloroform/methanol, and the structure was confirmed by single crystal x-ray analysis.

EXAMPLE 153

(2RS, 3RS, 6SR) and 2RS, 3RS, 6RS)-3-(2-Methoxy benzylamino)-6-methylpiperidine

The title compound was prepared by a procedure similar to that described in Example 63.

More polar isomer, R$_f$ 0.28 (1:9 MeOH/CH$_2$Cl$_2$). M.p. 274°–276° C. (HCl salt). $^1$H NMR (CDCl$_3$) δ 7.28–7.02 (m, 6H), 6.92 (d, 1H, J=6 Hz), 6.72 (t, 1H, J=6 Hz), 6.60 (d, 1H, J=8 Hz), 4.16 (d, 1H, J=3 Hz), 3.61 (d, 1H, J=14 Hz), 3.44–3.26 (m, 5H), 2.76 (d, 1H, J=4 Hz), 2.10–1.96 (m, 1H), 1.90–1.64 (m, 4H), 1.24~1.08 (m, 4H).

Less polar isomer, R$_f$~0.34 (1:9 MeOH/CH$_2$Cl$_2$). M.p. 203°–206° C. (HCl salt). $^1$H NMR (CDCl$_3$) δ 7.32–7.06 (m, 6H), 6.90 (d, 1H, J=6 Hz), 6.76 (t, 1H, J=6 Hz), 6.63 (d, 1H, J=7 Hz), 3.90 (d, 1H, J=3 Hz), 3.63 (d, 1H, J=14 Hz), 3.39 (s, 3H), 3.36 (d, 1H, J=14 Hz), 2.84–2.64 (m, 2H), 2.14–2.02 (m, 1H), 1.72–1.30 (m, 5H), 1.16 (d, 3H, J=6 Hz).

EXAMPLE 154

(2S,3S)-3-(2-Methoxybenzylamino)-1-[4-(4-methylphenylsulfonamido)but-1-yl]-2-phenylpiperidine The title compound was prepared by a procedure similar to that described in Example 95.

$^1$H NMR (CDCl$_3$) δ 1.40 (m, 6H), 1.85 (m, 1H), 1.96 (m, 5H), 2.39 (s, 3H), 2.60 (m, 1H), 2.83 (m, 1H), 2.83 (m, 1H), 3.14 (m, 1H), 3.26 (d, 1H, J=3), 3.41 (m, 4H), 3.68 (d, 1H, J=15), 6.60 (d, 1H, J=9), 6.69 (t, 1H, J=9), 6.80 (d, 1H, J=6), 7.06 (t, 1H, J=6), 7.22 (m, 7H), 7.68 (d, 2H, J=6). HRMS Calc'd for C$_{30}$H$_{39}$H$_3$O$_3$S:521.2708. Found: 521.2715.

EXAMPLE 155

(2S,3S)-1-(4-Cyanobut-1-yl)-3-(2-methoxybennzylamino)-2-phenylpiperidine

The title compound was prepared by a procedure similar to that described in Example 93.

M.P. 89°–81° C. (dec).

$^1$H NMR (CDCl$_3$) δ 1.48 (m, 5H), 1.90 (m, 5H), 2.20 (t, 2H, J=9), 2.52 (m, 2H), 3.18 (m, 1H), 3.06 (d, 1H, J=3), 3.32 (d, 1H, J=12), 3.40 (s, 3H), 3.68 (d, 1H, J=12), 6.58 (d, 1H, J=9), 6.70 (t, 1H, J=6), 6.82 (d, 1H, J=6), 7.06 (t, 1H J=9), 7.24 (m, 5H). HRMS Calc'd for C$_{24}$H$_{31}$N$_3$O:377.2467. Found: 377.2449.

EXAMPLE 156

Cis-3-(5-Chloro-2-methoxybenzylamino)-1-[4-(4-fluorophenyl)-4-oxobut-1-yl]-2-phenylpiperidine The title compound was prepared by a procedure similar to that described in Example 101.

¹H NMR (CDCl₃) δ 1.48 (m, 2H), 1.96 (m, 5H), 2.58 (m, 2H), 2.81 (m, 3H), 3.28 (m, 3H), 3.45 (s, 3H), 3.62 (d, 1H, J=15), 6.52 (d, 1H, J=9), 6.82 (d, 1H, J=3), 7.05 (m, 3H), 7.26 (m, 5H), 7.88 (m, 2H).

EXAMPLE 157

(2S,3S)-1-(4-Acetamidobut-1-yl)-3-(2-methoxybenzylamino)-2-phenylpiperidine

The title compound was prepared by a procedure similar to that described in Example 95.

¹H NMR (CDCl₃) δ 1.42 (m, 6H), 1.82 (m, 1H), 1.94 (s, 3H), 2.00 (m, 3H), 2.50 (m, 1H), 2.59 (m, 1H), 3.06 (m, 1H), 3.20 (m, 2H), 3.27 (d, 1H, J=3), 3.34 (d, 1H, J=15), 3.42 (s, 3H), 3.66 (d, 1H, J=15), 6.61 (d, 1H, J=9), 6.72 (t, 1H, J=6), 6.83 (d, 1H, J=6), 7.09 (t, 1H, J=9), 7.26 (m, 5H). Mass spectrum: m/z 409 (parent).

EXAMPLE 158

(2S,3S)-1-(4-Benzamidobut-1-yl)-3-(2-methoxybenzylamino)-2-phenylpiperdine

The title compound was prepared by a procedure similar to that described in Example 95.

M.p. 146°-150° C. (dec).

¹H NMR (CDCl₃) δ 1.46 (m, 6H), 1.72 (m, 1H), 1.98 (m, 3H), 2.52 (m, 2H), 3.16 (m, 1H), 3.25 (d, 1H, J=3), 3.30 (m, 3H), 3.38 (s, 3H), 3.68 (m, 1H), 6.24 (br s, 1H), 6.56 (d, 1H, J=9), 6.70 (t, 1H, J=6), 7.05 (t, 1H, J=9), 7.22 (m, 5H), 7.36 (m, 3H), 7.68 (d, 2H, J=6). HRMS Calc'd for $C_{30}H_{37}N_3O_2$:471.2885. Found: 471.2851.

EXAMPLE 159

Cis-2-(3,5-Dibromophenyl)-3-(2-methoxybenzylamino)-piperidine

The title compound was prepared by a procedure similar to that described in Example 1.

M.p.>240° C. (HCl salt).

¹H NMR (CDCl₃) δ 7.48 (s, 1H), 7.31 (s, 2H), 7.14 (t, 1H, J=6 Hz), 6.94 (d, 1H, J=6 Hz), 6.79 (t, 1H, J=6 Hz), 6.49 (d, 1H, J=6 Hz), 3.74 (s, 1H), 3.68 (d, 1H, J=12 Hz), 3.54 (s, 3H), 3.34 (d, 1H, J=12 Hz), 3.20 (m, 1H), 2.70 (m, 2H), 2.07 (m, 1H), 1.82 (m, 7H), 1.54 (m, 1H), 1.46 (m, 1H). HRMS Calc'd for $C_{15}H_{22}N_2OBr^{79}Br^{81}$:454.0078. Found: 454.0143.

EXAMPLE 160

(2S,3S)-3-(4,5-Difluoro-2-methoxybenzyl)amino-2-phenylpiperidine

The title compound was prepared by a procedure similar to that described in Example 91.

¹H NMR (CDCl₃) δ 1.36 (m, 1H), 1.55 (m, 1H), 1.84 (m, 1H), 2.02 (m, 1H), 2.72 (m, 2H), 3.20 (m, 1H), 3.26 (d, 1H), J=14), 3.42 (s, 3H), 3.52 (d, 1H, J=14), 3.84 (d, 1H, J=3), 6.42 (dd, 1H, J=6, 12), 6.70 (dd, 1H, J=8, 10), 7.20 (m, 5H).

Anal. Calc'd for $C_{19}H_{22}F_2N_2O \cdot 2HCl \cdot 0.55H_2O$: C, 54.96; H, 6.09; N, 6.75. Found: C, 54.65; H, 5.69; N, 6.74.

EXAMPLE 161

(2S,3S)-3-(2-Cyclopentyloxy-5-methoxybenzyl)amino-2-phenylpiperidine

The title compound was prepared by a procedure similar to that described in Example 91.

M.p. 217°-219° C. (HCl salt).

¹H NMR (CDCl₃) δ 1.66 (m, 13H), 2.14 (m, 1H), 2.82 (dt, 2H, J=12, 3), 2.92 (m, 1H), 3.14 (m, 2H), 3.54 (d, 1H, J=15), 3.72 (s, 3H), 3.90 (d, 1H, J=15), 4.50 (m, 1H), 6.64 (m, 3H), 7.30 (m, 5H).

HRMS Calc'd for $C_{24}H_{32}N_2O_2$: 380.2456. Found: 380.2457.

Anal. Calc'd for $C_{24}H_{32}N_2O_2 \cdot 2HCl \cdot H_2O$: C, 60.14; H, 7.70; N, 5.94. Found: C, 61.05; H, 7.67; N, 5.92.

EXAMPLE 162

(2S,3S)-3-(5-sec-Butyl-2-methoxybenzyl)amino-2-phenylpiperidine

The title compound was prepared by a procedure similar to that described in Example 91.

M.p. 260°-263° C. (HCl salt).

¹H NMR (CDCl₃) δ 0.8 (2t, 3H, J=6), 1.16 (2d, 3H, J=7), 1.5 (m, 4H), 1.9 (m, 1H), 2.12 (m, 1H), 2.46 (m, 1H), 2.8 (m, 3H), 3.28 (m, 1H), 3.42 (d, 1H, J=15), 3.44 (s, 3H), 3.66 (d, 1H, J=15), 3.90 (d, 1H, J=3), 6.60 (d, 1H, J=10), 6.78 (broad s, 1H), 6.92 (d, 1H, J=10), 7.3 (m, 5H).

HRMS Calc'd for $C_{23}H_{32}N_2O$: 352.2507. Found: 352.2525.

Anal. Calc'd for $C_{23}H_{32}N_2O \cdot 2HCl \cdot H_2O$: C, 62.29; H, 8.18; N, 6.32. Found C, 62.95; H, 7.62; N, 6.61.

EXAMPLE 163

(2S,3S)-3-(5-tert-Butyl-2-methoxybenzyl)amino-2-phenylpiperidine

The title compound was prepared by a procedure similar to that described in Example 91.

M.p. 262°-264° C. (HCl salt).

¹H NMR (CDCl₃) δ 1.22 (s, 9H), 1.38 (m, 2H), 1.90 (m, 1H), 2.14 (m, 1H), 2.80 (m, 2H), 3.26 (m, 1H), 3.36 (d, 1H, J=15), 3.44 (s, 3H), 3.62 (d, 1H, J=15), 3.86 (d, 1H, J=3), 6.60 (d, 1H, J=10), 7.00 (d, 1H, J=3), 7.12 (m, 1H), 7.26 (m, 5H).

HRMS Calc'd for $C_{23}H_{32}N_2O$: 352.2507. Found: 352.2512.

Anal. Calc'd for $C_{23}H_{32}N_2O \cdot 2HCl \cdot 0.5H_2O$: C, 63.58; H, 8.12; N, 6.45. Found C, 63.75; H, 8.00; N, 6.42.

EXAMPLE 164

(2S,3S)-3-(2-Cyclopentyloxybenzyl)amino-2-phenylpiperidine

The title compound was prepared by a procedure similar to that described in Example 91.

M.p. 230°-232° C. (HCl salt).

¹H NMR (CDCl₃) δ 1.75 (m, 13H), 2.14 (m, 1H), 2.80 (dt, 2H, J=12, 3), 2.90 (m, 1H), 3.28 (m, 1H), 3.36 (d, 1H, J=15), 3.60 (d, 1H, J=15), 3.88 (braod s, 1H), 4.58 (m, 1H), 6.74 (m, 2H), 6.84 (d, 1H, J=10), 7.12 (m, 1H), 7.30 (m, 5H).

HRMS Calc'd for $C_{23}H_{40}N_2O$: 350.2351. Found: 350.2332.

Anal. Calc'd for $C_{23}H_{30}N_2O \cdot 2HCl \cdot 2H_2O$: C, 60.12; H, 7.33; N, 6.10. Found C, 59.10; H, 7.19; N, 6.09.

EXAMPLE 165

(2S,3S)-3-(2-Acetamidobenzyl)amino-2-phenylpiperidine

The title compound was prepared by a procedure similar to that described in Example 91.

M.p. 187°-195° C. (HCl salt).

¹H NMR (CDCl₃) δ 1.52 (m, 1H), 1.61 (s, 3H), 1.70 (m, 1H), 2.10 (m, 2H), 2.80 (m, 2H), 3.18 (m, 1H), 3.32 (d, 1H, J=16), 3.54 (d, 1H, J=16), 3.89 (d, 1H, J=3), 6.88 (m, 2H), 7.26 (m, 7H).

HRMS Calc'd for $C_{20}H_{25}N_3O$: 323.1997. Found: 323.1972.

EXAMPLE 166

(2S,3S)-3-(5-Ethyl-2-methoxybenzyl)amino-2-phenyl-piperidine Hydrochloride

The title compound was prepared by a procedure similar to that described in Example 91.

$^1$H NMR (CDCl$_3$) δ 1.16 (t, 3H, J=9), 1.36 (m, 1H), 1.57 (m, 1H), 1.88 (m, 1H), 2.12 (m, 1H), 2.48 (q, 2H), 2.76 (m, 2H), 3.24 (m, 1H), 3.38 (m, 4H), 3.60 (d, 1H, J=12), 3.86 (d, 1H, J=3), 6.57 (d, 1H, J=6), 6.74 (d, 1H, J=3), 6.92 (dd, 1H, J=3,6), 7.24 (m, 5H).

HRMS Calc'd for $C_{21}H_{28}N_2O$: 324.2202. Found: 324.2184.

EXAMPLE 167

(2S,3S)-3-(4-Amino-5-chloro-2-methoxybenzyl)amino-2-phenylpiperidine Hydrochloride The title compound was prepared by a procedure similar to that described in Example 91.

M.p. 200°–203° C. (dec).

$^1$H NMR (free base, CDCl$_3$) δ 1.35 (m, 1H), 1.56 (m, 1H), 1.86 (m, 1H), 2.05 (m, 1H), 2.75 (m, 2H), 3.22 (m, 2H), 3.36 (s, 3H), 3.48 (d, 1H, J=12), 3.84 (d, 1H, J=2), 6.08 (s, 1H), 6.78 (s, 1H), 7.24 (m, 5H).

HRMS Calc'd for $C_{19}H_{24}ClN_3O$: 345.1604. Found: 345.1589.

EXAMPLE 168

(2S,3S)-3-(2-Methoxy-5-phenylbenzyl)amino-2-phenyl-piperidine Hydrochloride

The title compound was prepared by a procedure similar to that described in Example 91.

M.p. 238°–239° C. (dec).

$^1$H NMR (free base, CDCl$_3$) δ 1.38 (m, 1H), 1.60 (m, 1H), 1.88 (m, 1H), 2.12 (m, 1H), 2.80 (m, 2H), 3.23 (m, 1H), 3.45 (m, 4H), 3.70 (d, 1H, J=12), 3.86 (d, 1H, J=3), 6.70 (d, 1H, J=6), 7.34 (m, 12H).

HRMS Calc'd for $C_{25}H_{28}N_2O$: 372.2197. Found: 372.2172.

EXAMPLE 169

(2S,3S)-2-Phenyl-3-(quinoline-8-yl)methylpiperidine Hydrochloride

The title compound was prepared by a procedure similar to that described in Example 91.

M.P. 252°–253° C. (dec).

$^1$H NMR (free base, CDCl$_3$) δ 1.38 (m, 1H), 1.58 (m, 1H), 1.94 (m, 1H), 2.17 (m, 1H), 2.78 (m, 2H), 3.24 (m, 1H), 3.83 (d, 1H, J=3), 3.96 (d, 1H, J=15), 4.28 (d, 1H, J=15), 7.14 (m, 6H), 7.32 (m, 2H), 7.58 (t, 1H, J=4), 7.98 (d, 1H, J=6), 8.46 (m, 1H).

HRMS Calc'd for $C_{21}H_{23}N_3$: 317.1887. Found: 317.1883.

Anal. Calc'd for $C_{21}H_{33}N_3 \cdot 3HCl \cdot 1.33 H_2O$: C, 55.95; H, 6.40; N. 9.32. Found: C, 56.00; H, 6.28; N. 9.16.

EXAMPLE 170

(2S,3S)-3-(5-Heptyloxy-2-methoxybenzyl)amino-2-phenylpiperidine Hydrochloride

The title compound was prepared by a procedure similar to that described in Example 91.

M.p. 230° C. (dec).

$^1$H NMR (free base, CDCl$_3$) δ 0.90 (m, 2H), 1.38 (m, 10H), 1.76 (m, 4H), 2.12 (m, 1H), 2.80 (m, 2H), 3.26 (m, 1H), 3.38 (d, 1H, J=15), 3.42 (s, 3H), 3.62 (d, 1H, J=15), 3.82 (t, 2H, J=6), 3.88 (d, 1H, J=3), 6.62 (m, 3H), 7.28 (m, 5H).

HRMS Calc'd for $C_{26}H_{38}N_2O_2$: 410.2928. Found: 410.2953.

EXAMPLE 171

(2S,3S)-3-(2-Heptyloxy-5-methoxybenzyl)amino-2-phenylpiperidine Hydrochloride

The title compound was prepared by a procedure similar to that described in Example 91.

M.p. 212°–213° C. (dec).

$^1$H NMR (free base, CDCl$_3$) δ 0.90 (m, 3H), 1.60 (m, 13H), 2.12 (m, 1H), 2.80 (m, 2H), 3.26 (m, 1H), 3.36 (d, 1H, J=15), 3.62 (m, 6H), 3.86 (d, 1H, J=3), 6.60 (m, 3H), 7.23 (m, 5H).

HRMS Calc'd for $C_{26}H_{38}N_2O_2$: 410.2928. Found: 410.2912.

Anal Calc'd for $C_{26}H_{38}N_2O_2 \cdot 2HCl$: C, 64.59; H, 8.34; N, 5.80. Found: C, 64.34; H, 8.20; N, 5.75.

EXAMPLE 172

(2S,3S)-3-(5-Heptyl-2-methoxybenzyl)amino-2-phenyl-piperidine Hydrochloride

The title compound was prepared by a procedure similar to that described in Example 91.

M.p. 242°–243° C. (dec.).

$^1$H NMR (free base, CDCl$_3$) δ 0.88 (m, 3H), 1.60 (m, 13H), 2.14 (m, 1H), 2.44 (t, 2H, J=6), 2.78 (m, 2H), 3.26 (m, 1H), 3.40 (m, 4H), 3.64 (d, 1H, J=15), 3.86 (d, 1H, J=2), 6.58 (d, 1H, J=6), 6.75 (d, 1H, J=2), 6.92 (d, 1H, J=6), 7.26 (m, 5H).

HRMS Calc'd for $C_{26}H_{38}N_2O$: 394:2977. Found: 394.3009.

EXAMPLE 173

(2S,3S)-3-(2-Ethylaminobenzyl)amino-2-phenylpiperidine Hydrochloride

The title compound was prepared by treatment of the product of Example 165 with borane dimethylsulfide.

M.p. 210°–215° C. (dec).

$^1$H NMR (free base, CDCl$_3$) δ 0.97 (t, 3H, J=6), 1.56 (m, 3H), 2.05 (m, 1H), 2.80 (m, 4H), 3.12 (m, 1H), 3.24 (d, 1H, J=12), 3.46 (d, 1H, J=12), 3.82 (d, 1H, J=2), 6.46 (m, 2H), 6.70 (d, 1H, J=6), 7.03 (t, 1H, J=6), 7.22 (m, 5H).

HRMS Calc'd for $C_{20}H_{27}N_3$: 309.2199. Found: 309.2188.

EXAMPLE 174

(2S,3S)-1-(5,6-Difluorohex-1-yl)-3-(2-methoxybenzyl)amino-2-phenylpiperidine Hydrochloride The title compound was prepared by a procedure similar to that described in Example 2.

M.p. 52°–54° C. (dec).

$^1$H NMR (free base, CDCl$_3$) δ 1.44 (m, 7H), 1.88 (m, 2H), 2.00 (m, 3H), 2.51 (m, 2H), 3.18 (m, 1H), 3.26 (d, 1H, J=2), 3.33 (d, 1H, J=15), 3.44 (s, 3H), 3.66 (d, 1H, J=15), 4.40 (m, 3H), 6.60 (d, 1H, J=6), 6.72 (t, 1H, J=6), 6.83 (d, 1H, J=6), 7.07 (t, 1H, J=6), 7.24 (m, 5H).

HRMS Calc'd for $C_{25}H_{34}F_2N_2O$: 416.2639. Found: 416.2653.

Anal. Calc'd for $C_{25}H_{34}F_2N_2O \cdot 2HCl \cdot 1.5H_2O$: C, 58.14; H, 7.61; N, 5.42. Found: C, 58.36; H, 7.81; N, 5.32.

EXAMPLE 175

(2S,3S)-3-(2-Methoxy-5-n-propylbenzyl)amino-2-phenylpiperidine Hydrochloride

The title compound was prepared by a procedure similar to that described in Example 91.

M.p. 245°–247° C. (dec).

$^1$H NMR (free base, CDCl$_3$) δ 0.9 (m, 3H), 1.4 (m, 1H), 1.54 (m, 2H), 1.92 (m, 1H), 2.14 (m, 1H), 2.44 (t, 2H, J=6), 2.80 (m, 2H), 3.26 (m, 1H), 3.40 (d, 1H, J=15), 3.44 (s, 3H), 3.66 (d, 1H, J=15), 3.90 (s, 1H), 6.56 (d, 1H, J=10), 6.76 (s, 1), 6.92 (d, 1H, J=10), 7.26 (m, 5H), HRMS Calc'd for C$_{22}$H$_{30}$N$_2$O: 338.2351. Found: 338.2339.

Anal. Calc'd for C$_{22}$H$_{30}$N$_2$O$_2$·2HCl·0.25 H$_2$O: C, 63.57; H, 7.81; N, 6.74. Found: C, 63.59; H, 7.66; N, 6.73.

EXAMPLE 176

(2S,3S)-3-(4,5-Dimethyl-2-methoxybenzyl)amino-2-phenylpiperidine Hydrochloride

The title compound was prepared by a procedure similar to that describe in Example 91.

M.p. 269°–270° C. (dec).

$^1$H NMR (free base, CDCl$_{32}$) δ 1.40 (m, 1H), 1.60 (m, 1H), 1.96 (m, 2H); 2.14 (s, 3H), 2.18 (s, 3H), 2.80 (m, 2H), 3.30 (m, 1H), 3.40 (d, 1H, J=10), 3.42 (s, 3H), 3.62 (d, 1H, J=10), 3.90 (d, 1H, J=3), 6.48 (s, 1H), 6.70 (s, 1H), 7.28 (m, 5H).

HRMS Calc'd for C$_{21}$H$_{28}$N$_2$O: 324.2915: Found: 324.2210.

Anal. Calc'd for C$_{21}$H$_{28}$N$_2$O·2HCl·0.25 H$_2$O: C, 62.80; H, 7.60; N, 6.99. Found: C, 62.64; H, 7.31; N, 6.86.

EXAMPLE 177

(2S,3S)-3-(5-t-Butyl-2-hydroxybenzyl)amino-2-phenylpiperidine Hydrochloride

The title compound was prepared by a procedure similar to that described in Example 91.

M.p. >130° C. (dec).

$^1$H NMR (free base, CDCl$_3$) δ 1.2 (s, 9H), 1.6 (m, 3H), 2.1 (m, 1H), 2.72 (m, 1H), 2.90 (s, 1H), 3.16 (m, 1H), 3.38 (d, 1H, J=15), 3.50 (d, 1H, J=15), 3.90 (d, 1H, J=3), 6.62 (d, 1H, J=10), 6.68 (d, 1H, J=3), 7.08 (d, 1H, J=10), 7.32 (m, 5H).

HRMS Calc'd for C$_{22}$H$_{30}$N$_2$O: 338.2351. Found: 338.2384.

EXAMPLE 178

(2S,3S)-3-(5-Carbomethoxy-2-methoxybenzyl)amino-2-phenylpiperidine Hydrochloride The title compound was prepared by a procedure similar to that described in Example 91.

M.p. 238°–240° C. (dec).

$^1$H NMR (free base, CDCl$_3$) δ 1.4 (m, 1H), 1.6 (m, 1H), 1.88 (m, 2H), 2.1 (m, 1H), 2.75 (m, 2H), 3.2 (m, 1H), 3.35 (d, 1H, J=15), 3.45 (s, 3H), 3.7 (d, 1H, J=15), 3.85 (m, 4H), 6.65 (d, 1H, J=10), 7.2 (m, 5H), 7.70 (d, 1H, J=3), 7.85 (m, 1H).

HRMS Calc'd for C$_{21}$H$_{26}$N$_2$O$_3$: 354.1937. Found: 354.1932.

EXAMPLE 179

(2S,3S)-3-(5-n-Butyl-2-methoxybenzyl)amino-2-phenylpiperidine Hydrochloride

The title compound was prepared by a procedure similar to that described in Example 91.

M.p. 252°–253° C. (dec).

$^1$H NMR (free base, CDCl$_3$) δ 0.96 (m, 3H), 1.38 (m, 3H), 1.56 (m, 3H), 1.96 (m, 2H), 2.18 (m, 1H), 2.50 (m, 2H), 2.86 (m, 2H), 3.30 (m, 1H), 3.44 (d, 1H, J=15), 3.48 (s, 3H), 3.68 (d, 1H, J=15), 3.92 (d, 1H, J=3), 6.62 (d, 1H, J=10), 6.80 (s, 1H), 6.96 (d, 1H, J=10), 7.30 (m, 5H).

Anal. Calc'd for C$_{23}$H$_{32}$N$_2$O·2HCl·0.33 H$_2$O: C, 64.03; H, 8.09; N, 6.50. Found: C, 64.39; H, 7.90; N, 6.59.

EXAMPLE 180

(2S,3S)-3-(5-Isopropyl-2-methoxybenzyl)amino-2-phenylpiperidine Hydrochloride

The title compound was prepared by a procedure similar to that described in Example 91.

M.p. 252°–254° C. $^1$H NMR (free base, CDCl$_3$) δ 1.14 (d, 6H, J=6), 1.24 (m, 1H), 1.58 (m, 1H), 1.78 (m, 1H), 2.1 (m, 1H), 2.76 (m, 3H), 3.24 (m, 1H), 3.36 (d, 1H, J=12), 3.42 (s, 3H), 3.60 (d, 1H, J=12), 3.86 (d, 1H, J=3), 6.56 (d, 1H, J=6), 6.80 (d, 1H, J=3), 6.84 (m, 1H), 7.24 (m, 5H).

HRMS Calc'd for C$_{22}$H$_{30}$N$_2$O: 338.2351. Found: 338.2377.

Anal. Calc'd for C$_{22}$H$_{30}$N$_2$O·2HCl·0.26 H$_2$O: C, 63.52; H, 7.88; N, 6.74. Found: C, 63.33; H, 7.64, N, 6.75.

EXAMPLE 181

(2S,3S)-1-(4-t-Butyramidobut-1-yl)-3-(2-methoxybenzyl)amino-2-phenylpiperidine Hydrochloride The title compound was prepared by a procedure similar to that described in Example 95.

$^1$H NMR (free base, CDCl$_3$) δ 1.1 (s, 9H), 1.4 (m, 2H), 1.64 (m, 6H), 1.98 (m, 2H), 2.48 (m, 2H), 3.08 (m, 2H), 3.24 (d, 1H, J=3), 3.32 (d, 1H, J=15), 3.38 (s, 3H), 3.42 (d, 1H, J=15), 3.64 (d, 1H, J=15), 6.58 (d, 1H, J=10), 6.70 (m, 1H), 6.80 (d, 1H, J=10), 7.08 (m, 1H), 7.26 (s, 5H).

HRMS Calc'd for C$_{28}$H$_{41}$N$_3$O$_2$: 451.3189. Found: 451.3123.

EXAMPLE 182

(2S,3S)-(3-Benzamidoprop-1-yl)-3-(2-methoxybenzyl)amino-2-phenylpiperidine Hydrochloride The title compound was prepared by a procedure similar to that described in Example 95.

M.p. 98° C. (dec).

$^1$H NMR (free base, CDCl$_3$) δ 1.4 (m, 3H), 1.96 (m, 6H), 2.58 (m, 1H), 2.67 (m, 1H), 3.1 (m, 1H), 3.22 (d, 1H, J=3), 3.32 (s, 3H), 3.42 (d, 1H, J=15), 3.74 (d, 1H, J=15), 3.94 (m, 1H), 6.59 (d, 1H, J=10), 6.70 (m, 1H), 6.82 (d, 1H, J=10), 7.06 (m, 1H), 7.30 (m, 8H), 8.06 (d, 2H, J=10), 8.52 (m, 1H).

HRMS Calc'd for C$_{29}$H$_{34}$N$_3$O$_2$: 456.2643. Found: 456.2613.

EXAMPLE 183 cis-3-(5-Cyclopentyl-2-methoxybenzyl)amino-2-phenylpiperidine Hydrochloride

The title compound was prepared by a procedure similar to that described in Example 1.

M.p. 244°–246° C.

¹H NMR (free base, CDCl₃) δ 1.40–2.10 (m, 12H), 2.17 (d, 1H), 2.7–2.95 (m, 3H), 3.3 (d, 1H), 3.45 (d, 1H, J=13), 3.50 (s, 3H), 3.68 (d, 1H, J=13), 3.90 (d, 1H, J=2), 6.66 (d, 1H, J=7), 6.85 (d, 1H, J=2), 7.0 (dd, 1H), 7.20–7.40 (m, 6H). ¹³C NMR (free base, CDCl₃) δ 20.3, 25.4, 28.2, 34.7, 34.8, 45.1, 46.8, 47.8, 54.9, 64.0, 109.6, 125.9, 126.4, 126.5, 126.6, 127.8, 128.1, 128.2, 128.4, 137.8, 142.4, 155.7.

Mass spectrum: m/z 364 (parent).

Anal. Calc'd for $C_{24}H_{32}N_2O \cdot 2HCl \cdot 0.5\ H_2O$: C, 64.57; H, 7.90; N, 6.27. Found: C, 64.75; H, 7.66; N, 6.40.

We claim:

1. A compound of the formula

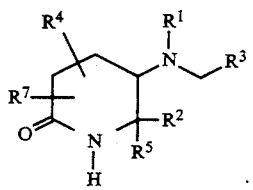

wherein $R^1$ is hydrogen or $(C_1-C_8)$ alkyl optionally substituted with hydroxy, alkoxy or fluoro;

$R^2$ is a radical selected from hydrogen, $(C_1-C_6)$ straight of branched alkyl, $(C_3-C_7)$ cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_6)$ alkyl, $(C_1-C_6)$ alkoxy, trifluoromethyl, amino, $(C_1-C_6)$-alkylamino,

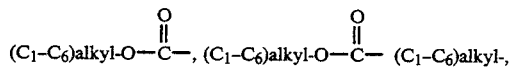

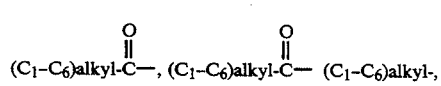

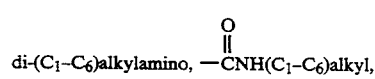

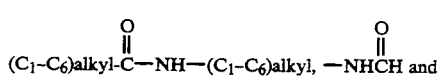

and wherein one of the phenyl moieties of said benzhydryl may optionally be replaced by naphthyl, thienyl, furyl or pyridyl;

$R^5$ is hydrogen, phenyl or $(C_1-C_6)$alkyl; or $R^2$ and $R^5$, together with the carbon to which they are attached, form a saturated carbocyclic ring having from 3 to 7 carbon atoms wherein one of said carbon atoms may optionally be replaced by oxygen, nitrogen or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl, $(C_1-C_6)$ alkoxy, trifluoromethyl, phenyl, amino, $(C_1-C_6)$ alkylamino,

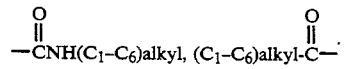

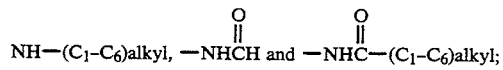

and $R^4$ and $R^7$ are each independently selected from hydroxy, halo, amino, oxo (=O), nitrile, $(C_1-C_6)$alkylamino, di-$(C_1-C_6)$alkylamino, $(C_1-C_6)$alkoxy,

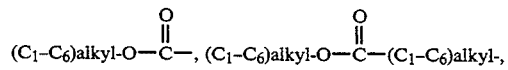

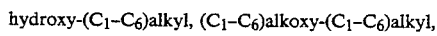

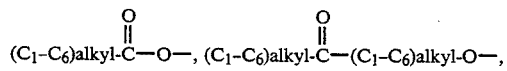

and the radicals set forth in the definition of $R^2$; with the proviso that (a) neither $R^4$ nor $R^7$ can form, together with the carbon to which it is attached, a ring with $R^5$, (b) when $R^4$ and $R^7$ are attached to the same carbon atom, then either each of $R^4$ and $R^7$ is independently selected from hydrogen, fluoro and $(C_1-C_6)$ alkyl, or $R^4$ and $R^7$, together with the carbon to which they are attached, form a $(C_3-C_6)$ saturated carbocyclic ring that forms a spiro compound with the nitrogen-containing ring to which they are attached, and (c) $R^2$ and $R^5$ cannot both be hydrogen.

2. (2S,3S)-3-amino-2-phenylpiperidine.

* * * * *